US011104709B2

(12) United States Patent
Jayasinghe et al.

(10) Patent No.: US 11,104,709 B2
(45) Date of Patent: Aug. 31, 2021

(54) MUTANT PORE

(71) Applicant: Oxford Nanopore Technologies Limited., Oxford (GB)

(72) Inventors: Lakmal Jayasinghe, Oxford (GB); Mark John Bruce, Oxford (GB); Luke McNeill, Oxford (GB); Ramiz Iqbal Nathani, Oxford (GB); Pratik Raj Singh, Oxford (GB); Neil Roger Wood, Oxford (GB); Stephen Robert Young, Oxford (GB)

(73) Assignee: Oxford Nanopore Technologies Ltd., Oxford (GB)

( * ) Notice: Subject to any disclaimer, the term of this patent is extended or adjusted under 35 U.S.C. 154(b) by 0 days.

(21) Appl. No.: 16/091,746

(22) PCT Filed: Apr. 6, 2017

(86) PCT No.: PCT/GB2017/050961
§ 371 (c)(1),
(2) Date: Oct. 5, 2018

(87) PCT Pub. No.: WO2017/174990
PCT Pub. Date: Oct. 12, 2017

(65) Prior Publication Data
US 2019/0202876 A1    Jul. 4, 2019

(30) Foreign Application Priority Data

Apr. 6, 2016   (GB) ..................................... 1605899
May 11, 2016  (GB) ..................................... 1608274

(51) Int. Cl.
*A61K 35/62*     (2006.01)
*C07K 14/435*    (2006.01)

(52) U.S. Cl.
CPC ........ *C07K 14/43536* (2013.01); *A61K 35/62* (2013.01)

(58) Field of Classification Search
None
See application file for complete search history.

(56) References Cited

U.S. PATENT DOCUMENTS

| | | |
|---|---|---|
| 5,795,782 A | 8/1998 | Church et al. |
| 6,015,714 A | 1/2000 | Baldarelli et al. |
| 6,114,121 A | 9/2000 | Fujiwara et al. |
| 6,362,002 B1 | 3/2002 | Denison et al. |
| 6,426,231 B1 | 7/2002 | Bayley et al. |
| 6,627,067 B1 | 9/2003 | Branton et al. |
| 6,824,659 B2 | 11/2004 | Bayley et al. |
| 6,863,833 B1 | 3/2005 | Bloom et al. |
| 6,916,665 B2 | 7/2005 | Bayley et al. |
| 6,927,070 B1 | 8/2005 | Bayley et al. |
| 7,189,503 B2 | 3/2007 | Akeson et al. |
| 8,105,846 B2 | 1/2012 | Bayley et al. |
| 8,785,211 B2 | 7/2014 | Bayley et al. |
| 8,822,160 B2 | 9/2014 | Bayley et al. |
| 8,828,208 B2 | 9/2014 | Canas et al. |
| 9,073,990 B2 | 7/2015 | Paas et al. |
| 9,127,313 B2 | 9/2015 | Brown et al. |
| 9,222,082 B2 | 12/2015 | Jayasinghe et al. |
| 9,447,152 B2 | 9/2016 | Clarke et al. |
| 9,562,887 B2 | 2/2017 | Maglia et al. |
| 9,580,480 B2 | 2/2017 | Lu et al. |
| 9,588,079 B2 | 3/2017 | Gundlach et al. |
| 9,732,381 B2 | 8/2017 | Stoddart et al. |
| 9,751,915 B2 | 9/2017 | Clarke et al. |
| 9,777,049 B2 | 10/2017 | Bruce et al. |
| 10,006,905 B2 | 6/2018 | Maglia et al. |
| 10,167,503 B2 | 1/2019 | Clarke et al. |
| 10,266,885 B2 | 4/2019 | Jayasinghe et al. |
| 10,385,389 B2 | 8/2019 | Heron et al. |
| 10,400,014 B2 | 9/2019 | Howorka et al. |
| 10,443,097 B2 | 10/2019 | Jayasinghe et al. |
| 10,472,673 B2 | 11/2019 | Maglia et al. |
| 10,514,378 B2 | 12/2019 | Maglia et al. |
| 10,669,581 B2 | 6/2020 | Stoddart et al. |
| 10,844,432 B2 | 11/2020 | Jayasinghe et al. |
| 10,882,889 B2 | 1/2021 | Bruce et al. |
| 2002/0028458 A1 | 3/2002 | Lexow |
| 2002/0094526 A1 | 7/2002 | Bayley et al. |
| 2002/0197614 A1 | 12/2002 | Mosaic |
| 2003/0044816 A1 | 3/2003 | Denison et al. |
| 2003/0099951 A1 | 5/2003 | Akeson et al. |
| 2003/0165936 A1 | 9/2003 | Rabbani et al. |
| 2003/0211502 A1 | 11/2003 | Sauer et al. |
| 2003/0215881 A1 | 11/2003 | Bayley et al. |
| 2004/0214177 A1 | 10/2004 | Bension |

(Continued)

FOREIGN PATENT DOCUMENTS

| | | |
|---|---|---|
| CA | 2381139 A1 | 3/2001 |
| CN | 102116783 A | 7/2011 |

(Continued)

OTHER PUBLICATIONS

PCT/GB2017/050961, Aug. 18, 2017, International Search Report and Written Opinion.
PCT/GB2017/050961, Oct. 18, 2018, International Preliminary Report on Patentability.
International Search Report and Written Opinion for Application No. PCT/GB2017/050961, dated Aug. 18, 2017.
International Preliminary Report on Patentability for Application No. PCT/GB2017/050961, dated Oct. 18, 2018.

(Continued)

*Primary Examiner* — Sarvamangala Devi

(74) *Attorney, Agent, or Firm* — Wolf, Greenfield & Sacks, P.C.

(57) ABSTRACT

The invention relates to mutant forms of lysenin. The invention also relates to analyte characterisation using the mutant forms of lysenin.

1 Claim, 5 Drawing Sheets

Specification includes a Sequence Listing.

(56) References Cited

U.S. PATENT DOCUMENTS

| | | |
|---|---|---|
| 2005/0053961 A1 | 3/2005 | Akeson et al. |
| 2006/0063171 A1 | 3/2006 | Akeson et al. |
| 2006/0105461 A1 | 5/2006 | Tom-Moy et al. |
| 2007/0218471 A1 | 9/2007 | Kim et al. |
| 2008/0311582 A1 | 12/2008 | Bayley et al. |
| 2009/0256116 A1 | 10/2009 | Shumaker-Parry et al. |
| 2009/0283412 A1 | 11/2009 | Sansinena et al. |
| 2009/0298075 A1 | 12/2009 | Travers et al. |
| 2009/0298188 A1 | 12/2009 | Peti-Peterdi |
| 2010/0120098 A1 | 5/2010 | Grunenwald et al. |
| 2010/0196203 A1 | 8/2010 | Sanghera et al. |
| 2010/0297638 A1 | 11/2010 | Bayley et al. |
| 2011/0120871 A1 | 5/2011 | Reid et al. |
| 2011/0121840 A1 | 5/2011 | Sanghera et al. |
| 2011/0177498 A1 | 7/2011 | Clarke et al. |
| 2011/0229877 A1 | 9/2011 | Jayasinghe et al. |
| 2011/0311965 A1 | 12/2011 | Maglia et al. |
| 2012/0058468 A1 | 3/2012 | Mckeown |
| 2012/0064599 A1 | 3/2012 | Jayasinghe et al. |
| 2012/0100530 A1 | 4/2012 | Moysey et al. |
| 2012/0107802 A1 | 5/2012 | Stoddart et al. |
| 2012/0322679 A1 | 12/2012 | Brown et al. |
| 2014/0051069 A1 | 2/2014 | Jayasinghe et al. |
| 2014/0186823 A1 | 7/2014 | Clarke et al. |
| 2014/0262784 A1 | 9/2014 | Clarke et al. |
| 2014/0296083 A1 | 10/2014 | Brown et al. |
| 2015/0008126 A1 | 1/2015 | Maglia et al. |
| 2015/0031020 A1 | 1/2015 | Jayasinghe et al. |
| 2015/0068904 A1 | 3/2015 | Bruce et al. |
| 2015/0175663 A1 | 6/2015 | Yokoi et al. |
| 2015/0177237 A1 | 6/2015 | Turner et al. |
| 2015/0346149 A1 | 12/2015 | Brown et al. |
| 2016/0005330 A1 | 1/2016 | Maglia et al. |
| 2016/0010147 A1 | 1/2016 | Heron et al. |
| 2016/0370358 A1 | 12/2016 | Maglia et al. |
| 2017/0058337 A1 | 3/2017 | Clarke et al. |
| 2017/0058338 A1 | 3/2017 | Jayasinghe et al. |
| 2017/0107569 A1 | 4/2017 | Heron et al. |
| 2017/0233803 A1 | 8/2017 | Stoddart et al. |
| 2017/0306398 A1 | 10/2017 | Jayasinghe et al. |
| 2018/0030526 A1 | 2/2018 | Brown et al. |
| 2018/0095066 A1 | 4/2018 | Jayasinghe et al. |
| 2018/0148481 A2 | 5/2018 | Howorka et al. |
| 2018/0208632 A1 | 7/2018 | Bruce et al. |
| 2018/0209952 A1 | 7/2018 | Maglia et al. |
| 2018/0334707 A1 | 11/2018 | Stoddart et al. |
| 2018/0335425 A1 | 11/2018 | Maglia et al. |
| 2018/0364214 A1 | 12/2018 | Maglia et al. |
| 2019/0071721 A1 | 3/2019 | Jayasinghe et al. |
| 2019/0300582 A1 | 10/2019 | Jayasinghe et al. |
| 2019/0330282 A1 | 10/2019 | Jayasinghe et al. |
| 2019/0346431 A1 | 11/2019 | Maglia et al. |
| 2020/0017556 A1 | 1/2020 | Howorka et al. |
| 2020/0072824 A1 | 3/2020 | Maglia et al. |
| 2020/0087724 A1 | 3/2020 | Heron et al. |
| 2020/0224262 A1 | 7/2020 | Jayasinghe et al. |
| 2020/0407785 A1 | 12/2020 | Stoddart et al. |

FOREIGN PATENT DOCUMENTS

| | | |
|---|---|---|
| CN | 102174554 A | 9/2011 |
| CN | 102317310 A | 1/2012 |
| CN | 103460040 A | 12/2013 |
| EP | 2194123 B1 | 8/2012 |
| EP | 2682460 A1 | 1/2014 |
| GB | 2453377 A | 4/2009 |
| JP | H10-146190 A | 6/1998 |
| JP | 2005-253427 A | 9/2005 |
| JP | 2015-514128 A | 5/2015 |
| WO | WO 1999/005167 A1 | 2/1999 |
| WO | WO 2000/028312 A1 | 5/2000 |
| WO | WO 2001/042782 A1 | 6/2001 |
| WO | WO 2001/059453 A2 | 8/2001 |
| WO | WO 2002/042496 A2 | 5/2002 |
| WO | WO 2003/095669 A1 | 11/2003 |
| WO | WO 2006/028508 A2 | 3/2006 |
| WO | WO 2006/100484 A2 | 9/2006 |
| WO | WO 2007/057668 A1 | 5/2007 |
| WO | WO 2007/075987 A2 | 7/2007 |
| WO | WO 2007/084103 A2 | 7/2007 |
| WO | WO 2008/102120 A1 | 8/2008 |
| WO | WO 2008/102121 A1 | 8/2008 |
| WO | WO 2008/124107 A1 | 10/2008 |
| WO | WO 2009/024775 A1 | 2/2009 |
| WO | WO 2009/035647 A1 | 3/2009 |
| WO | WO 2009/044170 A1 | 4/2009 |
| WO | WO 2009/077734 A2 | 6/2009 |
| WO | WO 2009/143425 A1 | 11/2009 |
| WO | WO 2010/004265 A1 | 1/2010 |
| WO | WO 2010/004273 A1 | 1/2010 |
| WO | WO 2010/034018 A2 | 3/2010 |
| WO | WO 2010/055307 A1 | 5/2010 |
| WO | WO 2010/086602 A1 | 8/2010 |
| WO | WO 2010/086603 A1 | 8/2010 |
| WO | WO 2010/086622 A1 | 8/2010 |
| WO | WO 2010/122293 A1 | 10/2010 |
| WO | WO 2011/067559 A1 | 6/2011 |
| WO | WO 2012/042226 A1 | 4/2012 |
| WO | WO 2012/107778 A2 | 8/2012 |
| WO | WO 2012/164270 A1 | 12/2012 |
| WO | WO 2013/014451 A1 | 1/2013 |
| WO | WO 2013/041878 A1 | 3/2013 |
| WO | WO 2013/057495 A1 | 4/2013 |
| WO | WO 2013/098561 A1 | 7/2013 |
| WO | WO 2013/098562 A1 | 7/2013 |
| WO | WO 2013/109970 A1 | 7/2013 |
| WO | WO 2013/153359 A1 * | 10/2013 |
| WO | WO 2014/013259 A1 | 1/2014 |
| WO | WO 2014/013260 A1 | 1/2014 |
| WO | WO 2014/013262 A1 | 1/2014 |
| WO | WO 2014/064443 A1 | 5/2014 |
| WO | WO 2014/064444 A1 | 5/2014 |
| WO | WO 2014/122654 A2 | 8/2014 |
| WO | WO 2014/135838 A1 | 9/2014 |
| WO | WO 2014/153047 A1 | 9/2014 |
| WO | WO 2014/153625 A1 | 10/2014 |
| WO | WO 2015/022544 A1 | 2/2015 |
| WO | WO 2015/051378 A1 | 4/2015 |
| WO | WO 2015/055981 A1 | 4/2015 |
| WO | WO 2015/110777 A1 | 7/2015 |
| WO | WO 2015/124935 A1 | 8/2015 |
| WO | WO 2015/150786 A1 | 10/2015 |
| WO | WO 2015/150787 A1 | 10/2015 |
| WO | WO 2015/166275 A1 | 11/2015 |
| WO | WO 2015/166276 A1 | 11/2015 |
| WO | WO 2016/055778 A1 | 4/2016 |
| WO | WO 2016/166232 A1 | 10/2016 |

OTHER PUBLICATIONS

Aoki et al., Single channel properties of lysenin measured in artificial lipid bilayers and their applications to biomolecule detection. Proc Jpn Acad Ser B Phys Biol Sci. 2010;86(9):920-5.

Fologea et al., Potential analytical applications of lysenin channels for detection of multivalent ions. Anal Bioanal Chem. Oct. 2011;401(6):1871-9. doi: 10.1007/s00216-011-5277-8. Epub Aug. 5, 2011.

Ide et al., Lysenin forms a voltage-dependent channel in artificial lipid bilayer membranes. Biochem Biophys Res Commun. Jul. 21, 2006;346(1):288-92. Epub May 26, 2006.

Kolinko et al., Single-cell genomics reveals potential for magnetite and greigite biomineralization in an uncultivated multicellular magnetotactic prokaryote. Environ Microbiol Rep. Oct. 2014;6(5):524-31. doi: 10.1111/1758-2229.12198. Epub Aug. 28, 2014. Abstract Only.

Skočaj et al., The sensing of membrane microdomains based on pore-forming toxins. Curr Med Chem. 2013;20(4):491-501.

[No Author Listed] EBI Accession No. GSP:AXX09397. May 13, 2010.

[No Author Listed] EBI Accession No. A0A085GH19. Oct. 29, 2014.

[No Author Listed] EBI Accession No. A0A0D1LDB9. Apr. 29, 2015.

(56) References Cited

OTHER PUBLICATIONS

[No Author Listed] EBI Accession No. EMBLCDS:ABV05494. Sep. 11, 2007.
[No Author Listed] Helicos BioSciences Corporation, "Helicos Genetic Analysis System," Specification Sheet retrieved online at: www.helicosbio.com/Portals/0/Documents/Helicos_SalesSpec. pdf, 4 pages (2008).
[No Author Listed] Uniprot Accession No. A0A081NL13. Oct. 29, 2014. 4 pages.
[No Author Listed] Uniprot Accession No. A0A0P7DN88. Jan. 20, 2016. 4 pages.
[No Author Listed] Uniprot Accession No. Q8Z727. Oct. 24, 2003. 6 pages.
Ahern, Biochemical, reagents kits offer scientists good return on investment. The Scientist. Jul. 24, 1995;9(15):20.
Akeson et al., Microsecond time-scale discrimination among polycytidylic acid, polyadenylic acid, and polyuridylic acid as homopolymers or as segments within single RNA molecules. Biophys J. Dec. 1999;77(6):3227-33.
Aravind et al., The DNA-Repair Protein AlkB, EGL-9, and Leprecan Define New Families of 2-oxoglutarate-andIron-Dependent Dioxygenases. Genome Biology. 2001;2:1-8.
Ashkenasy et al., Recognizing a single base in an individual DNA strand: a step toward DNA sequencing in nanopores. Angew Chem Int Ed Engl. Feb. 18, 2005;44(9):1401-4.
Ashkenasy et al., Single Nucleobase Sensitivity of a-Hemolysin (a-HL) Transmembrane Protein Pore: Toward Single DNA Sequencing. ACS National Meeting. 2005;45(13), Abstract No. 74.
Ashton et al., MinION Nanopore Sequencing Identifies the Position and Structure of a Bacterial antibiotic Resistance Island. Nat Biotechnol. Mar. 2015;33(3):296-302.
Astier et al., Stochastic detection of motor protein-RNA complexes by single-channel current recording. Chemphyschem. Oct. 22, 2007;8(15):2189-94.
Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.
Atkins et al., Structure-function relationships of a novel bacterial toxin, hemolysin E. The role of alpha G. J Biol Chem. Dec. 29, 2000;275(52):41150-5.
Avrameas, Coupling of enzymes to proteins with glutaraldehyde. Use of the conjugates for the detection of antigens and antibodies. Immunochemistry. Jan. 1969;6(1):43-52.
Bayley et al., Stochastic sensors inspired by biology. Nature. Sep. 13, 2001;413(6852):226-30.
Bayley et al., Wrestling with native chemical ligation. ACS Chem Biol. Dec. 18, 2009;4(12):983-5. doi: 10.1021/cb900304p.
Bayley, Membrane-protein structure: Piercing insights. Nature. Jun. 4, 2009;459(7247):651-2. doi: 10.1038/459651a.
Bayley, Nanopore Sequencing: From Imagination to Reality. Clin Chem. 2015;61(1):25-31.
Bayley, Sequencing single molecules of DNA. Curr Opin Chem Biol. Dec. 2006;10(6):628-37. Epub Nov. 20, 2006.
Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.
Bezrukov et al., Counting Polymers Moving Through a Single Ion Channel. Nature. Jul. 28, 1994;370:279-81.
Bianco, Helicase unwinding: active or merely perfect? J Mol Biol. Jul. 13, 2012;420(3):139-40. doi: 10.1016/j.jmb.2012.04.030. Epub May 2, 2012.
Bleijlevens et al., Changes in Protein Dynamics of the DNA Repair Dioxygenase AlkB Upon Binding of FE2+ and 2-Oxoglutarate. Biochemistry. Mar. 26, 2012;51:3334-41.
Bleijlevens et al., Dynamic States of the DNA Repair Enzyme AlkB regulate Product Release. Eur Mol Biol Org. Jul. 11, 2008;9(9):872-77.

Bourdon et al., Molecular cloning and sequence analysis of a chondroitin sulfate proteoglycan cDNA. Proc Natl Acad Sci U S A. Mar. 1985;82(5):1321-5.
Braha et al., Carriers versus adapters in stochastic sensing. Chemphyschem. May 2005;6(5):889-92.
Braha et al., Designed protein pores as components for biosensors. Chem Biol. Jul. 1997;4(7):497-505.
Branton et al., The potential and challenges of nanopore sequencing. Nat Biotechnol. Oct. 2008;26(10):1146-53. doi:10.1038/nbt.1495.
Braslavsky et al., Sequence information can be obtained from single DNA molecules. Proc Natl Acad Sci U S A. Apr. 1, 2003;100(7):3960-4. Epub Mar. 21, 2003.
Butler et al., Determination of RNA orientation during translocation through a biological nanopore. Biophys J. Jan. 1, 2006;90(1):190-9. Epub Oct. 7, 2005.
Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.
Byrd et al., Dda helicase tightly couples translocation on single-stranded DNA to unwinding of duplex DNA: Dda is an optimally active helicase. J Mol Biol. Jul. 13, 2012;420(3):141-54. doi: 10.1016/j.jmb.2012.04.007. Epub Apr. 11, 2012.
Cao et al., Structure of the nonameric bacterial amyloid secretion channel. Proc Natl Acad Sci U S A. Dec. 16, 2014;111(50):E5439-44. doi: 10.1073/pnas.1411942111. Epub Dec. 1, 2014.
Chan, Advances in sequencing technology. Mutat Res. Jun. 3, 2005;573(1-2):13-40.
Cheley et al., A functional protein pore with a "retro" transmembrane domain. Protein Sci. Jun. 1999;8(6):1257-67.
Cheley et al., A genetically encoded pore for the stochastic detection of a protein kinase. Chembiochem. Dec. 2006;7(12):1923-7.
Cheley et al., Spontaneous oligomerization of a staphylococcal alpha-hemolysin conformationally constrained by removal of residues that form the transmembrane beta-barrel. Protein Eng. Dec. 1997;10(12):1433-43.
Chen et al., Atomic Layer Deposition to Fine-Tune the Surface Properties and Diameters of Fabricated Nanopores. Nano Lett. Jun. 25, 2004;4(7):1333-1337.
Chen et al., Outer membrane protein G: Engineering a quiet pore for biosensing. Proc Natl Acad Sci U S A. Apr. 29, 2008;105(17):6272-7. doi: 10.1073/pnas.0711561105. Epub Apr. 28, 2008.
Cheng et al., Design and testing of aptamer-based electrochemical biosensors for proteins and small molecules. Bioelectrochemistry. Nov. 2009;77(1):1-12. doi: 10.1016/j.bioelechem.2009.04.007. Epub May 5, 2009.
Chin et al., The Metabolite alpha-Ketoglutarate Extends Lifespan by Inhibiting ATP Synthase and TOR. Nature. Jul. 19, 2014;510:397-401.
Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.
Cockroft et al., A single-molecule nanopore device detects DNA polymerase activity with single-nucleotide resolution. J Am Chem Soc. Jan. 23, 2008;130(3):818-20. doi: 10.1021/ja077082c. Epub Jan. 1, 2008.
Comai et al., Protein engineering modulates the transport properties and ion selectivity of the pores formed by staphylococcal gamma-haemolysins in lipid membranes. Mol Microbiol. Jun. 2002;44(5):1251-67.
Dani et al., MspA Porin-Gold Nanoparticle Assemblies: Enhanced Binding through a Controlled Cysteine Mutation. Nano Lett. Apr. 2008;8(4):1229-36. doi: 10.1021/nl072658h. Epub Mar. 5, 2008.
Deamer et al., Characterization of nucleic acids by nanopore analysis. Acc Chem Res. Oct. 2002;35(10):817-25.
Deamer et al., Nanopores and nucleic acids: prospects for ultrarapid sequencing. Trends Biotechnol. Apr. 2000;18(4):147-51.
Derrington et al., A Novel DNA Sensing Technique Using Nanopore MSPA. 54th Annual Meeting of the Biophysical Society, Poster 2182—Plat, 2 pages (2010).
Derrington et al., Nanopore DNA sequencing with MspA. Proc Natl Acad Sci U S A. Sep. 14, 2010;107(37):16060-5. doi: 10.1073/pnas.1001831107. Epub Aug. 26, 2010.

(56) References Cited

OTHER PUBLICATIONS

Dorre et al., Techniques for single molecule sequencing. Bioimaging, vol. 5:139-152 (1997).
Eid et al., Real-time DNA sequencing from single polymerase molecules. Science. Jan. 2, 2009;323(5910):133-8. doi:10.1126/science.1162986. Epub Nov. 20, 2008.
Eliseev et al., Aminocyclodextrins as Selective Hosts with Several Binding Sites for Nucleotides. Angew. Chem. Int. Ed. Engl., vol. 32(9):1331-1333 (1993).
Eliseev et al., Molecular Recognition of Nucleotides, Nucleosides, and Sugars by Aminocyclodextrins. J. Am. Chem. Soc., vol. 116:6081-6088 (1994).
Engelhardt et al., A tetrameric porin limits the cell wall permeability of *Mycobacterium smegmatis*. J Biol Chem. Oct. 4, 2002;277(40):37567-72. Epub Jul. 18, 2002.
Ergel et al., Protein Dynamics Control the Progression and Efficiency of the Catalytic Reaction Cycle of the *Escherichia coli* DNA-Repair Enzyme AlkB. J Biol Chem. Oct. 24, 2014;289(43):29584-601.
Fahie et al., Resolved Single-Molecule Detection of Individual Species Within a Mixture of Anti-Biotin Antibodies Using an Engineered Monometric Nanopore. Am Chem Soc. Jan. 9, 2015;9(2):1089-98.
Flomenbom et al., Single stranded DNA translocation through a nanopore: a master equation approach. Phys Rev E Stat Nonlin Soft Matter Phys. Oct. 2003;68(4 Pt 1):041910. Epub Oct. 14, 2003.
Flusberg et al., Direct detection of DNA methylation during single-molecule, real-time sequencing. Nat Methods. Jun. 2010;7(6):461-5. doi: 10.1038/nmeth.1459. Epub May 9, 2010.
Franceschini et al., A nanopore machine promotes the vectorial transport of DNA across membranes. Sep. 2013; Nat Commun. 2013;4:2415. doi: 10.1038/ncomms3415.
Franceschini et al., DNA Translocation through Nanopores at Physiological Ionic Strengths Requires Precise Nanoscale Engineering. ACS Nano. Sep. 27, 2016;10(9):8394-402. doi: 10.1021/acsnano.6b03159. Epub Aug. 15, 2016.
Freedman et al., Single Molecule Unfolding and Stretching of Protein Domains Inside a Solid-State Nanopore by Electric Field. Scientific Reports. Apr. 10, 2013;3(1638):1-8.
Galenkamp et al., Direct electrical quantification of glucose and asparagine from bodily fluids using nanopores. Nat Commun. 2018;9(1):4085. Published Oct. 5, 2018. doi:10.1038/s41467-018-06534-1.
Genschel et al., Interaction of *E. coli* single-stranded DNA binding protein (SSB) with exonuclease I. The carboxy-terminus of SSB is the recognition site for the nuclease. Biol Chem. Mar. 2000;381(3):183-92.
Gershow et al., Recapturing and trapping single molecules with a solid-state nanopore. Nat Nanotechnol. Dec. 2007;2(12):775-9. doi:10.1038/nnano.2007.381. Epub Dec. 2, 2007.
Ghosal, Electrokinetic-flow-induced viscous drag on a tethered DNA inside a nanopore. Phys Rev E Stat Nonlin Soft Matter Phys. Dec. 2007;76(6 Pt 1):061916. Epub Dec. 26, 2007.
Gilbert et al., Two Structural Transitions in Membrane Pore Formation by Pneumolysin, the Pore-Forming Toxin of *Streptococcus pneumoniae*. Cell. May 28, 1999;97:647-655.
Gouridis et al., Conformational Dynamics in Substrate-Binding Domains Influences Transport in the ABC Importer GinPQ. Nat Stuct Mol Biol. Dec. 8, 2014;22(1):57-66.
Goyal et al., Structural and mechanistic insights into the bacterial amyloid secretion channel CsgG. Nature. Dec. 11, 2014;516(7530):250-3 with Supplemental Information. doi: 10.1038/nature13768. Epub Sep. 14, 2014.
Goyal et al., Structural and mechanistic insights into the bacterial amyloid secretion channel CsgG. Nature. Dec. 11, 2014;516(7530):250-3. doi: 10.1038/nature13768. Epub Sep. 14, 2014.
Gu et al., Capture of a single molecule in a nanocavity. Science. Jan. 26, 2001;291(5504):636-40.
Gu et al., Electroosmotic enhancement of the binding of a neutral molecule to a transmembrane pore. Proc Natl Acad Sci U S A. Dec. 23, 2003;100(26):15498-503. Epub Dec. 15, 2003.
Gu et al., Interaction of the noncovalent molecular adapter, beta-cyclodextrin, with the staphylococcal alpha-hemolysin pore. Biophys J. Oct. 2000;79(4):1967-75.
Gu et al., Prolonged residence time of a noncovalent molecular adapter, beta-cyclodextrin, within the lumen of mutant alpha-hemolysin pores. J Gen Physiol. Nov. 2001;118(5):481-94.
Gu et al., Reversal of charge selectivity in transmembrane protein pores by using noncovalent molecular adapters. Proc Natl Acad Sci U S A. Apr. 11, 2000;97(8):3959-64.
Gu et al., Stochastic sensing of organic analytes by a pore-forming protein containing a molecular adapter. Nature. Apr. 22, 1999;398(6729):686-90.
Guan et al., Stochastic sensing of TNT with a genetically engineered pore. Chembiochem. Oct. 2005;6(10):1875-81.
Guasch et al., Detailed architecture of a DNA translocating machine: the high-resolution structure of the bacteriophage phi29 connector particle. J Mol Biol. Jan. 25, 2002;315(4):663-76.
Hall et al., Hybrid pore formation by directed insertion of ?-haemolysin into solid-state nanopores. Nat Nanotechnol. Dec. 2010;5(12):874-7. doi: 10.1038/nnano.2010.237. Epub Nov. 28, 2010.
Han et al., Characterization and optimization of an entropic trap for DNA separation. Anal Chem. Jan. 15, 2002;74(2):394-401.
Han et al., RecJ exonuclease: substrates, products and interaction with SSB. Nucleic Acids Res. Feb. 18, 2006;34(4):1084-91. Print 2006.
Haque et al., Solid-State and Biological Nanopore for Real-Time Sensing of Single Chemical and Sequencing of DNA. Nano Today. Feb. 2013;8(1):56-74.
He et al. 2012; The T4 phage SF1 B helicase dda is structurally optimized to perform DNA strand separation. Structure. 20:1189-1200.
Henrickson et al., Driven DNA transport into an asymmetric nanometer-scale pore. Phys Rev Lett. Oct. 2, 2000;85(14):3057-60.
Heron et al., Direct detection of membrane channels from gels using water-in-oil droplet bilayers. J Am Chem Soc. Dec. 26, 2007;129(51):16042-7. Epub Dec. 1, 2007.
Holden et al., Direct introduction of single protein channels and pores into lipid bilayers. J Am Chem Soc. May 11, 2005;127(18):6502-3.
Holden et al., Functional bionetworks from nanoliter water droplets. J Am Chem Soc. Jul. 11, 2007;129(27):8650-5. Epub Jun. 16, 2007.
Hornblower et al., Single-molecule analysis of DNA-protein complexes using nanopores. Nat Methods. Apr. 2007;4(4):315-7. Epub Mar. 4, 2007.
Howorka et al., DNA Duplex Formation of Individual DNA Strands within a Single Protein Pore. Biophysical Journal, vol. 82{1, pt. 2):508a, No. 2482—Plat (2002).
Howorka et al., Kinetics of duplex formation for individual DNA strands within a single protein nanopore. Proc Natl Acad Sci U S A. Nov. 6, 2001;98(23):12996-3001. Epub Oct. 23, 2001.
Howorka et al., Nanopore Analytics: Sensing of Single Molecules. The Royal Society of Chemistry. Jun. 15, 2009;38:2360-84.
Howorka et al., Nanopores as protein sensors. Nat Biotechnol. Jun. 7, 2012;30(6):506-7. doi: 10.1038/nbt.2264.
Howorka et al., Probing distance and electrical potential within a protein pore with tethered DNA. Biophys J. Dec. 2002;83(6):3202-10.
Howorka et al., Sequence-specific detection of individual DNA strands using engineered nanopores. Nat Biotechnol. Jul. 2001;19(7):636-9.
Hu et al., Theory of DNA translocation through narrow ion channels and nanopores with charged walls. Phys Rev E Stat Nonlin Soft Matter Phys. Sep. 2008;78(3 Pt 1):032901. Epub Sep. 10, 2008.
Huff et al., Functions of the periplasmic loop of the porin MspA from *Mycobacterium smegmatis*. J Biol Chem. Apr. 10, 2009;284(15):10223-31. doi: 10.1074/jbc.M808599200. Epub Feb. 10, 2009.
Hwang et al., Electrical behavior of droplet interface bilayer networks: experimental analysis and modeling. J Am Chem Soc. Sep. 26, 2007;129(38):11854-64. Epub Sep. 1, 2007.

(56) References Cited

OTHER PUBLICATIONS

Iacovache et al., Structure and assembly of pore-forming proteins. Curr Opin Struct Biol. Apr. 2010;20(2):241-6. doi:10.1016/j.sbi.2010.01.013. Epub Feb. 19, 2010.

Ivanov et al., DNA tunneling detector embedded in a nanopore. Nano Lett. Jan. 12, 2011;11(1):279-85. doi: 10.1021/nl103873a. Epub Dec. 6, 2010.

Jayasinghe et al., The leukocidin pore: evidence for an octamer with four LukF subunits and four LukS subunits alternating around a central axis. Protein Sci. Oct. 2005;14(10):2550-61.

Johnston et al., Coexpression of proteins in bacteria using T7-based expression plasmids: expression of heteromeric cell-cycle and transcriptional regulatory complexes. Protein Expr Purif. Dec. 2000;20(3):435-43.

Jung et al., The internal cavity of the staphylococcal alpha-hemolysin pore accommodates approximately 175 exogenous amino acid residues. Biochemistry. Jun. 28, 2005;44(25):8919-29.

Kalli et al., Conformational changes in talin on binding to anionic phospholipid membranes facilitate signaling by integrin transmembrane helices. PLoS Comput Biol. Oct. 2013;9(10):e1003316. doi:10.1371/journal.pcbi.1003316.

Kang et al., Single protein pores containing molecular adapters at high temperatures. Angew Chem Int Ed Engl. Feb. 25, 2005;44(10):1495-9.

Kasianowicz et al., Characterization of individual polynucleotide molecules using a membrane channel. Proc Natl Acad Sci U S A. Nov. 26, 1996;93(24):13770-3.

Khulbe et al., DNA translocation through a-hemolysin nanopores with potential application to macromolecular data storage. Journal Applied Physics, vol. 97(104317):1-7 (2005).

Kobayashi et al., Comparative Physiology and Biochemistry, 2005, vol. 22, No. 3-4, pp. 139-148.

Krylova et al., DNA aptamers for as analytical tools for the quantitative analysis of DNA-dealkylating enzymes. Anal Biochem. 2011;414(2):261-265. doi:10.1016/j.ab.2011.03.010.

Kumar et al., PEG-labeled nucleotides and nanopore detection for single molecule DNA sequencing by synthesis. Sci Rep. 2012;2:684. Epub Sep. 21, 2012.

Langecker et al., Synthetic lipid membrane channels formed by designed DNA nanostructures. Science. Nov. 16, 2012;338(6109):932-6. doi: 10.1126/science.1225624.

Li et al., Different Anomeric Sugar Bound States of Maltose Binding Protein Resolved by a Cytolysin A Nanopore Tweezer. ACS Nano. 2020;14(2):1727-1737. doi:10.1021/acsnano.9b07385.

Li et al., DNA molecules and configurations in a solid-state nanopore microscope. Nat Mater. Sep. 2003;2(9):611-5. Epub Aug. 24, 2003.

Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.

Lu et al., Protein Motion and Configurations in a Form-Fitting Nanopore: Avidin in ClyA. Biophys J. Sep. 4, 2018; 115(5):801-808. Epub Aug. 4, 2018. doi: 10.1016/j.bpj.2018.07.024.

Luchian et al., Single-Molecule Covalent Chemistry with Spatially Separated Reactants. Angew. Chem. Int. Ed. 2003;42:3766-771.

Ludwig et al., Analysis of the SlyA-Controlled Expression, Subcellular Localization and Pore-Forming Activity of a 34 kDa Haemolysin (ClyA) from *Escherichia coli* K-12. Mol Microbiol. 1999;31(2):557-67.

Luo et al., Influence of polymer-pore interactions on translocation. Phys Rev Lett. Oct. 5, 2007;99(14):148102. Epub Oct. 1, 2007.

Maglia et al., DNA strands from denatured duplexes are translocated through engineered protein nanopores at alkaline pH. Nano Lett. Nov. 2009;9(11):3831-6. doi: 10.1021/nl9020232.

Maglia et al., Engineering a Biomimetic Biological Nanopore to Selectively Capture Folded Target Proteins. Biophysical J. Feb. 5, 2013;104(2):518a.

Maglia et al., Enhanced translocation of single DNA molecules through alpha-hemolysin nanopores by manipulation of internal charge. Proc Natl Acad Sci U S A. Dec. 16, 2008;105(50):19720-5. doi:10.1073/pnas.0808296105. Epub Dec. 5, 2008.

Makaram et al., Trends in Nanomaterial-Based Non-Invasive Diabetes Sensing Technologies. Diagnostics. Apr. 21, 2014;4:27-46.

Manrao et al., Nucleotide Discrimination with DNA Immobilized in the MspA Nanopore. PLoS One, vol. 6(10):e25723, 7 pages (2011).

Manrao et al., Reading DNA at single-nucleotide resolution with a mutant MspA nanopore and phi29 DNA polymerase. Nat Biotechnol. Mar. 25, 2012;30(4):349-53. doi: 10.1038/nbt.2171.

Manrao et al., Single Nucleotide Discrimination in Single Stranded DNA Immobilized within Biological Nanopre MSPA. 54th Annual Meeting of the Biophysical Society, 3 pages (2010).

Martin et al., Nanoscale protein pores modified with PAMAM dendrimers. J Am Chem Soc. Aug. 8, 2007;129(31):9640-9. Epub Jul. 18, 2007.

Marziali et al., New DNA sequencing methods. Annu Rev Biomed Eng. 2001;3:195-223.

Mathé et al., Orientation discrimination of single-stranded DNA inside the alpha-hemolysin membrane channel. Proc Natl Acad Sci U S A. Aug. 30, 2005;102(35):12377-82. Epub Aug. 19, 2005.

Matsuura et al., Real-time observation of a single DNA digestion by lambda exonuclease under a fluorescence microscope field. Nucleic Acids Res. Aug. 15, 2001;29(16):E79.

Meller et al., Rapid nanopore discrimination between single polynucleotide molecules. Proc Natl Acad Sci U S A. Feb. 1, 2000;97(3):1079-84.

Meller et al., Single molecule measurements of DNA transport through a nanopore. Electrophoresis. Aug. 2002;23(16):2583-91.

Meller, Dynamics of polynucleotide transport through nanometre-scale pores. Journal Physics: Condensed Matter, vol. 15:R581-R607 (2003).

Merzlyak et al., Conductance and ion selectivity of a mesoscopic protein nanopore probed with cysteine scanning mutagenesis. Biophys J. Nov. 2005;89(5):3059-70. Epub Aug. 5, 2005.

Mikheyev et al., A First Look at the Oxford Nanopore MinION Sequencer. Mol Ecol Res. 2014;14:1097-1102.

Miles et al., The Staphylococcal Leukocidin Bicomponent Toxin Forms Large Ionic Channels. Biochemistry. Jun. 28, 2001;40:8514-522.

Mitchell et al., Chemical tags facilitate the sensing of individual DNA strands with nanopores. Angew Chem Int Ed Engl. 2008;47(30):5565-8. doi:10.1002/anie.200800183.

Miyazaki et al., MegaWhop Cloning: A Method of Creating Random Mutagenesis Libraries via Megaprimer PCR of Whole Plasmids. Methods in Enzymology. 2011;498:399-406.

Mohammad et al., Controlling a single protein in a nanopore through electrostatic traps. J Am Chem Soc. Mar. 26, 2008;130(12):4081-8. doi: 10.1021/ja710787a. Epub Mar. 6, 2008.

Moreau et al., Coupling ion channels to receptors for biomolecule sensing. Nat Nanotechnol. Oct. 2008;3(10):620-5. doi: 10.1038/nnano.2008.242. Epub Sep. 7, 2008.

Movileanu et al., Detecting protein analytes that modulate transmembrane movement of a polymer chain within a single protein pore. Nat Biotechnol. Oct. 2000;18(10):1091-5.

Movileanu et al., Location of a constriction in the lumen of a transmembrane pore by targeted covalent attachment of polymer molecules. J Gen Physiol. Mar. 2001;117(3):239-52.

Moyer et al., Correlation Between Sweat Glucose and Blood Glucose in Subjects with Diabetes. Diabetes Technol Ther. 2012:14(5):398-402.

Mueller et al., The Structure of Cytolytic alpha-Helical Toxin Pore Reveals its Assembly Mechanism. Nature. Jun. 4, 2009;459:726-731.

Mueller et al., The Structure of Cytolytic alpha-Helical Toxin Pore Reveals its Assembly Mechanism. Nature. Jun. 4, 2009;459:Supplemental Information.

Muller et al., DNA-directed assembly of artificial multienzyme complexes. Biochem Biophys Res Commun. Dec. 5, 2008;377(1):62-7. doi:10.1016/j.bbrc.2008.09.078. Epub Sep. 25, 2008.

Mund et al., LEGO-NMR spectroscopy: a method to visualize individual subunits in large heteromeric complexes. Angew Chem Int Ed Engl. Oct. 18, 2013;52(43):11401-5. doi: 10.1002/anie.201304914. Epub Aug. 14, 2013.

(56) References Cited

OTHER PUBLICATIONS

Nakane et al., A nanosensor for transmembrane capture and identification of single nucleic Acid molecules. Biophys J. Jul. 2004;87(1):615-21. Erratum in: Biophys J. Nov. 2004;87(5):3618.
Nakane et al., Nanopore sensors for nucleic acid analysis. J. Phys.: Condens. Matter, vol. 15: R 1365-R1393 (2003).
Niedzwiecki et al., Inspection of the Engineered FhuA deltaC/delta4L Protein Nanopore by Polymer Exclusion. Biophys J. Nov. 2012;103:2115-124.
Nikolaidou et al., alpha-Ketoglutarate: Biological Effects of a Novel Biomarker of Heart Failure. Heart. Sep. 2010;96(17). 2 pages.
Ogasawara et al., Determination of Reduced Nicotinamide Adenine Dinucleotid Phosphate Concentration Using High-Performance Liquid Chromatography with Fluorescence Detection: Ratio of the Reduced Form as a Biomarker of Oxidative Stress. Biol Pharm Bull. Nov. 2009;32(11):1819-18223.
Oukhaled et al., Dynamics of Completely Unfolded and Native Proteins through Solid-State Nanopores as a Function of Electric Driving Force. Am Chem Soc. Apr. 8, 2011;5(5):3628-38.
Pavlenok et al., Hetero-oligomeric MspA pores in *Mycobacterium smegmatis*. FEMS Microbiol Lett. Apr. 2016;363(7). pii: fnw046. doi:10.1093/femsle/fnw046. Epub Feb. 23, 2016.
Pavlenok et al., MspA nanopores from subunit dimers. PLoS One. 2012;7(6):e38726. doi: 10.1371/journal.pone.0038726. Epub Jun. 18, 2012.
Pfeiffer et al., Bivalent cholesterol-based coupling of oligonucletides to lipid membrane assemblies. J Am Chem Soc. Aug. 25, 2004;126(33):10224-5.
Plesa et al., Fast Translocation of Proteins through Solid State Nanopores. Nano Lett. Jan. 23, 2013:13:658-663.
Purnell et al., Nucleotide identification and orientation discrimination of DNA homopolymers immobilized in a protein nanopore. Nano Lett. Sep. 2008;8(9):3029-34. doi: 10.1021/nl802312f. Epub Aug. 13, 2008.
Quick et al., A reference Bacterial Genome Dataset Generated on the MinION Portable Single-Molecule Nanopore Sequencer. GigaScience. 2014;3(22):1-6.
Rajagopalan et al., Interaction of Dihydrofolate Reductase with Methotrexate: Ensemble and Single-Molecule Kinetics. PNAS. Oct. 15, 2002;99(21):13481-6.
Rasko et al., The pangenome structure of *Escherichia coli*: comparative genomic analysis of *E. coli* commensal and pathogenic isolates. J Bacteriol. Oct. 2008;190(20):6881-93. doi:10.1128/Jb.00619-08. Epub Aug. 1, 2008.
Rhee et al., Nanopore sequencing technology: research trends and applications. Trends Biotechnol. Dec. 2006;24(12):580-6. Epub Oct. 19, 2006.
Robinson et al., Secretion of curli fibre subunits is mediated by the outer membrane-localized CsgG protein. Mol Microbiol. Feb. 2006;59(3):870-81.
Rodriguez-Gallego et al., Mapping of the Circulating Metabolome Reveals alpha-Ketoglutarate as a Predictor of Morbid Obesity-Associated Non-Alcoholic Fatty Liver Disease. Int J of Obesity. 2015;39:279-287.
Rotem et al., Protein detection by nanopores equipped with aptamers. J Am Chem Soc. Feb. 8, 2012;134(5):2781-7. doi:10.1021/ja2105653. Epub Jan. 26, 2012.
Russo et al., Reversible permeabilization of plasma membranes with an engineered switchable pore. Nat Biotechnol. Mar. 1997;15(3):278-82.
Saariaho et al., Characteristics of MuA transposase-catalyzed processing of model transposon ends and DNA hairpin substrates. Nucleic Acids Res. Jun. 6, 2006;34(10):3139-49.
Sanchez-Quesada et al., Cyclic Peptides as Molecular Adapters for a Pore-Forming Protein. Journal American Chemical Society, vol. 122(48):11757-11766 (2000).
Sanchez-Quesada et al., Single DNA rotaxanes of a transmembrane pore protein. Angew Chem Int Ed Engl. Jun. 7, 2004;43(23):3063-7.
Sanderson, Personal genomes: Standard and pores. Nature. Nov. 6, 2008;456(7218):23-5. doi: 10.1038/456023a.

Sauer-Budge et al., Unzipping kinetics of double-stranded DNA in a nanopore. Phys Rev Lett. Jun. 13, 2003;90(23):238101. Epub Jun. 9, 2003.
Smeets et al., Salt dependence of ion transport and DNA translocation through solid-state nanopores. Nano Lett. Jan. 2006;6(1):89-95.
Soni et al., Synchronous optical and electrical detection of biomolecules traversing through solid-state nanopores. Rev Sci Instrum. Jan. 2010;81(1):014301. doi: 10.1063/1.3277116.
Soskine et al., An engineered ClyA nanopore detects folded target proteins by selective external association and pore entry. Nano Lett. Sep. 12, 2012;12(9):4895-900. doi:10.1021/nl3024438. Epub Aug. 6, 2012.
Soskine et al., Single-Molecule Analyte Recognition with ClyA Nanopores Equipped with Internal Protein Adaptors. J Am Chem Soc. 2015;137:5793-97.
Soskine et al., Tuning the size and properties of ClyA nanopores assisted by directed evolution. J Am Chem Soc. Sep. 11, 2013;135(36):13456-63. doi: 10.1021/ja4053398. Epub Aug. 27, 2013.
Stoddart et al., Multiple base-recognition sites in a biological nanopore: two heads are better than one. Angew Chem Int Ed Engl. 2010;49(3):556-9. doi: 10.1002/anie.200905483.
Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.
Sutherland et al., An analysis of mismatched duplex DNA unzipping through a bacterial nanopore. Biochem Cell Biol. Jun. 2004;82(3):407-12.
Taylor et al., Atomic resolution insights into curli fiber biogenesis. Structure. Sep. 7, 2011;19(9):1307-16. doi: 10.1016/j.str.2011.05.015.
Trewick et al., Oxidative Demethylation by *Escherichia coli* AlkB Directly Reverts DNA Base Damage. Nature. Sep. 12, 2002:419:174-78.
Van De Goor, Nanopore Detection: Threading DNA Through a Tiny Hole. PharmaGenomics, vol. 4 (3):28-30 (2004).
Van Gerven et al., Secretion and functional display of fusion proteins through the curlibiogenesis pathway. Mol Microbiol. Mar. 2014;91(5):1022-35. doi:10.1111/mmi.12515. Epub Feb. 12, 2014.
Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f.
Van Meervelt et al., Detection of Two Isomeric Binding Configurations in a Protein-Aptamer Complex with a Biological Nanopore. Am Chem Soc. Dec. 10, 2014;8(12):12826-35.
Van Meervelt et al., Real-Time Conformational Changes and Controlled Orientation of Native Proteins Inside a Protein Nanoreactor. J Am Chem Soc. Dec. 27, 2017; 139(51): 18640-18646. EPub Dec. 5, 2017. doi: 10.1021/jacs.7b10106.
Walker et al., Key residues for membrane binding, oligomerization, and pore forming activity of staphylococcal alpha-hemolysin identified by cysteine scanning mutagenesis and targeted chemical modification. J Biol Chem. Sep. 29, 1995;270(39):23065-71.
Wallace et al., *E. coli* hemolysin E (HlyE, ClyA, SheA): X-ray crystal structure of the toxin and observation of membrane pores by electron microscopy. Cell. Jan. 21, 2000;100(2):265-76.
Wang et al., Nanopores with a spark for single-molecule detection. Nat Biotechnol. Jul. 2001;19(7):622-3.
Wanunu et al., DNA translocation governed by interactions with solid-state nanopores. Biophys J. Nov. 15, 2008;95(10):4716-25. doi: 10.1529/biophysj.108.140475. Epub Aug. 15, 2008.
Wanunu, Nanopores: A journey towards DNA sequencing. Phys Life Rev. Jun. 2012;9(2):125-58. doi:10.1016/j.plrev.2012.05.010. Epub May 18, 2012.
Welford et al., The Selectivity and Inhibition 21;278(12):10157-161. of AlkB. J. Biol. Chem. Mar. 21, 2003;278(12):10157-161.
Wendell et al., Translocation of double-stranded DNA through membrane-adapted phi29 motor protein nanopores. Nat Nanotechnol. 2009;4(11):765-772. doi:10.1038/nnano.2009.259.

(56) References Cited

OTHER PUBLICATIONS

White et al., Single Ion-Channel Recordings Using Glass Nanopore Membranes. J Am Chem Soc. 2007;129:11766-775.
Wolfe et al., Catalyzing the translocation of polypeptides through attractive interactions. J Am Chem Soc. Nov. 14, 2007;129(45):14034-41. Epub Oct. 19, 2007.
Wong et al., Polymer capture by electro-osmotic flow of oppositely charged nanopores. J Chem Phys. Apr. 28, 2007;126(16):164903.
Wu et al., Protein nanopores with covalently attached molecular adapters. J Am Chem Soc. Dec. 26, 2007;129(51):16142-8. Epub Nov. 30, 2007.
Yoo et al., Glucose Biosensors: An Overview of Use in Clinical Practice. Sensores. May 4, 2010;10:4558-4576.
Zernia et al., Current Blockades of Proteins inside Nanopores for Real-Time Metabolome Analysis. ACS Nano. Feb. 25, 2020; 14(2): 2296-2307. EPub Jan. 31, 2020. doi: 10.1021/acsnano.9b09434.
Zhou et al., Ion Channel Probes for Scanning Ion Conductance Microscopy. Langmuir. Nov. 25, 2014;30:15351-355.
U.S. Appl. No. 16/858,859, filed Apr. 27, 2020, Stoddart et al.
[No Author Listed] Enterobacteria phage vB_EcoM-ACG-C40, complete genome. Genbank Acc. No. NC 019399.1. 2 pages.
[No Author Listed], *Escherichia coli* HS curli production assembly/transport subunit. Accession No. ABV05494. Sep. 11, 2007. 2 pages.
Eifler et al., Cytotoxin ClyA from *Escherichia coli* assembles to a 13-meric pore independent of its redox-state. EMBO J. Jun. 7, 2006;25(11):2652-61. doi: 10.1038/sj.emboj.7601130. Epub May 11, 2006.
Mueller et al., RCSB Protein Data Bank No. 2WCD. Mar. 11, 2009. doi: 10.2210/pdb2WCD/pdb. 5 pages.
Rucker et al., Recombinant ferritin: modulation of subunit stoichiometry in bacterial expression systems. Protein Eng. 1997;10(8):967-973. doi:10.1093/protein/10.8.967.
Zernia et al., Current Blockades of Proteins inside Nanopores for Real-Time Metabolome Analysis. ACS Nano. Feb. 25, 2020; 14(Supplemental Information). EPub Jan. 31, 2020. doi: 10.1021/acsnano.9b09434. 19 pages.

\* cited by examiner

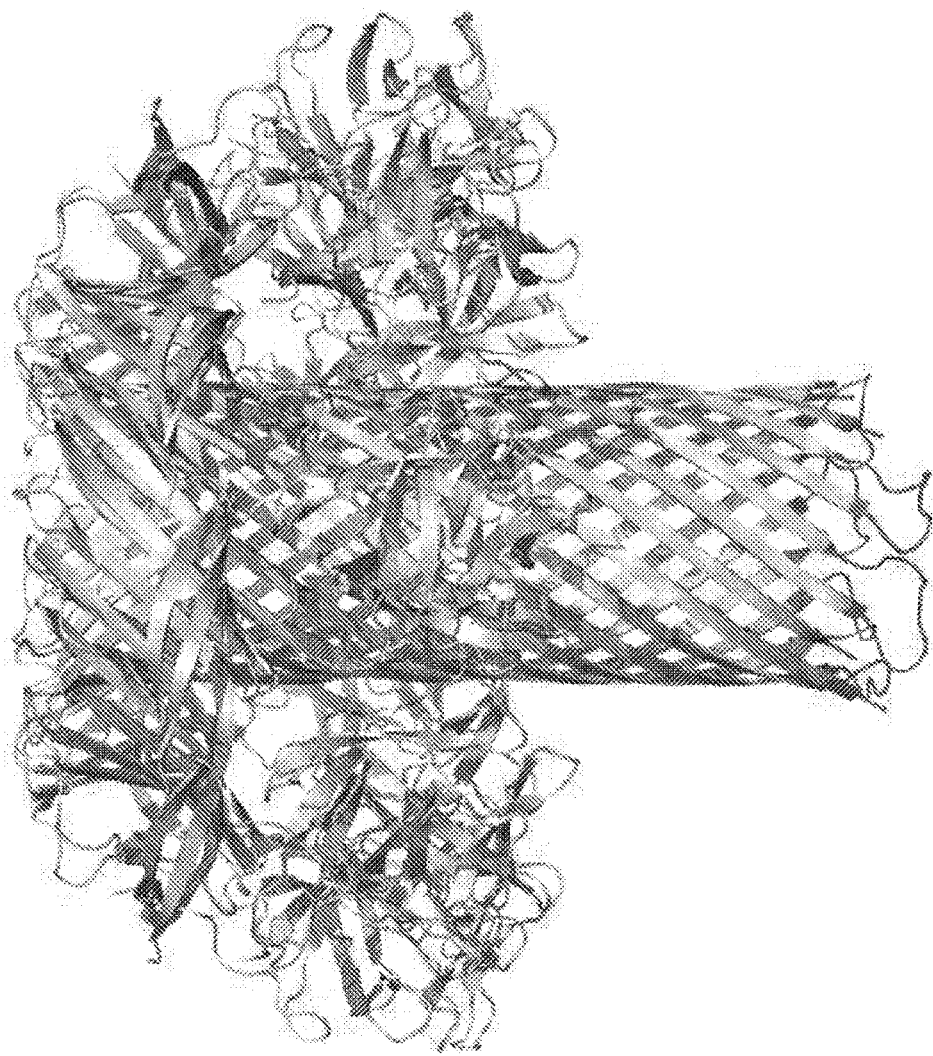
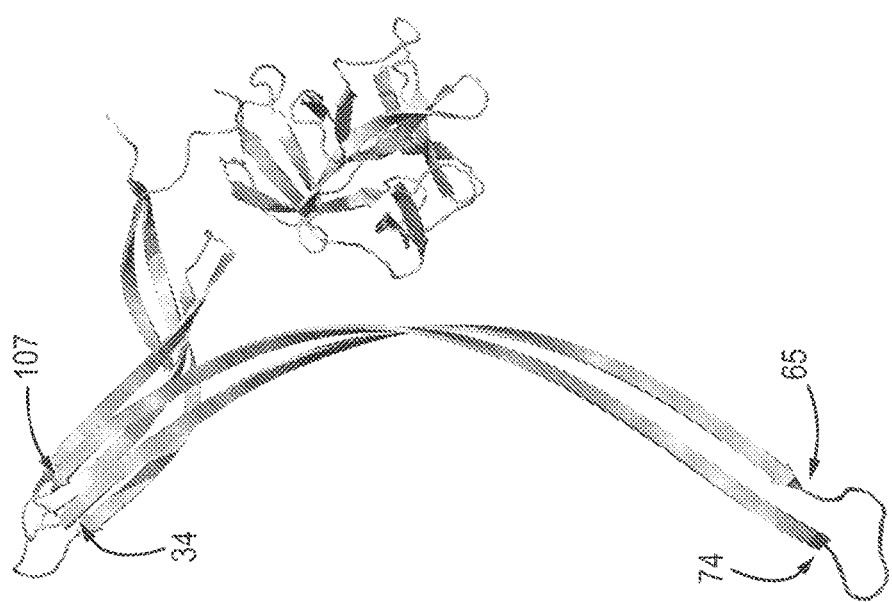

Fig. 8

```
Lysenin    1M---SAKA----AEGYEQIEVDVVAVWKEGYVENRGSTSVDQKITLITKGMKNVNSETRVVTATHSIGSTIISTGDAFEIGSVEVSYSHSHEEBQVSMTETEVYESKVIE  102
LRP2       1M---SSRAGIAEGVEQIEVDVVAVWKEGYVENRGSTSVDQKIKITKGMRNLNSETKILTASHSIGSTIISTGDLFEIATYDVSYSVSFSHEESQVSMTETEVYESSKEIE  104
LRP3       1MSATA/T---ADGIEEIEVDVVAVWKEGYVENRGDTSVEQKITMTKGMKNLNSETKIILATHPVGRILKVGDPFEIGSVEVSYSFSHQESQVSMTQTEVYSSQVIE     104
LRP1       1MSSSTVM---ADGFEEIEVDVVSVWKEGYAIENRGNSSVQQKITMTKGMKNLNSETKILTATHTLGRILKVGDPFEIASVEVSYTFSHQKSQVSMTQTEVYSSQVIE    104

Lysenin   103HTITIIPPTSKFTRWQLNADVGGADIEYMYLIDEVTPIGGTOSIPQVITSRAKIIVGRQIILGKIETRIKHAERKEYMTVVSRKSWPAATLGHSKLFKFVLMEDWGg   208
LRP2      105HTITIIPPTSKFTRWQLNADVGGADIEYMYLIDEVTPIGGMLSIPQVIKSRAKIIVGREIYLGETEIRIKHADRKEYMTVSRKSWPAATLGHSKLYKFVLYEDMYG    210
LRP3      105HTVTIIPPTSKFTRWKLNADVGGTIDIEYMYLIDEVTPISVTQTIPQVIRSRAKIDVGRQIHLGTTAVRIKHAERQEYMTVIERKKWPAATIGKSNLFKFVLEDSSG   210
LRP1      105HTVTIIPPNKKFTRWKLNADVGGTGIEYMYLIDEVTATGADLIFEVMNKSRAKILVGRQIHLGETEIRIKHAERKEYMTVISRKSWPAATIGNSNLFKFVLFEDSSG   210

Lysenin   209FRIKTLNTMYSGYEYAYSSDQgGEYEDQGTDNPKQRWAINKSLPLRHGDVVTFMNKYETRSSGLCYDDGPATNVYCLDKREDKWILEVVg---                  297
LRP2      211FRIKTLNTMYSGYEYAYSSDQGGLYEDQGSDNPKQRWAINKSLPLRHGDVVTFMNKYFTRSSGLCYDDGPATDVYCLDKREDKWILEVV---KP               300
LRP3      211TRIKTLNTMYPGYEWAYSSDQGGVIDESSDNPKQRWALSKALPLRHGDVVTFMRKYFTTNSSGLCVDDGPATNVYFTNNSSGMCVDDGPATNVYCLDKREDKWILEVV---NP  300
LRP1      211TRIKTLNTMYPGYEWAYSSDQGGIFDESSDNPKQRWALSKAMPLRHGDVVTFRNNFTTNSSGMCVDDGPATNVYCLEKREDKWILEVV---NT               300
```

MUTANT PORE

RELATED APPLICATIONS

This application is a national stage filing under 35 U.S.C. § 371 of international application number PCT/GB2017/050961, filed Apr. 6, 2017, which claims foreign priority under 35 U.S.C. § 119(a)-(d) or 35 U.S.C. § 365(b) to British application number GB 1605899.2, filed Apr. 6, 2016 and GB application number 1608274.5, filed May 11, 2016, the entire contents of each of which are incorporated herein by reference.

FIELD OF THE INVENTION

The invention relates to mutant forms of lysenin. The invention also relates to analyte characterisation using the mutant forms of lysenin.

BACKGROUND TO THE INVENTION

Nanopore sensing is an approach to sensing that relies on the observation of individual binding or interaction events between analyte molecules and a receptor. Nanopore sensors can be created by placing a single pore of nanometer dimensions in an insulating membrane and measuring voltage-driven ionic transport through the pore in the presence of analyte molecules. The identity of an analyte is revealed through its distinctive current signature, notably the duration and extent of current block and the variance of current levels. Such nanopore sensors are commercially available, for example the MinION™ device sold by Oxford Nanopore Technologies Ltd, comprising an array of nanopores integrated within an electronic chip.

There is currently a need for rapid and cheap nucleic acid (e.g. DNA or RNA) sequencing technologies across a wide range of applications. Existing technologies are slow and expensive mainly because they rely on amplification techniques to produce large volumes of nucleic acid and require a high quantity of specialist fluorescent chemicals for signal detection. Nanopore sensing has the potential to provide rapid and cheap nucleic acid sequencing by reducing the quantity of nucleotide and reagents required.

One of the essential components of sequencing nucleic acids using nanopore sensing is the control of nucleic acid movement through the pore. Another is the discrimination of nucleotides as the nucleic acid polymer is moved through the pore. In the past, to achieve nucleotide discrimination the nucleic acid has been passed through a mutant of hemolysin. This has provided current signatures that have been shown to be sequence dependent. It has also been shown that a large number of nucleotides contribute to the observed current when a hemolysin pore is used, making a direct relationship between observed current and polynucleotide challenging.

While the current range for nucleotide discrimination has been improved through mutation of the hemolysin pore, a sequencing system would have higher performance if the current differences between nucleotides could be improved further. In addition, it has been observed that when the nucleic acids are moved through a pore, some current states show high variance. It has also been shown that some mutant hemolysin pores exhibit higher variance than others. While the variance of these states may contain sequence specific information, it is desirable to produce pores that have low variance to simplify the system. It is also desirable to reduce the number of nucleotides that contribute to the observed current.

Lysenin (also known as efL1) is a pore-forming toxin purified from the coelomic fluid of the earthworm *Eisenia fetida*. It specifically binds to sphingomyelin, which inhibits lysenin-induced hemolysis (Yamaji et al., J. Biol. Chem. 1998; 273(9): 5300-6). The crystal structure of a lysenin monomer is disclosed in De Colbis et al., Structure, 2012; 20: 1498-1507.

SUMMARY OF THE INVENTION

The inventors have surprisingly identified new mutant lysenin monomers in which one or more modifications have been made to improve the ability of the monomer to interact with a polynucleotide. The inventors have also surprisingly demonstrated that pores comprising the novel mutant monomers have an enhanced ability to interact with polynucleotides and therefore display improved properties for estimating the characteristics of, such as the sequence of, polynucleotides. The mutant pores surprisingly display improved nucleotide discrimination. In particular, the mutant pores surprisingly display an increased current range, which makes it easier to discriminate between different nucleotides, and a reduced variance of states, which increases the signal-to-noise ratio. In addition, the number of nucleotides contributing to the current as the polynucleotide moves through the pore is decreased. This makes it easier to identify a direct relationship between the observed current as the polynucleotide moves through the pore and the polynucleotide.

All amino acid substitutions, deletions and/or additions disclosed herein are with reference to a mutant lysenin monomer comprising a variant of the sequence shown in SEQ ID NO: 2, unless stated to the contrary.

Reference to a mutant lysenin monomer comprising a variant of the sequence shown in SEQ ID NO: 2 encompasses mutant lysenin monomers comprising variants of sequences as set out in SEQ ID NOS: 14 to 16. Amino acid substitutions, deletions and/or additions may be made to lysenin monomers comprising a variant of the sequence shown in SEQ ID NO: 2 that are equivalent to the substitutions, deletions and/or additions disclosed herein with reference to SEQ ID NO: 2.

A mutant monomer may be considered as an isolated monomer.

Accordingly, the invention provides a mutant lysenin monomer comprising a variant of the sequence shown in SEQ ID NO: 2, wherein the monomer is capable of forming a pore and wherein the variant comprises a modification at one or more of the following positions K37, G43, K45, V47, S49, T51, H83, V88, T91, T93, V95, Y96, S98, K99, V100, I101, P108, P109, T110, S111, K112 and T114.

The invention also provides a mutant lysenin monomer comprising a variant of the sequence shown in SEQ ID NO: 2, wherein the monomer is capable of forming a pore and wherein the variant comprises one or more of the substitutions D35N/S;
S74K/R;
E76D/N;
S78R/K/N/Q;
S80K/R/N/Q;
S82K/R/N/Q;
E84R/K/N/A;
E85N;
S86K/Q;
S89K;
M90K/I/A;

E92D/S;
E94D/Q/G/A/K/R/S/N;
E102N/Q/D/S;
T104R/K/Q;
T106R/K/Q;
R115S;
Q117S; and
N119S.

The invention also provides a mutant lysenin monomer comprising a variant of the sequence shown in SEQ ID NO: 2, wherein the monomer is capable of forming a pore and wherein the variant comprises mutations at one or more of
D35/E94/T106;
K37/E94/E102/T106;
K37/E94/T104/T106;
K37/E94/T106;
K37/E94/E102/T106;
G43/E94/T106;
K45/V47/E92/E94/T106;
K45/V47/E94/T106;
K45/S49/E92/E94/T106;
K45/S49/E94/T106;
K45/E94/T106;
K45/T106;
V47/E94/T106;
V47/V88/E94/T106;
S49/E94/T106;
T51/E94D/T106;
S74/E94;
E76/E94;
S78/E94;
Y79/E94;
580/E94;
S82/E94;
S82/E94/T106;
H83/E94;
H83/E94/T106;
E85/E94/T106;
S86/E94;
V88/M90/E94/T106;
S89/E94;
M90/E94/T106;
T91/E94/T106;
E92/E94/T106;
T93/E94/T106;
E94/Y96/T106;
E94/S98/K99/T106;
E94/K99/T106;
E94/E102;
E94/T104;
E94/T106;
E94/P108;
E94/P109;
E94/T110;
E94/S111;
E94/T114;
E94/R115;
E94/Q117; and
E94/E119.

The invention also provides a mutant lysenin monomer comprising a variant of the sequence shown in SEQ ID NO: 2, wherein the monomer is capable of forming a pore and wherein the variant comprises one or more of the substitutions:
E84R/E94D;
E84K/E94D;
E84N/E94D;
E84A/E94Q;
E84K/E94Q and
E94Q/D121S.

The invention also provides a mutant lysenin monomer comprising a variant of the sequence shown in SEQ ID NO: 2, wherein the variant comprises one of the following combinations of substitutions:
E84Q/E85K/E92Q/E94D/E97S/D126G;
E84Q/E85K/E92Q/E94Q/E97S/D126G; or
E84Q/E85K/E92Q/E94D/E97S/T106K/D126G.

The invention also provides a mutant lysenin monomer comprising a variant of the sequence shown in SEQ ID NO: 2, wherein in the variant (a) 2, 4, 6, 8, 10, 12, 14, 16, 18 or 20 of the amino acids at positions 34 to 70 of SEQ ID NO: 2, or corresponding to those positions, have been deleted and (b) 2, 4, 6, 8, 10, 12, 14, 16, 18 or 20 of the amino acids at positions 71 to 107 of SEQ ID NO: 2, or corresponding to those positions, have been deleted.

The invention also provides:
a construct comprising two or more covalently attached monomers derived from lysenin, wherein at least one of the monomers is a mutant lysenin monomer of the invention;
a polynucleotide which encodes a mutant lysenin monomer of the invention or a genetically fused construct of the invention;
a homo-oligomeric pore derived from lysenin comprising a sufficient number of mutant lysenin monomers of the invention;
a hetero-oligomeric pore derived from lysenin comprising at least one mutant lysenin monomer of the invention;
a pore comprising at least one construct of the invention;
a method of characterising a target analyte, comprising: (a) contacting the target analyte with a pore of the invention such that the target analyte moves through the pore; and (b) taking one or more measurements as the analyte moves with respect to the pore wherein the measurements are indicative of one or more characteristics of the target analyte and thereby characterising the target analyte;
a method of forming a sensor for characterising a target polynucleotide, comprising forming a complex between a pore of the invention and a polynucleotide binding protein and thereby forming a sensor for characterising the target polynucleotide;
a sensor for characterising a target polynucleotide, comprising a complex between a pore of the invention and a polynucleotide binding protein;
use of a pore of the invention to characterise a target analyte;
a kit for characterising a target polynucleotide comprising (a) a pore of the invention and (b) a membrane;
an apparatus for characterising target polynucleotides in a sample, comprising (a) a plurality of pores of the invention and (b) a plurality of polynucleotide binding proteins;
a method of improving the ability of a lysenin monomer comprising the sequence shown in SEQ ID NO: 2 to characterise a polynucleotide, comprising making one or more modifications and/or substitutions of the invention;
a method of producing a construct of the invention, comprising covalently attaching at least one mutant lysenin monomer of the invention to one or more monomers derived from lysenin; and
a method of forming a pore of the invention, comprising allowing at least one mutant monomer of the invention or at least one construct of the invention to oligomerise with a sufficient number of monomers of the invention, constructs of the invention or monomers derived from lysenin to form a pore.

DESCRIPTION OF THE FIGURES

FIG. 7 depicts regions of the lysenin pore.
FIG. 7A shows the 3D structure of a nonomeric pore of lysenin and FIG. 7B shows the structure of a monomer taken from the lysenin pore. Each monomer contributes two beta sheets to the barrel of lysenin pore. The beta sheets (containing amino acids corresponding to amino acids 34-64 and 75-107 of SEQ ID NO: 2) are linked by an unstructured loop at the bottom of the pore (amino acids corresponding to position 65-74 of SEQ ID NO: 2).
FIG. 8 is an alignment of the amino acid sequence of lysenin (SEQ ID NO: 2) with the amino acid sequences of three lysenin related proteins (SEQ ID NOs: 14-16). The three lysenin homologues having sequences closely related to lysenin were identified by performing a BLAST search using a database of non-redundant protein sequences. The protein sequences of lysenin related protein 1 (LRP1), lysenin related protein 2 (LRP2) and lysenin related protein 3 (LRP3) were aligned with the sequence of lysenin to show similarities of the four proteins. The dark grey shading indicates positions at which identical amino acids are present in all four sequences. LRP1 is approximately 75% identical to lysenin, LRP2 is approximately 88% identical to lysenin and LRP3 is approximately 79% identical to lysenin.

DESCRIPTION OF THE SEQUENCE LISTING

Figure 1:
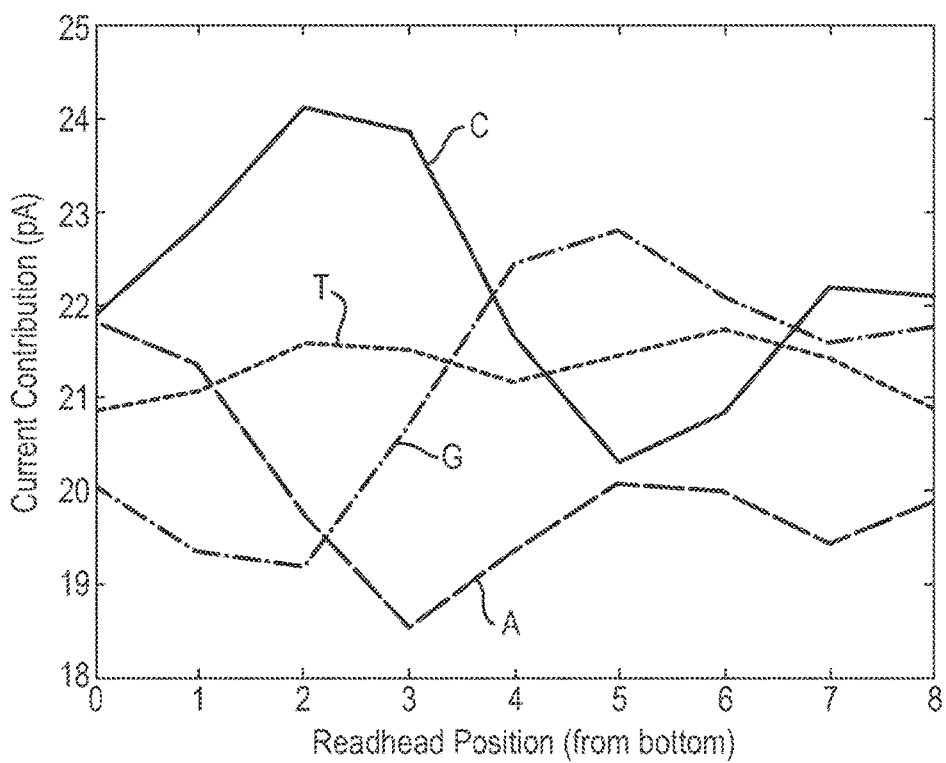
FIG. 1 shows the median plot for lysenin mutant 1.

SEQ ID NO: 1 shows the polynucleotide sequence encoding the lysenin monomer.
SEQ ID NO: 2 shows the amino acid sequence of the lysenin monomer.
SEQ ID NO: 3 shows the polynucleotide sequence encoding the Phi29 DNA polymerase.
SEQ ID NO: 4 shows the amino acid sequence of the Phi29 DNA polymerase.
SEQ ID NO: 5 shows the codon optimised polynucleotide sequence derived from the sbcB gene from E. coli. It encodes the exonuclease I enzyme (EcoExo I) from E. coli.
SEQ ID NO: 6 shows the amino acid sequence of exonuclease I enzyme (EcoExo I) from E. coli.
SEQ ID NO: 7 shows the codon optimised polynucleotide sequence derived from the xthA gene from E. coli. It encodes the exonuclease III enzyme from E. coli.
SEQ ID NO: 8 shows the amino acid sequence of the exonuclease III enzyme from E. coli. This enzyme performs distributive digestion of 5' monophosphate nucleosides from one strand of double stranded DNA (dsDNA) in a 3'-5' direction. Enzyme initiation on a strand requires a 5' overhang of approximately 4 nucleotides.
SEQ ID NO: 9 shows the codon optimised polynucleotide sequence derived from the recJ gene from T. thermophilus. It encodes the RecJ enzyme from T. thermophilus (TthRecJ-cd).
SEQ ID NO: 10 shows the amino acid sequence of the RecJ enzyme from T. thermophilus (TthRecJ-cd). This enzyme performs processive digestion of 5' monophosphate nucleosides from ssDNA in a 5'-3' direction. Enzyme initiation on a strand requires at least 4 nucleotides.
SEQ ID NO: 11 shows the codon optimised polynucleotide sequence derived from the bacteriophage lambda exo (redX) gene. It encodes the bacteriophage lambda exonuclease. SEQ ID NO: 12 shows the amino acid sequence of the bacteriophage lambda exonuclease. The sequence is one of three identical subunits that assemble into a trimer. The enzyme performs highly processive digestion of nucleotides from one strand of dsDNA, in a 5'-3'direction (www.neb-.com/nebecomm/products/productM0262.asp). Enzyme initiation on a strand preferentially requires a 5' overhang of approximately 4 nucleotides with a 5' phosphate.
SEQ ID NO: 13 shows the amino acid sequence of He1308 Mbu.
SEQ ID NO: 14 shows the amino acid sequence of lysenin related protein (LRP) 1.
SEQ ID NO: 15 shows the amino acid sequence of lysenin related protein (LRP) 2.
SEQ ID NO: 16 shows the amino acid sequence of lysenin related protein (LRP) 3.
SEQ ID NO: 17 shows the amino acid sequence of the activated version of parasporin-2. The full length protein is cleaved at its amino and carboxy termini to form an activated version that is capable of forming pores.
SEQ ID NO: 18 shows the amino acid sequence of Dda 1993.
SEQ ID NOs: 19 to 24 show the polynucleotide sequences used in the examples.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a mutant monomer" includes "mutant monomers", reference to "a substitution" includes two or more such substitutions, reference to "a pore" includes two or more such pores, reference to "a polynucleotide" includes two or more such polynucleotides, and the like.

In this specification, where different amino acids at a specific positon are separated by the symbol "/", the/symbol "I" means "or". For instance, P108R/K means P108R or P108K. In this specification where different positions or different substitutions are separated by the the symbol "/", the "I" symbol means "and". For example, E94/P108 means E94 and P108 or E94D/P108K means E94D and P108K.

All publications, patents and patent applications cited herein, whether supra or infra, are hereby incorporated by reference in their entirety.

Mutant Lysenin Monomers

In one aspect, the present invention provides mutant lysenin monomers. The mutant lysenin monomers may be used to form the pores of the invention. A mutant lysenin monomer is a monomer whose sequence varies from that of a wild-type lysenin monomer (e.g. SEQ ID NO: 2, SEQ ID NO: 14, SEQ ID NO: 15 or SEQ ID NO: 16). The mutant lysenin monomer typically retains the ability to form a pore in the presence of other monomers of the invention or other monomers from lysenin or derived from lysenin. The mutant monomer is therefore typically capable of forming a pore. Methods for confirming the ability of mutant monomers to form pores are well-known in the art and are described in the Examples. For example, the formation of pores by be determined by electrophysiology. The pores are typically inserted in a membrane, which may be, for example, a lipid membrane or a block co-polymer membrane. Electrical or optical measurements may be acquired from single lysenin pores, such as pores comprising one or more monomer of the invention, inserted in a membrane. A potential difference may be applied across the membrane and current flow through the membrane may be detected. Current flow may be detected by any suitable method, such as by electrical or optical means. The ability of the pore to translocate polynucleotides, preferably single stranded polynucleotides, may be determined by adding a polynucleotide binding protein, DNA, fuel (e.g MgCl2, ATP) pre-mix, applying a potential difference (of, for example 180 mV) and monitoring current flow through the pore to detect polynucleotide binding protein-controlled DNA movement.

The mutant monomers have an altered ability to interact with a polynucleotide when present in a pore. Pores comprising one or more of the mutant monomers therefore have improved nucleotide reading properties e.g. display (1) improved polynucleotide capture and (2) improved polynucleotide recognition or discrimination. In particular, pores constructed from the mutant monomers capture nucleotides and polynucleotides more easily than the wild type. In addition, pores constructed from the mutant monomers display an increased current range, which makes it easier to discriminate between different nucleotides, and a reduced variance of states, which increases the signal-to-noise ratio. In addition, the number of nucleotides contributing to the current as the polynucleotide moves through pores constructed from the mutants is decreased. This makes it easier to identify a direct relationship between the observed current as the polynucleotide moves through the pore and the polynucleotide. The improved nucleotide reading properties of the mutants are achieved via five main mechanisms, namely by changes in the:

sterics (increasing or decreasing the size of amino acid residues);
charge (e.g. introducing or removing −ve charge and/or introducing or removing +ve charge);
hydrogen bonding (e.g. introducing amino acids that can hydrogen bond to the base pairs);
pi stacking (e.g. introducing amino acids that interact through delocalised electron pi systems); and/or
alteration of the structure of the pore (e.g. introducing amino acids that increase the size of the barrel or channel).

Any one or more of these five mechanisms may be responsible for the improved properties of the pores formed from the mutant monomers of the invention. For instance, a pore comprising a mutant monomer of the invention may display improved nucleotide reading properties as a result of altered sterics, altered hydrogen bonding and an altered structure.

A mutant monomer of the invention comprises a variant of the sequence shown in SEQ ID NO: 2. SEQ ID NO: 2 is the wild-type sequence of the lysenin monomer. A variant of SEQ ID NO: 2 is a polypeptide that has an amino acid sequence which varies from that of SEQ ID NO: 2. Typically the variant retains its ability to form a pore.

Pores comprising one or more of the mutant monomers comprising a substitution at S80, T106, T104 display improved polynucleotide capture. Particular examples of such substitutions include S80K/R, T104R/K and T106R/K. Other substitutions at these positions which increase the positive charge of the amino acid side chain at any one or more, such as 2, 3, 4 or 5, of these positions may be used to improve the properties of a pore comprising the mutant monomer, i.e. improve capture of the polynucleotide, compared to a wild-type pore or a pore comprising a mutant monomer comprising other capture enhancing mutations such as E84Q/E85K/E92Q/E97S/D126G, for example a pore comprising a mutant monomer comprising only those mutations or a mutant monomer comprising the following mutations E84Q/E85K/E92Q/E94D/E97S/D126G. Typically, where the improvement is determined relative to a pore comprising other mutations, such as E84Q/E85K/E92Q/E97S/D126G or E84Q/E85K/E92Q/E94D/E97S/D126G, those mutations are also present in the mutant monomer being tested, i.e. the effect(s) of a mutation, or combination of mutations, is(are) determined relative to a baseline monomer/pore that is identical to the monomer/pore being tested other that at the test positions(s). The properties of a pore comprising a mutant monomer or a control monomer may be determined using heterooligomeric pores, or more preferably homooligomaric pores. Examples of preferred combinations of mutations are described throughout the specification, for example in Table 9.

Pores comprising one or more of the mutant monomers comprising a substitution at D35, K37, K45, V47, S49, E76, S78, S82, V88, S89, M90, T91, E92, E94, Y96, S98, V100, T104 display improved polynucleotide recognition or discrimination. Particular examples of such substitutions include D35N, K37N/S, K45R/K/D/T/Y/N, V47K/R, S49K/R/L, T51KE76S/N, S78N, S82N, V88I, S89Q, M90I/A, T91S, E92D/E, E94D/Q/N, Y96D, S98Q, V100S and T104K. These mutations may each decrease noise, increase current range and/or reduce channel gating as described in Table 9. Other mutations that increase or decrease the size of the amino acid side chain, increase or decrease the charge, result in the same hydrogen bond formation and/or affect pi stacking in the same way as any one or more of these exemplary mutations made be made to the specified positions in SEQ ID NO: 2 or to the corresponding position in a variant of SEQ ID NO: 2. The mutations may be introduced individually or in combination. For example, 2, 3, 4, 5, 6, 7, 8, 9, 10, 11, 12, 13, 14, 15, 16, 17 or 18 of these positions may be mutated to improve the properties of a pore comprising the mutant monomer, i.e. improve signal to noise, increase range and/or decrease channel gating such that polynucleotide recognition or discrimination is improved, compared to a wild-type pore, a pore comprising a mutant monomer comprising the mutations E84Q/E85K/E92QE97S/D126G, such as a monomer comprising only those mutations, the mutations E84Q/E85K/E92Q/E94D/E97S/D126G, the mutations E84Q/E85K/E92Q/E94Q/E97S/D126G and/or the mutations E84Q/E85K/E92Q/E94D/E97S/T106K/D126G. Typically, where the improvement is determined relative to a pore comprising other mutations, such as E84Q/E85K/E92Q/E97S/D126G, E84Q/E85K/E92Q/E94D/E97S/D126G, E84Q/E85K/E92Q/E94Q/E97S/D126G or E84Q/E85K/E92Q/E94D/E97S/T106K/D126G, those mutations are also present in the mutant monomer being tested, i.e. the effect(s) of a mutation, or combination of mutations, is(are) determined relative to a baseline monomer/pore that is identical to the monomer/pore being tested other that at the test positions(s). The properties of a pore comprising a mutant monomer or a control monomer may be determined using heterooligomeric pores, or more preferably homooligomeric pores. Examples of preferred combinations of mutations are described throughout the specification, for example in Table 9.

Pores comprising one or more of the mutant monomers comprising a substitution at E94 and/or Y96 may reduce the number of nucleotides contributing to the current as the polynucleotide moves through pore compared to a wild-type pore or a pore comprising a mutant monomer comprising the mutations E84Q/E85K/E92QE97S/D126G. For example, the substitution Y96D/E may be made, preferably in combination with E94Q/D, to reduce the size of the read head. A reduction in the number of nucleotides contributing to the current as the polynucleotide moves through pore compared to a wild-type pore or a pore comprising a mutant monomer comprising the mutations E84Q/E85K/E92QE97S/D126G may also be achieved by deleting an even number of amino acids (typically one that would be present in the lumen of the pore and an adjacent amino acid that would face away from the lumen of the pore) from each of the two beta strands of the monomer that form part of the barrel of the pore, i.e. positions corresponding to amino acids 34 to 65 and 74 to 107 of SEQ ID NO: 2, as described herein.

Modifications of the Invention

The invention provides a mutant lysenin monomer in which the amino acid sequence of the beta sheets that contribute to the structure of the barrel in a lysenin pore are modified compared to wild-type lysenin and compared to lysenin mutants disclosed in the art, for example in WO 2013//153359. The modifications of the invention are in the region of the lysenin momomer corresponding to amino acids 34 to 107 of SEQ ID NO: 2, particularly amino acids 34 to 65 and 74 to 107 of SEQ ID NO: 2. The corresponding regions of LR1, LR2 and LR3 monomers are shown in the alignment of FIG. 8.

The invention provides a mutant lysenin monomer comprising a variant of the sequence shown in SEQ ID NO: 2, wherein the monomer is capable of forming a pore and wherein the variant comprises a modification at one or more, such as from 2 to 22, 3 to 20, 4 to 15, 5 to 10, 6, 7, 8 or 9, of the following positions K37, G43, K45, V47, S49, T51, H83, V88, T91, T93, V95, Y96, 598, K99, V100, I101, P108, P109, T110, S111, K112 and T114. The variant may comprise modifications at any number and any combination of the positions. In one aspect, the modification may be a substitution, deletion or addition of an amino acid and is preferably a substitution or a deletion mutation. Preferred modifications are discussed below under the heading "Further modifications". The mutant lysenin monomer may comprise modification at other positions of SEQ ID NO: 2. For example, in addition to one or more, such as 2 to 20, 3 to 15, 4 to 10 or 6 to 8, modifications of the invention, the mutant lysenin monomer may have one or more, such as 2 to 20, 3 to 15, 4 to 10 or 6 to 8, amino acid substitutions or deletions in the sequence of SEQ ID NO: 2 that are described in the art, for example in WO 2013/153359.

The variant preferably comprises a modification at one or more of the following positions T91, V95, Y96, S98, K99, V100, I101 and K112. The variant may have modifications at any number and any combination of the positions. The modification is preferably substitution with serine (S) or glutamine (Q). The variant preferably comprises one or more of the substitutions T91S, V95S, Y96S, S98Q, K99S, V100S, I101S and K112S. The variant may comprise any number and any combination of these substitutions.

The variant preferably comprises a modification at one or more of the following positions K37, G43, K45, V47, S49, T51, H83, V88, T91, T93, Y96, S98, K99, P108, P109, T110, S111 and T114. The variant may comprise modifications at any number and any combination of the positions. The modification is preferably substitution with asparagine (N), tryptophan (W), serine (S), glutamine (Q), lysine (K), aspartic acid (D), arginine (R), threonine (T), tyrosine (Y), leucine (L) or isoleucine (I). The variant preferably comprises one or more of the substitutions K37N/W/S/Q, G43K, K45D/R/N/Q/T/Y, V47K/S/N, S49K/L, T51K, H83S/K, V88I/T, T91K, T93K, Y96D, S98K, K99Q/L, P108K/R, P109K, T110K/R, S111K and T114K. The variant preferably comprises modifications at one or more of the following positions:
E94/P108; E94D/S111K;
E94/P109; E94D/T114K;
E94/T110; H83S/E94Q;
E94/P108; E94/K99/T106;
E94D/T110R; E94/T93/T106;
E94/T91/T106; K45/V47/E94/T106;
H83/E94/T106; V47/E94/T106;
E94/Y96/T106; T51/E94/T106;
K45/E94/T106; K45/S49/E94/T106;
K45/E94/T106; S49/E94/T106;
E94/S98/K99/T106; K45/T106;
K37/E94/T106; V47/E94/T106;
K37/E94/T106; G43/E94/T106;
K37/E94/T106; V88/M90/E94/T106;
K45/E94/T106; V47/V88/E94/T106;
K37/E94/E102/T106; K45/S49/E94/E92/T106;
K37/E94/E102/T106; K45/V47/E92/E94/T106; and
K37/E94/T104/T106; E94/K99/T106.
K45/E94/T106;

The variant preferably comprises one or more of the substitutions:
E94D/P108K; K45N/E94N/T106K;
E94D/P109K; K37Q/E94D/E102N/T106K;
E94D/T110K; K37S/E94D/E102S/T106K;

E94D/P108R; E94D/T110R; E94D/S111K; E94D/T114K; H83S/E94Q; E94D/K99Q/T106K; E94D/T93K/T106K; E94D/T91K/T106K; H83K/E94D/T106K; E94Q/Y96D/T106K; K45D/E94K/T106K; K45R/E94D/T106K; E94D/S98K/K99L/T106K; K37

V47/E94/T106;
V47/V88/E94/T106;
S49/E94/T106;
T51/E94D/T106;
S74/E94;
E76/E94;
S78/E94;
Y79/E94;
S80/E94;
S82/E94;
S82/E94/T106;
H83/E94;
H83/E94/T106;
E85/E94/T106;
S86/E94;
V88/M90/E94/T106;
S89/E94;
M90/E94/T106;
T91/E94/T106;
E92/E94/T106;
T93/E94/T106;
E94/Y96/T106;
E94/S98/K99/T106;
E94/K99/T106;
E94/E102;
E94/T104;
E94/T106;
E94/P108;
E94/P109;
E94/T110;
E94/S111;
E94/T114;
E94/R115;
E94/Q117; and
E94/E119.

The variant preferably comprises one or more of substitutions:
D35N/E94D/T106K;
D35S/E94D/T106K;
K37Q/E94D/E102N/T106K;
K37S/E94D/E102S/T106K;
K37S/E94D/T104K/T106K;
K37N/E94D/T106K;
K37W/E94D/T106K;
K37S/E94D/T106K;
G43K/E94D/T106K;
K45N/V47K/E92D/E94N/T106K;
K45T/V47K/E94D/T106K;
K45N/S49K/E94N/E92D/T106K;
K45Y/S49K/E94D/T106K;
K45D/E94K/T106K;
K45R/E94D/T106K;
K45N/E94N/T106K;
K45Q/E94Q/T106K;
K45R/T106K;
V47S/E94D/T106K;
V47K/E94D/T106K;
V47N/V88T/E94D/T106K;
S49L/E94D/T106K;
T51K/E94D/T106K;
S74K/E94D;
S74R/E94D;
E76D/E94D;
E76N/E94D;
E76S/E94Q;
E76N/E94Q;
S78R/E94D;
S78K/E94D;
S78N/E94D;
S78Q/E94Q;
Y79S/E94Q;
S80K/E94D;
S80R/E94D;
S80N/E94D;
S80Q/E94Q;
S82K/E94D;
S82R/E94D;
S82N/E94D;
S82Q/E94Q;
S82K/E94D/T106K;
H83S/E94Q;
H83K/E94D/T106K;
E85N/E94D/T106K;
S86K/E94D;
V88I/M90A/E94D/T106K;
S89K/E94D;
M90K/E94D/T106K;
M90I/E94D/T106K;
T91K/E94D/T106K;
E92D/E94Q/T106K;
T93K/E94D/T106K;
E94Q/Y96D/T106K;
E94D/S98K/K99L/T106K;
E94D/K99Q/T106K;
E94D/E102N;
E94D/E102Q;
E94D/E102D;
E94D/T104R;
E94D/T104K;
E94Q/T104Q;
E94D/T106R;
E94D/T106K;
E94Q/T106Q;
E94Q/T106K;
E94D/P108K;
E94D/P108R;
E94D/P109K;
E94D/T110K;
E94D/T110R;
E94D/S111K;
E94D/T114K;
E94Q/R115S;
E94Q/Q117S; and
E94Q/N119S.

The variant may comprise any number and any combination of these substitutions.

The invention also provides a mutant lysenin monomer comprising a variant of the sequence shown in SEQ ID NO: 2, wherein the monomer is capable of forming a pore and wherein the variant comprises one or more of the substitutions
E84R/E94D;
E84K/E94D;
E84N/E94D;
E84A/E94Q;
E84K/E94Q and
E94Q/D121S.

The variant may comprise any number and any combination of these substitutions.

The mutant monomer of the invention preferably comprises any combination of the modifications and/or substitutions defined above. Exemplary combinations are disclosed in the Examples.

Barrel Deletions

In another embodiment, the invention also provides a mutant lysenin monomer comprising a variant of the sequence shown in SEQ ID NO: 2, wherein in the variant (a) 2, 4, 6, 8, 10, 12, 14, 16, 18 or 20 of the amino acids at positions 34 to 70 of SEQ ID NO: 2 have been deleted, or wherein the amino acid residues at positions corresponding to positions 34 to 70 of SEQ ID NO: 2 have been deleted, and (b) 2, 4, 6, 8, 10, 12, 14, 16, 18 or 20 of the amino acids at positions 71 to 107 of SEQ ID NO: 2 have been deleted, or wherein the amino acid residues at positions corresponding to positions 71 to 107 of SEQ ID NO: 2 have been deleted.

The number of amino acids deleted from positions 34 to 70 may be different from the number of amino acids deleted from positions 71 to 107. The number of amino acids deleted from positions 34 to 70 is preferably the same as the number of amino acids deleted from positions 71 to 107.

Any combination of amino acids from positions 34 to 70 and amino acids from positions 71 to 107 may be deleted. The positions of the amino acids that have been deleted are preferably shown in a row of Table 1 or 2 or more than one row of Table 1 and/or 2. For instance, if D35 and V34 are deleted from positions 34 to 70, T104 and 1105 may be deleted from positions 71 to 107. Similarly, D35, V34, K37 and 138 may be deleted from positions 34 to 70 and E102, H103, T104 and 1105 may be deleted from positions 71 to 107. This ensures the maintenance of the beta sheet structure lining the barrel of the pore.

TABLE 1

| Residue for deletion facing into barrel between V34 and F70 | Corresponding residue for deletion facing out to membrane between V34 and F70 | Residue for deletion facing into barrel between I107 and E71 | Corresponding residue for deletion facing out to membrane I107 and E71 |
|---|---|---|---|
| D35 | V34 | T104 | I105 |
| D35 | V34 | T104 | H103 |
| D35 | Q36 | T104 | I105 |
| D35 | Q36 | T104 | H103 |
| K37 | Q36 | E102 | H103 |
| K37 | Q36 | E102 | I101 |
| K37 | I38 | E102 | H103 |
| K37 | I38 | E102 | I101 |
| T39 | I38 | V100 | I101 |
| T39 | I38 | V100 | K99 |
| T39 | I40 | V100 | I101 |
| T39 | I40 | V100 | K99 |
| T41 | I40 | S98 | K99 |
| T41 | I40 | S98 | E97 |
| T41 | K42 | S98 | K99 |
| T41 | K42 | S98 | E97 |
| G43 | K42 | Y96 | E97 |
| G43 | K42 | Y96 | V95 |
| G43 | M44 | Y96 | E97 |
| G43 | M44 | Y96 | V95 |
| K45 | M44 | E94 | V95 |
| K45 | M44 | E94 | T93 |
| K45 | N46 | E94 | V95 |
| K45 | N46 | E94 | T93 |
| V47 | N46 | E92 | T93 |
| V47 | N46 | E92 | T91 |
| V47 | N48 | E92 | T93 |
| V47 | N48 | E92 | T91 |
| S49 | N48 | M90 | T91 |
| S49 | N48 | M90 | S89 |
| S49 | E50 | M90 | T91 |
| S49 | E50 | M90 | S89 |
| T51 | E50 | V88 | S89 |
| T51 | E50 | V88 | Q87 |
| T51 | R52 | V88 | S89 |
| T51 | R52 | V88 | Q87 |

TABLE 1-continued

| Residue for deletion facing into barrel between V34 and F70 | Corresponding residue for deletion facing out to membrane between V34 and F70 | Residue for deletion facing into barrel between I107 and E71 | Corresponding residue for deletion facing out to membrane I107 and E71 |
|---|---|---|---|
| T53 | R52 | S86 | Q87 |
| T53 | R52 | S86 | E85 |
| T53 | V54 | S86 | Q87 |
| T53 | V54 | S86 | E85 |
| T55 | V54 | E84 | E85 |
| T55 | V54 | E84 | H83 |
| T55 | A56 | E84 | E85 |
| T55 | A56 | E84 | H83 |
| T57 | A56 | S82 | H83 |
| T57 | A56 | S82 | H81 |
| T57 | H58 | S82 | H83 |
| T57 | H58 | S82 | H81 |
| S59 | H58 | S80 | H81 |
| S59 | H58 | S80 | Y79 |
| S59 | I60 | S80 | H81 |
| S59 | I60 | S80 | Y79 |
| G61 | I60 | S78 | Y79 |
| G61 | I60 | S78 | V77 |
| G61 | S62 | S78 | Y79 |
| G61 | S62 | S78 | V77 |
| T63 | S62 | E76 | V77 |
| T63 | S62 | E76 | V75 |
| T63 | I64 | E76 | V77 |
| T63 | I64 | E76 | V75 |
| S65 | I64 | S74 | V75 |
| S65 | I64 | S74 | G73 |
| S65 | T66 | S74 | V75 |
| S65 | T66 | S74 | G73 |
| G67 | T66 | I72 | G73 |
| G67 | T66 | I72 | E71 |
| G67 | D68 | I72 | G73 |
| G67 | D68 | I72 | E71 |
| A69 | D68 | I72 | G73 |
| A69 | D68 | I72 | E71 |
| A69 | D70 | I72 | G73 |
| A69 | D70 | I72 | E71 |

TABLE 2

| Residue for deletion facing into barrel between I107 and E71 | Corresponding residue for deletion facing out to membrane I107 and E71 | Residue for deletion facing into barrel between V34 and F70 | Corresponding residue for deletion facing out to membrane between V34 and F70 |
|---|---|---|---|
| T106 | I107 | D35 | V34 |
| T106 | I107 | D35 | Q36 |
| T106 | I105 | D35 | V34 |
| T106 | I105 | D35 | Q36 |
| T104 | I105 | D35 | V34 |
| T104 | I105 | D35 | Q36 |
| T104 | H103 | D35 | V34 |
| T104 | H103 | D35 | Q36 |
| E102 | H103 | K37 | Q36 |
| E102 | H103 | K37 | I38 |
| E102 | I101 | K37 | Q36 |
| E102 | I101 | K37 | I38 |
| V100 | I101 | T39 | I38 |
| V100 | I101 | T39 | I40 |
| V100 | K99 | T39 | I38 |
| V100 | K99 | T39 | I40 |
| S98 | K99 | T41 | I40 |
| S98 | K99 | T41 | K52 |
| S98 | E97 | T41 | I40 |
| S98 | E97 | T41 | K52 |
| Y96 | E97 | G43 | K52 |
| Y96 | E97 | G43 | M44 |
| Y96 | V95 | G43 | K52 |
| Y96 | V95 | G43 | M44 |
| E94 | V95 | K45 | M44 |
| E94 | V95 | K45 | N46 |

TABLE 2-continued

| Residue for deletion facing into barrel between I107 and E71 | Corresponding residue for deletion facing out to membrane between I107 and E71 | Residue for deletion facing into barrel between V34 and F70 | Corresponding residue for deletion facing out to membrane between V34 and F70 |
|---|---|---|---|
| E94 | T93 | K45 | M44 |
| E94 | T93 | K45 | N46 |
| E92 | T93 | V47 | N46 |
| E92 | T93 | V47 | N48 |
| E92 | T91 | V47 | N46 |
| E92 | T91 | V47 | N48 |
| M90 | T91 | S49 | N48 |
| M90 | T91 | S49 | E50 |
| M90 | S89 | S49 | N48 |
| M90 | S89 | S49 | E50 |
| V88 | S89 | T51 | E50 |
| V88 | S89 | T51 | R52 |
| V88 | Q87 | T51 | E50 |
| V88 | Q87 | T51 | R52 |
| S86 | Q87 | T53 | R52 |
| S86 | Q87 | T53 | V54 |
| S86 | E85 | T53 | R52 |
| S86 | E85 | T53 | V54 |
| E84 | E85 | T55 | V54 |
| E84 | E85 | T55 | A56 |
| E84 | H83 | T55 | V54 |
| E84 | H83 | T55 | A56 |
| S82 | H83 | T57 | A56 |
| S82 | H83 | T57 | H58 |
| S82 | H81 | T57 | A56 |
| S82 | H81 | T57 | H58 |
| S80 | H81 | S59 | H58 |
| S80 | H81 | S59 | I60 |
| S80 | Y79 | S59 | H58 |
| S80 | Y79 | S59 | I60 |
| S78 | Y79 | G61 | I60 |
| S78 | Y79 | G61 | S62 |
| S78 | V77 | G61 | I60 |
| S78 | V77 | G61 | S62 |
| E76 | V77 | T63 | S62 |
| E76 | V77 | T63 | I64 |
| E76 | V75 | T63 | S62 |
| E76 | V75 | T63 | I64 |
| S74 | V75 | S65 | I64 |
| S74 | V75 | S65 | T66 |
| S74 | G73 | S65 | I64 |
| S74 | G73 | S65 | T66 |
| I72 | G73 | G67 | T66 |
| I72 | G73 | G67 | D68 |
| I72 | E71 | G67 | T66 |
| I72 | E71 | G67 | D68 |
| I72 | G73 | A69 | D68 |
| I72 | G73 | A69 | F70 |
| I72 | E71 | A69 | D68 |
| I72 | E71 | A69 | F70 |

The amino acids deleted from positions 34 to 70 and from positions 71 to 107 do not have to be in a row of Table 1 or 2. For instance, if D35 and V34 are deleted from positions 34 to 70, I72 and E71 may be deleted from positions 71 to 107.

The amino acids deleted from positions 34 to 70 are preferably consecutive. The amino acids deleted from positions 71 to 107 are preferably consecutive. The amino acids deleted from positions 34 to 70 and the amino acids deleted from positions 71 to 107 are preferably consecutive.

The invention preferably provides mutant monomers in which the following have been deleted:
(i) N46/V47/T91/T92; or
(ii) N48/S49/T91/T92.

The skilled person can identify other combinations of amino acids that may be deleted in accordance with the invention. The following discussion uses the numbering of residues in SEQ ID NO: 2 (i.e. before any amino acids have been deleted as defined above).

The barrel deletion variants further preferably comprise, where appropriate, any of the modifications and/or substitutions discussed above or below. By "where appropriate", we mean if the positions are still present in the mutant monomer following the barrel deletions.

Chemical Modifications

In another aspect, the invention provides a mutant lysenin monomer that is chemically-modified. The mutant monomer may be any of those discussed above or below. As a result, a mutant monomer of the invention, such as a variant of SEQ ID NO: 2 comprising a modification at one or more of the following positions K37, G43, K45, V47, S49, T51, H83, V88, T91, T93, V95, Y96, S98, K99, V100, I101, P108, P109, T110, S111, K112 and T114 or a variant comprising the barrel deletions discussed above, may be chemically-modified in accordance with the invention as discussed below.

A mutant monomer comprising any of the further modifications discussed below, i.e. comprising one or more modifications within the region of from about position 44 to about position 126 of SEQ ID NO: 2 which alter the ability of the monomer, or preferably the region, to interact with a polynucleotide, may be chemically modified. These chemically modified monomers need not comprise a modification of the invention, i.e. need not comprise a modification at one or more of the following positions K37, G43, K45, V47, S49, T51, H83, V88, T91, T93, V95, Y96, S98, K99, V100, I101, P108, P109, T110, S111, K112 and T114. A chemically-modified mutant monomer preferably comprises a variant of SEQ ID NO: 2 which comprises a substitution at one or more of the following positions of SEQ ID NO: 2 (a) E84, E85, E92, E97 and D126; (b) E85, E97 and D126 or (c) E84 and E92. Any number and combination of the substitutions discussed below may be made.

The mutant monomer can be chemically-modified in any way such that the diameter of the barrel or channel of a pore formed from the monomer is reduced or narrowed. This is discussed in more detail below.

The chemical modification is such that a chemical molecule is preferably covalently attached to the mutant monomer. The chemical molecule can be covalently attached to the mutant monomer using any method known in the art. The chemical molecule is typically attached via chemical linkage.

The mutant monomer is preferably chemically modified by attachment of a molecule to one or more cysteines (cysteine linkage), attachment of a molecule to one or more lysines, attachment of a molecule to one or more non-natural amino acids or enzyme modification of an epitope. If the chemical modifier is attached via cysteine linkage, the one or more cysteines have preferably been introduced to the mutant monomer by substitution. Suitable methods for carrying out such modifications are well-known in the art. Suitable non-natural amino acids include, but are not limited to, 4-azido-L-phenylalanine (Faz) and any one of the amino acids numbered 1-71 in FIG. 1 of Liu C. C. and Schultz P. G., Annu. Rev. Biochem., 2010, 79, 413-444.

The mutant monomer may be chemically modified by the attachment of any molecule which has the effect of reducing or narrowing the diameter of the barrel of a pore formed from the monomer at any location or site. For instance, the mutant monomer may be chemically modified by attachment of: (i) Maleimides such as: 4-phenylazomaleinanil, 1,N-(2-Hydroxyethyl)maleimide, N-Cyclohexylmaleimide, 1,3-Maleimidopropionic Acid, 1,1-4-Aminophenyl-1H-pyrrole, 2,5,dione, 1,1-4-Hydroxyphenyl-1H-pyrrole,2,5,dione, N-Ethylmaleimide, N-Methoxycarbonylmaleimide N-tert- Butylmaleimide, N-(2-Aminoethy)maleinide, 3-Maleimido-PROXYL, N-(4-Chlorophenyl)maleimide, 1-[4-(dimethylamino)-3,5-dinitrophenyl]-1H-pyrrole-2,5-dione, N-[4-(2-Benizmidazolyl)phenyl]maleimide, N-[4-(2-benzoxazoyl)phenyl]maleimide, N-(1 NAPHTHYL)-MALEIMIDE, N-(2,4-XYLYL)MALEIMIDE, N-(2,4-DIFLUOROPHENYL)MALEIMIDE, N-(3-CHLORO-PARA-TOLYL)-MALEIMIDE, 1-(2-Amino-ethyl)-pyrrole-2,5-dione hydrochloride, 1-cyclopentyl-3-methyl-2,5-dihydro-1H-pyrrole-2,5-dione, 1-(3-aminopropyl)-2,5-dihydro-1H-pyrrole-2,5-dione hydrochloride, 3-methyl-1-[2-ox-2-(piperazin-1-yl)ethyl]-2,5-dihydro-1-H-pyrrole-2,5-dione hydrochloride, 1-benzyl-2,5-dihydro-1H-pyrrole-2,5-dione, 3-methyl-1-(3,3,3-trifluropropyl)-2,5-dihydro-1H-pyrrole-2,5-dione, 1-[4-(methylamino)cyclohexyl]-2,5-dihydro-1H-pyrrole-2,5-dione trifluroacetic acid. SMILES O=C1C=CC(=O)N1CC=2C=CN=CC2, SMILES O=C1C=CC(=O)N1CN2CCNCC2. 1-benzyl-3-methyl-2,5-dihydro-1H-pyrrole-2,5-dione, 1-(2-fluorophenyl)-3-methyl-2,5-dihydro 1H-pyrrole-2,5-dione, N-(4-PHENOXYPHENYL)MALEIMIDE, N-(4-NITROPHENYL)MALEIMIDE; (ii) Iodocetamides such as: 3-(2-Iodoacetamido)-PROXYL, N-(cyclopropylmethyl)-2-iodoacetamide, 2-iodo-N-(2-phenylethyl)acetamide, 2-iodo-N-(2,2,2-trifluoroethyl)acetamide, N-(4-ACETYLPHENYL)-2-IODOACETAMIDE, N-(4-(AMINOSULFONYL)PHENYL)-2-IODOACETAMIDE, N-(1,3-BENZOTHIAZOL-2-YL)-2-IODOACETAMIDE, N-(2,6-DIETHYLPHENYL)-2-IODOACETAMIDE, N-(2-benzoyl-4-chlorophenyl)-2-iodoacetamide; (iii) Bromoacetamides: such as N-(4-(ACETYLAMINO)PHENYL)-2-BROMOACETAMIDE, N-(2-ACETYLPHENYL)-2-BROMOACETAMIDE, 2-BROMO-N-(2-CYANOPHENYL)ACETAMIDE, 2-BROMO-N-(3-(TRIFLUOROMETHYL)PHENYL)ACETAMIDE, N-(2-benzoylphenyl)-2-bromoacetamide, 2-bromo-N-(4-fluorophenyl)-3-methylbutanamide, N-Benzyl-2-bromo-N-phenylpropionamide, N-(2-BROMO-BUTYRYL)-4-CHLORO-BENZENESULFONAMIDE, 2-Bromo-N-methyl-N-phenylacetamide, 2-bromo-N-phenethyl-acetartide. 2-ADAMANTAN-1-YL-2-BROMO-N-CYCLOHEXYL-ACETAMIDE, 2-bromo-N-(2-methylphenyl)butanamide, Monobromoacetanilide; (iv) Disulphides such as: ALDRITHIOL-2, ALDRITHIOL-4, ISOPROPYL DISULFIDE, 1-(Isobutyldisulfanyl)-2-methylpropane, Dibenzyl disulfide, 4-AMINOPHENYL DISULFIDE, 3-(2-Pyridyldithio)propionic acid, 3-(2-Pyridyldithio)propionic acid hydrazide, 3-(2-Pyridyldithio)propionic acid N-succinimidyl ester, am6amPDP1-βCD; and (v) Thiols such as: 4-Phenylthiazole-2-thiol, Purpald, 5,6,7,8TETRAHYDRO-QUINAZOLINE-2-THIOL.

The mutant monomer may be chemically modified by attachment of polyethylene glycol (PEG), a nucleic acid, such as DNA, a dye, a fluorophore or a chromophore. In some embodiments, the mutant monomer is chemically modified with a molecular adaptor that facilitates the interaction between a pore comprising the monomer and a target analyte, a target nucleotide or target polynucleotide. The presence of the adaptor improves the host-guest chemistry of the pore and the nucleotide or polynucleotide and thereby improves the sequencing ability of pores formed from the mutant monomer.

The chemically-modified mutant monomer preferably comprises a variant of the sequence shown in SEQ ID NO: 2. Variants are defined below. The variant typically comprises one or more substitutions in which one or more residues are replaced with cysteine, lysine or a non-natural amino acid. Non-natural amino acids include, but are not limited, to 4-Azido-L-phenylalanine (Faz), 4-Acetyl-L-phenylalanine, 3-Acetyl-L-phenylalanine, 4-Acetoacetyl-L-phenylalanine, O-Allyl-L-tyrosine, 3-(Phenylselanyl)-L-alanine, O-2-Propyn-1-yl-L-tyrosine, 4-(Dihydroxyboryl)-L-phenylalanine, 4-[(Ethylsulfanyl)carbonyl]-L-phenylalanine, (2S)-2-amino-3-4-[(propan-2-ylsulfanyl)carbonyl]phenyl; propanoic acid, (2S)-2-amino-3-4-[(2-amino-3-sulfanylpropanoyl)amino]phenyl; propanoic acid, O-Methyl-L-tyrosine, 4-Amino-L-phenylalanine, 4-Cyano-L-phenylalanine, 3-Cyano-L-phenylalanine, 4-Fluoro-L-phenylalanine, 4-Iodo-L-phenylalanine, 4-Bromo-L-phenylalanine, O-(Trifluoromethyl)tyrosine, 4-Nitro-L-phenylalanine, 3-Hydroxy-L-tyrosine, 3-Amino-L-tyrosine, 3-Iodo-L-tyrosine, 4-Isopropyl-L-phenylalanine, 3-(2-Naphthyl)-L-alanine, 4-Phenyl-L-phenylalanine, (2S)-2-amino-3-(naphthalen-2-ylamino)propanoic acid, 6-(Methylsulfanyl)norleucine, 6-Oxo-L-lysine, D-tyrosine, (2R)-2-Hydroxy-3-(4-hydroxyphenyl)propanoic acid, (2R)-2-Ammoniooctanoate3-(2,2'-Bipyridin-5-yl)-D-alanine, 2-amino-3-(8-hydroxy-3-quinolyl)propanoic acid, 4-Benzoyl-L-phenylalanine, S-(2-Nitrobenzyl)cysteine, (2R)-2-amino-3-[(2-nitrobenzyl)sulfanyl]propanoic acid, (2S)-2-amino-3-[(2-nitrobenzyl)oxy]propanoic acid, O-(4,5-Dimethoxy-2-nitrobenzyl)-L-serine, (2S)-2-amino-6-([(2-nitrobenzyl)oxy]carbonyl;amino)hexanoic acid, O-(2-Nitrobenzyl)-L-tyrosine, 2-Nitrophenylalanine, 4-[(E)-Phenyldiazenyl]-L-phenylalanine, 4-[3-(Trifluoromethyl)-3H-diaziren-3-yl]-D-phenylalanine, 2-amino-3-[[5-(dimethylamino)-1-naphthyl]sulfonylamino]propanoic acid, (2S)-2-amino-4-(7-hydroxy-2-oxo-2H-chromen-4-yl)butanoic acid, (2S)-3-[(6-acetylnaphthalen-2-yl)amino]-2-aminopropanoic acid, 4-(Carboxymethyl)phenylalanine, 3-Nitro-L-tyrosine, O-Sulfo-L-tyrosine, (2R)-6-Acetamido-2-ammoniohexanoate, 1-Methylhistidine, 2-Aminononanoic acid, 2-Aminodecanoic acid, L-Homocysteine, 5-Sulfanylnorvaline, 6-Sulfanyl-L-norleucine, 5-(Methylsulfanyl)-L-norvaline, $N^6$-[(2R,3R)-3-Methyl-3,4-dihydro-2H-pyrrol-2-yl]carbonyl;-L-lysine, $N^6$-[(Benzyloxy)carbonyl]lysine, (2S)-2-amino-6-[(cyclopentylcarbonyl)amino]hexanoic acid, $N^6$-[(Cyclopentyloxy)carbonyl]-L-lysine, (2S)-2-amino-6-[(2R)-tetrahydrofuran-2-ylcarbonyl]amino; hexanoic acid, (2S)-2-amino-8-[(2R,3S)-3-ethynyltetrahydrofuran-2-yl]-8-oxooctanoic acid, $N^6$-(tert-Butoxycarbonyl)-L-lysine, (2S)-2-Hydroxy-6-([(2-methyl-2-propanyl)oxy]carbonyl;amino)hexanoic acid, $N^6$-[(Allyloxy)carbonyl]lysine, (2S)-2-amino-6-([(2-azidobenzyl)oxy]carbonyl;amino)hexanoic acid, $N^6$-L-Prolyl-L-lysine, (2S)-2-amino-6-[(prop-2-yn-1-yloxy)carbonyl]amino; hexanoic acid and $N^6$-[(2-Azidoethoxy)carbonyl]-L-lysine. The most preferred non-natural amino acid is 4-azido-L-phenylalanine (Faz).

The mutant monomer may be chemically modified by the attachment of any molecule at any of positions of SEQ ID NO: 2: K37, V47, S49, T55, S86, E92 and E94. More preferably, the mutant monomer may be chemically modified by the attachment of any molecule at position E92 and/or E94. In one embodiment, the mutant monomer is chemically modified by attachment of a molecule to one or more cysteines (cysteine linkage), one or more lysines or one or more non-natural amino acids at these positions. The mutant monomer preferably comprises a variant of the sequence shown in SEQ ID NO: 2 comprising one or more of K37C, V47C, S49C, T55C, S86C, E92C and E94C wherein one or more molecules are attached to the one or more introduced cysteines. The mutant monomer preferably comprises a variant of the sequence shown in SEQ ID NO: 2 comprising E92C and/or E94C wherein one or more molecules are attached to the introduced cysteine(s).

In each of these two preferred embodiments, the one or more cysteines (Cs) may be replaced with one or more lysines or one or more non-natural amino acids, such as one or more Fazs.

The reactivity of cysteine residues may be enhanced by modification of the adjacent residues. For instance, the basic groups of flanking arginine, histidine or lysine residues will change the pKa of the cysteines thiol group to that of the more reactive S$^-$ group. The reactivity of cysteine residues may be protected by thiol protective groups such as dTNB. These may be reacted with one or more cysteine residues of the mutant monomer before a linker is attached.

The molecule may be attached directly to the mutant monomer. The molecule is preferably attached to the mutant monomer using a linker, such as a chemical crosslinker or a peptide linker. Suitable chemical crosslinkers are well-known in the art. Preferred crosslinkers include 2,5-dioxopyrrolidin-1-yl 3-(pyridin-2-yldisulfanyl)propanoate, 2,5-dioxopyrrolidin-1-yl 4-(pyridin-2-yldisulfanyl)butanoate and 2,5-dioxopyrrolidin-1-yl 8-(pyridin-2-yldisulfanyl)octananoate. The most preferred crosslinker is succinimidyl 3-(2-pyridyldithio)propionate (SPDP). Typically, the molecule is covalently attached to the bifunctional crosslinker before the molecule/crosslinker complex is covalently attached to the mutant monomer but it is also possible to covalently attach the bifunctional crosslinker to the monomer before the bifunctional crosslinker/monomer complex is attached to the molecule.

The linker is preferably resistant to dithiothreitol (DTT). Suitable linkers include, but are not limited to, iodoacetamide-based and maleimide-based linkers.

Advantages of pores comprising the chemically-modified mutant monomers of the invention are discussed in more detail below.

Further chemical modifications that may be made in accordance with the invention are discussed below.

Further Modifications

Any of the mutant monomers discussed above may have further modifications within the region from about position 44 to about position 126 of SEQ ID NO: 2 where appropriate (i.e. where the relevant amino positions remain in the mutant monomer or are not modified/substituted with another amino acid). At least a part of this region typically contributes to the membrane spanning region of lysenin. At least a part of this region typically contributes to the barrel or channel of lysenin. At least a part of this region typically contributes to the internal wall or lining of lysenin.

The transmembrane region of lysenin has been identified as positions 44 to 67 of SEQ ID NO: 2 (De Colbis et al., Structure, 2012; 20: 1498-1507).

The variant preferably comprises one or more modifications within the region of from about position 44 to about position 126 of SEQ ID NO: 2 which alter the ability of the monomer, or preferably the region, to interact with a polynucleotide. The interaction between the monomer and a polynucleotide may be increased or decreased. An increased interaction between the monomer and a polynucleotide will, for example, facilitate capture of the polynucleotide by pores comprising the mutant monomer. A decreased interaction between the region and a polynucleotide will, for example, improve recognition or discrimination of the polynucleotide. Recognition or discrimination of the polynucleotide may be improved by decreasing the variance of states of pores comprising the mutant monomer (which increases the signal-to-noise ratio) and/or decreasing the number of nucleotides in the polynucleotide contributing to the current as the polynucleotide moves through pores comprising the mutant monomer.

The ability of the monomer to interact with a polynucleotide can be determined using methods that are well-known in the art. The monomer may interact with a polynucleotide in any way, e.g. by non-covalent interactions, such as hydrophobic interactions, hydrogen bonding, Van der Waal's forces, pi ($\pi$)-cation interactions or electrostatic forces. For instance, the ability of the region to bind to a polynucleotide can be measured using a conventional binding assay. Suitable assays include, but are not limited to, fluorescence-based binding assays, nuclear magnetic resonance (NMR), Isothermal Titration calorimetry (ITC) or Electron spin resonance (ESR) spectroscopy. Alternatively, the ability of a pore comprising one or more of the mutant monomers to interact with a polynucleotide can be determined using any of the methods discussed above or below. Preferred assays are described in the Examples.

One or more modifications may be further made within the region from about position 44 to about position 126 of SEQ ID NO: 2. The one or more modifications are preferably within any one of the following regions: from about position 40 to about position 125, from about position 50 to about position 120, from about position 60 to about position 110 and from about position 70 to about position 100. If the one or more modifications are being made to improve polynucleotide capture, they are more preferably made within any one of the following regions: from about position 44 to about position 103, from about position 68 to about position 103, from about position 84 to about position 103, from about position 44 to about position 97, from about position 68 to about position 97 or from about position 84 to about position 97. If the one or more modifications are being made to improve polynucleotide recognition or discrimination, they are more preferably made within any one of the following regions: from about position 44 to about position 109, from about position 44 to about position 97 or from about position 48 to about position 88. The region is preferably from about position 44 to about position 67 of SEQ ID NO: 2.

If the one or more modifications are intended improve polynucleotide recognition or discrimination, they are preferably made in addition to one or more modifications to improve polynucleotide capture. This allows pores formed from the mutant monomer to effectively capture a polynucleotide and then characterise the polynucleotide, such as estimate its sequence, as discussed below.

Modifications of protein nanopores that alter their ability to interact with a polynucleotide, in particular improve their ability to capture and/or recognise or discriminate polynucleotides, are well documented in the art. For instance, such modifications are disclosed in WO 2010/034018 and WO 2010/055307. Similar modifications can be made to the lysenin monomer in accordance with this invention.

Any number of modifications may be made, such as 1, 2, 5, 10, 15, 20, 30 or more modifications. Any modification(s) can be made as long as the ability of the monomer to interact with a polynucleotide is altered. Suitable modifications include, but are not limited to, amino acid substitutions, amino acid additions and amino acid deletions. The one or more modifications are preferably one or more substitutions. This is discussed in more detail below.

The one or more modifications preferably (a) alter the steric effect of the monomer, or preferably alter the steric effect of the region, (b) alter the net charge of the monomer, or preferably alter the net charge of the region, (c) alter the ability of the monomer, or preferably of the region, to hydrogen bond with the polynucleotide, (d) introduce or remove chemical groups that interact through delocalized electron pi systems and/or (e) alter the structure of the monomer, or preferably alter the structure of the region. The one or more modifications more preferably result in any combination of (a) to (e), such as (a) and (b); (a) and (c); (a) and (d); (a) and (e); (b) and (c); (b) and (d); (b) and (e); (c) and (d); (c) and (e); (d) and (e), (a), (b) and (c); (a), (b) and (d); (a), (b) and (e); (a), (c) and (d); (a), (c) and (e); (a), (d) and (e); (b), (c) and (d); (b), (c) and (e); (b), (d) and (e); (c), (d) and (e); (a), (b), (c) and d); (a), (b), (c) and (e); (a), (b), (d) and (e); (a), (c), (d) and (e); (b), (c), (d) and (e); and (a), (b), (c) and (d).

For (a), the steric effect of the monomer can be increased or decreased. Any method of altering the steric effects may be used in accordance with the invention. The introduction of bulky residues, such as phenylalanine (F), tryptophan (W), tyrosine (Y) or histidine (H), increases the sterics of the monomer. The one or more modifications are preferably the introduction of one or more of F, W, Y and H. Any combination of F, W, Y and H may be introduced. The one or more of F, W, Y and H may be introduced by addition. The one or more of F, W, Y and H are preferably introduced by substitution. Suitable positions for the introduction of such residues are discussed in more detail below.

The removal of bulky residues, such as phenylalanine (F), tryptophan (W), tyrosine (Y) or histidine (H), conversely decreases the sterics of the monomer. The one or more modifications are preferably the removal of one or more of F, W, Y and H. Any combination of F, W, Y and H may be removed. The one or more of F, W, Y and H may be removed by deletion. The one or more of F, W, Y and H are preferably removed by substitution with residues having smaller side groups, such as serine (S), threonine (T), alanine (A) and valine (V).

For (b), the net charge can be altered in any way. The net positive charge is preferably increased or decreased. The net positive charge can be increased in any manner. The net positive charge is preferably increased by introducing, preferably by substitution, one or more positively charged amino acids and/or neutralising, preferably by substitution, one or more negative charges.

The net positive charge is preferably increased by introducing one or more positively charged amino acids. The one or more positively charged amino acids may be introduced by addition. The one or more positively charged amino acids are preferably introduced by substitution. A positively charged amino acid is an amino acid with a net positive charge. The positively charged amino acid(s) can be naturally-occurring or non-naturally-occurring. The positively charged amino acids may be synthetic or modified. For instance, modified amino acids with a net positive charge may be specifically designed for use in the invention. A number of different types of modification to amino acids are well known in the art.

Preferred naturally-occurring positively charged amino acids include, but are not limited to, histidine (H), lysine (K) and arginine (R). The one or more modifications are preferably the introduction of one or more of H, K and R. Any number and combination of H, K and R may be introduced. The one or more of H, K and R may be introduced by addition. The one or more of H, K and R are preferably introduced by substitution. Suitable positions for the introduction of such residues are discussed in more detail below.

Methods for adding or substituting naturally-occurring amino acids are well known in the art. For instance, methionine (M) may be substituted with arginine (R) by replacing the codon for methionine (ATG) with a codon for arginine (AGA) at the relevant position in a polynucleotide encoding the monomer. The polynucleotide can then be expressed as discussed below.

Methods for adding or substituting non-naturally-occurring amino acids are also well known in the art. For instance, non-naturally-occurring amino acids may be introduced by including synthetic aminoacyl-tRNAs in the IVTT system used to express the pore. Alternatively, they may be introduced by expressing the monomer in *E. coli* that are auxotrophic for specific amino acids in the presence of synthetic (i.e. non-naturally-occurring) analogues of those specific amino acids. They may also be produced by naked ligation if the pore is produced using partial peptide synthesis.

Any amino acid may be substituted with a positively charged amino acid. One or more uncharged amino acids, non-polar amino acids and/or aromatic amino acids may be substituted with one or more positively charged amino acids. Uncharged amino acids have no net charge. Suitable uncharged amino acids include, but are not limited to, cysteine (C), serine (S), threonine (T), methionine (M), asparagine (N) and glutamine (Q). Non-polar amino acids have non-polar side chains. Suitable non-polar amino acids include, but are not limited to, glycine (G), alanine (A), proline (P), isoleucine (I), leucine (L) and valine (V). Aromatic amino acids have an aromatic side chain. Suitable aromatic amino acids include, but are not limited to, histidine (H), phenylalanine (F), tryptophan (W) and tyrosine (Y). Preferably, one or more negatively charged amino acids are substituted with one or more positively charged amino acids. Suitable negatively charged amino acids include, but are not limited to, aspartic acid (D) and glutamic acid (E).

Preferred introductions include, but are not limited to, substitution of E with K, M with R, substitution of M with H, substitution of M with K, substitution of D with R, substitution of D with H, substitution of D with K, substitution of E with R, substitution of E with H, substitution of N with R, substitution of T with R and substitution of G with R. Most preferably E is substituted with K.

Any number of positively charged amino acids may be introduced or substituted. For instance, 1, 2, 5, 10, 15, 20, 25, 30 or more positively charged amino acids may be introduced or substituted.

The net positive charge is more preferably increased by neutralising one or more negative charges. The one or more negative charges may be neutralised by replacing by substitution one or more negatively charged amino acids with one or more uncharged amino acids, non-polar amino acids and/or aromatic amino acids. The removal of negative charge increases the net positive charge. The uncharged amino acids, non-polar amino acids and/or aromatic amino acids can be naturally-occurring or non-naturally-occurring. They may be synthetic or modified. Suitable uncharged amino acids, non-polar amino acids and aromatic amino acids are discussed above. Preferred substitutions include, but are not limited to, substitution of E with Q, substitution of E with S, substitution of E with A, substitution of D with Q, substitution of E with N, substitution of D with N, substitution of D with G and substitution of D with S.

Any number and combination of uncharged amino acids, non-polar amino acids and/or aromatic amino acids may substituted. For instance, 1, 2, 5, 10, 15, 20, 25, or 30 or more uncharged amino acids, non-polar amino acids and/or aromatic amino acids may be substituted. Negatively charged amino acids may be substituted with (1) uncharged amino acids; (2) non-polar amino acids; (3) aromatic amino acids; (4) uncharged amino acids and non-polar amino acids; (5) uncharged amino acids and aromatic amino acids; and (5) non-polar amino acids and aromatic amino acids; or (6) uncharged amino acids, non-polar amino acids and aromatic amino acids.

The one or more negative charges may be neutralised by introducing one or more positively charged amino acids near to, such as within 1, 2, 3 or 4 amino acids, or adjacent to one or more negatively charged amino acids. Examples of positively and negatively charged amino acids are discussed above. The positively charged amino acids may be introduced in any manner discussed above, for instance by substitution.

The net positive charge is preferably decreased by introducing one or more negatively charged amino acids and/or neutralising one or more positive charges. Ways in which this might be done will be clear from the discussion above with reference to increasing the net positive charge. All of the embodiments discussed above with reference to increasing the net positive charge equally apply to decreasing the net positive charge except the charge is altered in the opposite way. In particular, the one or more positive charges are preferably neutralised by substituting one or more positively charged amino acids with one or more uncharged amino acids, non-polar amino acids and/or aromatic amino acids or by introducing one or more negatively charged amino acids near to, such as within 1, 2, 3 or 4 amino acids of, or adjacent to one or more positively charged amino acids.

The net negative charge is preferably increased or decreased. All of the above embodiments discussed above with reference to increasing or decreasing the net positive charge equally apply to decreasing or increasing the net negative charge respectively.

For (c), the ability of the monomer to hydrogen bond may be altered in any manner. The introduction of serine (S), threonine (T), asparagine (N), glutamine (Q), tyrosine (Y) or histidine (H) increases the hydrogen bonding ability of the monomer. The one or more modifications are preferably the introduction of one or more of S, T, N, Q, Y and H. Any combination of S, T, N, Q, Y and H may be introduced. The one or more of S, T, N, Q, Y and H may be introduced by addition. The one or more of S, T, N, Q, Y and H are preferably introduced by substitution. Suitable positions for the introduction of such residues are discussed in more detail below.

The removal of serine (S), threonine (T), asparagine (N), glutamine (Q), tyrosine (Y) or histidine (H) decreases the hydrogen bonding ability of the monomer. The one or more modifications are preferably the removal of one or more of S, T, N, Q, Y and H. Any combination of S, T, N, Q, Y and H may be removed. The one or more of S, T, N, Q, Y and H may be removed by deletion. The one or more of S, T, N, Q, Y and H are preferably removed by substitution with other amino acids which hydrogen bond less well, such as alanine (A), valine (V), isoleucine (I) and leucine (L).

For (d), the introduction of aromatic residues, such as phenylalanine (F), tryptophan (W), tyrosine (Y) or histidine (H), also increases the pi stacking in the monomer. The removal of aromatic residues, such as phenylalanine (F), tryptophan (W), tyrosine (Y) or histidine (H), also decreases the pi stacking in the monomer. Such amino acids can be introduced or removed as discussed above with reference to (a).

For (e), one or more modifications can be made in accordance with the invention which alter the structure of the monomer. For example, one or more loop regions can be removed, shortened or extended. This typically facilitates the entry or exit of a polynucleotide into or out of the pore. The one or more loop regions may be the cis side of the pore, the trans side of the pore or on both sides of the pore. Alternatively, one or more regions of the amino terminus and/or the carboxy terminus of the pore can be extended or deleted. This typically alters the size and/or charge of the pore.

It will be clear from the discussion above that the introduction of certain amino acids will enhance the ability of the monomer to interact with a polynucleotide via more than one mechanism. For instance, the substitution of E with H will not only increase the net positive charge (by neutralising negative charge) in accordance with (b), but will also increase the ability of the monomer to hydrogen bond in accordance with (c).

The variant preferably comprises a substitution at one or more of the following positions of SEQ ID NO: 2: M44, N46, N48, E50, R52, H58, D68, F70, E71, S74, E76, S78, Y79, S80, H81, S82, E84, E85, S86, Q87, S89, M90, E92, E94, E97, E102, H103, T104, T106, R115, Q117, N119, D121 and D126. The variant preferably comprises a substitution at 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33 or 34 of those positions. The variant preferably comprises a substitution at one or more of the following positions of SEQ ID NO: 2: D68, E71, S74, E76, S78, S80, S82, E84, E85, S86, Q87, S89, E92, E102, T104, T106, R115, Q117, N119 and D121. The variant preferably comprises a substitution at 1, 2, 3, 4, 5, 6, 7, 8, 9, 10, 11, 12, 13, 14, 15, 16, 17, 18, 19 or 20 of those positions.

The variant preferably comprises a substitution at one or more of the following positions of SEQ ID NO: 2 (a) E84, E85, E92, E97 and D126; (b) E85, E97 and D126 or (c) E84 and E92. The amino acids substituted into the variant may be naturally-occurring or non-naturally occurring derivatives thereof. The amino acids substituted into the variant may be D-amino acids. Each position listed above may be substituted with asparagine (N), serine (S), glutamine (Q), arginine (R), glycine (G), tyrosine (Y), aspartic acid (D), leucine (L), lysine (K) or alanine (A).

The variant preferably comprises at least one of the following mutations of SEQ ID NO: 2:
(a) serine (S) at position 44;
(b) serine (S) at position 46;
(c) serine (S) at position 48;
(d) serine (S) at position 52;
(e) serine (S) at position 58;
(f) serine (S) at position 68;
(g) serine (S) at position 70;
(h) serine (S) at position 71;
(i) serine (S) at position 76;
(j) serine (S) at position 79;
(k) serine (S) at position 81;
(l) serine (S), aspartic acid (D) or glutamine (Q) at position 84;
(m) serine (S) or lysine (K) at position 85;
(n) serine (S) at position 87;
(o) serine (S) at position 90;
(p) asparagine (N) or glutamine (Q) at position 92;
(q) serine (S) or asparagine (N) at position 94;
(r) serine (S) or asparagine (N) at position 97;
(s) serine (S) at position 102;
(t) serine (S) at position 103;
(u) asparagine (N) or serine (S) at position 121;
(v) serine (S) at position 50;
(w) asparagine (N) or serine (S) at position 94;

(x) asparagine (N) or serine (S) at position 97;
(y) serine (S) or asparagine (N) at position 121;
(z) asparagine (N) or glutamine (Q) or glycine (G) at position 126; and
(aa) serine (S) or asparagine (N) at position 128.

The variant may include any number of mutations (a) to (aa), such as 1, 2, 3, 4, 5, 6, 7, 8, 9, 10, 11, 12, 13, 14, 15, 16, 17, 18, 19, 20, 21, 22, 23, 24, 25, 26 or 27 of the mutations. Preferred combinations of mutations are discussed below. The amino acids introduced into the variant may be naturally-occurring or non-naturally occurring derivatives thereof. The amino acids introduced into the variant may be D-amino acids.

The variant preferably comprises at least one of the following mutations of SEQ ID NO: 2:
(a) serine (S) at position 68;
(b) serine (S) at position 71;
(c) serine (S) at position 76;
(d) aspartic acid (D) or glutamine (Q) at position 84;
(e) lysine (K) at position 85;
(f) asparagine (N) or glutamine (Q) at position 92;
(g) serine (S) at position 102;
(h) asparagine (N) or serine (S) at position 121;
(i) serine (S) at position 50;
(j) asparagine (N) or serine (S) at position 94;
(k) asparagine (N) or serine (S) at position 97; and
(l) asparagine (N) or glutamine (Q) or glycine (G) at position 126.

The variant may include any number of mutations (a) to (l), such as 1, 2, 3, 4, 5, 6, 7, 8, 9, 10, 11 or 12 of the mutations. Preferred combinations of mutations are discussed below. The amino acids introduced into the variant may be naturally-occurring or non-naturally occurring derivatives thereof. The amino acids introduced into the variant may be D-amino acids.

The variant may include one or more additional modifications outside of the region of from about position 44 to about position 126 of SEQ ID NO: 2 which in combination with the modifications in the region discussed above improve polynucleotide capture and/or improve polynucleotide recognition or discrimination. Suitable modifications include, but are not limited to, substitution at one or more of D35, E128, E135, E134 and E167. In particular, removal of the negative charge by substituting E at one or more of positions 128, 135, 134 and 167 improves polynucleotide capture. E at one or more of these positions may be substituted in any of the ways discussed above. Preferably all of E128, E135, E134 and E167 are substituted as discussed above. E is preferably substituted with A. In other words, the variant preferably comprises one or more of, or all of, E128A, E135A, E134A and E167A. Another preferred substitution is D35Q.

In a preferred embodiment, the variant comprises the following substitutions in SEQ ID NO: 2:
i. one or more of, such as both of, E84D and E85K;
ii. one or more of, such as 2, 3, 4, 5 or 6 of, E84Q, E85K, E92Q, E97S, D126G and E167A;
iii. one or more of, such as 2, 3, 4 or 5 of, E92N, E94N, E97N, D121N and D126N;
iv. one or more of, such as 2, 3, 4, 5 or 6 of, E92N, E94N, E97N, D121N, D126N and E128N;
v. one or more of, such as 2, 3, 4, 5, 6 or 7 of, E76S, E84Q, E85K, E92Q, E97S, D126G and E167A;
vi. one or more of, such as 2, 3, 4, 5, 6 or 7 of, E84Q, E85K, E92Q, E97S, D126G, E167A and E505;
vii. one or more of, such as 2, 3, 4, 5, 6 or 7 of, E84Q, E85K, E92Q, E97S, D126G, E167A and E71S;
viii. one or more of, such as 2, 3, 4, 5, 6 or 7 of, E84Q, E85K, E92Q, E97S, D126G, E167A and E94S;
ix. one or more of, such as 2, 3, 4, 5, 6 or 7 of, E84Q, E85K, E92Q, E97S, D126G, E167A and E102S;
x. one or more of, such as 2, 3, 4, 5, 6 or 7 of, E84Q, E85K, E92Q, E97S, D126G, E167A and E128S;
xi. one or more of, such as 2, 3, 4, 5, 6 or 7 of, E84Q, E85K, E92Q, E97S, D126G, E167A and E135S;
xii. one or more of, such as 2, 3, 4, 5, 6 or 7 of, E84Q, E85K, E92Q, E97S, D126G, E167A and D68S;
xiii. one or more of, such as 2, 3, 4, 5, 6 or 7 of, E84Q, E85K, E92Q, E97S, D126G, E167A and D121S;
xiv. one or more of, such as 2, 3, 4, 5, 6 or 7 of, E84Q, E85K, E92Q, E97S, D126G, E167A and D134S;
xv. one or more of, such as 2 or 3 of, E84D, E85K and E92Q;
xvi. one or more of, such as 1, 2, 3, 4, 5 or 6 of, E84Q, E85K, E92Q, E97S, D126G and E135S;
xvii. one or more of, such as 1, 2, 3, 4 or 5 of, E85K, E92Q, E94S, E97S and D126G;
xviii. one or more of, such as 1, 2, 3, 4 or 5 of, E76S, E85K, E92Q, E97S and D126G;
xix. one or more of, such as 1, 2, 3, 4 or 5 of, E71S, E85K, E92Q, E97S and D126G;
xx. one or more of, such as 1, 2, 3, 4 or 5 of, D68S, E85K, E92Q, E97S and D126G;
xxi. one or more of, such as 1, 2, 3 or 4 of, E85K, E92Q, E97S and D126G;
xxii. one or more of, such as 1, 2, 3, 4, 5 or 6 of, E84Q, E85K, E92Q, E97S, H103S and D126G;
xxiii. one or more of, such as 1, 2, 3, 4, 5 or 6 of, E84Q, E85K, M90S, E92Q, E97S and D126G;
xxiv. one or more of, such as 1, 2, 3, 4, 5 or 6 of, E84Q, Q87S, E85K, E92Q, E97S and D126G;
xxv. one or more of, such as 1, 2, 3, 4 or 5 of, E84Q, E85S, E92Q, E97S and D126G;
xxvi. one or more of, such as 1, 2, 3, 4 or 5 of, E84S, E85K, E92Q, E97S and D126G;
xxvii. one or more of, such as 1, 2, 3, 4, 5 or 6 of, H81S, E84Q, E85K, E92Q, E97S and D126G;
xxviii. one or more of, such as 1, 2, 3, 4, 5 or 6 of, Y79S, E84Q, E85K, E92Q, E97S and D126G;
xxix. one or more of, such as 1, 2, 3, 4, 5 or 6 of, F70S, E84Q, E85K, E92Q, E97S and D126G;
xxx. one or more of, such as 1, 2, 3, 4, 5 or 6 of, H58S, E84Q, E85K, E92Q, E97S and D126G;
xxxi. one or more of, such as 1, 2, 3, 4, 5 or 6 of, R52S, E84Q, E85K, E92Q, E97S and D126G;
xxxii. one or more of, such as 1, 2, 3, 4, 5 or 6 of, N48S, E84Q, E85K, E92Q, E97S and D126G;
xxxiii. one or more of, such as 1, 2, 3, 4, 5 or 6 of, N46S, E84Q, E85K, E92Q, E97S and D126G;
xxxiv. one or more of, such as 1, 2, 3, 4, 5 or 6 of, M44S, E84Q, E85K, E92Q, E97S and D126G;
xxxv. one or more of, such as both of, E92Q and E97S;
xxxvi. one or more of, such as 1, 2, 3 or 4 of, E84Q, E85K, E92Q and E97S;
xxxvii. one or more of, such as both of, E84Q and E85K;
xxxviii. one or more of, such as 1, 2 or 3 of, E84Q, E85K and D126G;
xxxix. one or more of, such as 1, 2, 3 or 4 of, E84Q, E85K, D126G and E167A;
xl. one or more of, such as 1, 2 or 3 of, E92Q, E97S and D126G;
xli. one or more of, such as 1, 2, 3, 4 or 5 of, E84Q, E85K, E92Q, E97S and D126G;

xlii. one or more of, such as 1, 2, 3, 4 or 5 of, E84Q, E85K, E92Q, E97S and E167A;
xliii. one or more of, such as 1, 2, 3, 4 or 5 of, E84Q, E85K, E92Q, D126G and E167A;
xliv. one or more of, such as 1, 2, 3, 4 or 5 of, E84Q, E85K, E97S, D126G and E167A;
xlv. one or more of, such as 1, 2, 3, 4 or 5 of, E84Q, E92Q, E97S, D126G and E167A;
xlvi. one or more of, such as 1, 2, 3, 4 or 5 of, E85K, E92Q, E97S, D126G and E167A;
xlvii. one or more of, such as 1, 2 or 3 of, E84D, E85K and E92Q;
xlviii. one or more of, such as 1, 2, 3, 4, 5, 6 or 7 of, E84Q, E85K, E92Q, E97S, D126G, E167A and D121S;
xlix. one or more of, such as 1, 2, 3, 4, 5, 6 or 7 of, E84Q, E85K, E92Q, E97S, D126G, E167A and D68S;
l. one or more of, such as 1, 2, 3, 4, 5, 6 or 7 of, E84Q, E85K, E92Q, E97S, D126G, E167A and E135S;
li. one or more of, such as 1, 2, 3, 4, 5, 6 or 7 of, E84Q, E85K, E92Q, E97S, D126G, E167A and E128S;
lii. one or more of, such as 1, 2, 3, 4, 5, 6 or 7 of, E84Q, E85K, E92Q, E97S, D126G, E167A and E102S;
liii. one or more of, such as 1, 2, 3, 4, 5, 6 or 7 of, E84Q, E85K, E92Q, E97S, D126G, E167A and E94S;
liv. one or more of, such as 1, 2, 3, 4, 5, 6 or 7 of, E84Q, E85K, E92Q, E97S, D126G, E167A and E71S;
lv. one or more of, such as 1, 2, 3, 4, 5, 6 or 7 of, E84Q, E85K, E92Q, E97S, D126G, E167A and E505;
lvi. one or more of, such as 1, 2, 3, 4, 5, 6 or 7 of, E76S, E84Q, E85K, E92Q, E97S, D126G and E167A;
lvii. one or more of, such as 1, 2, 3, 4, 5 or 6 of, E92N, E94N, E97N, D121N, D126N and E128N;
lviii. one or more of, such as 1, 2, 3, 4 or 5 of, E92N, E94N, E97N, D121N and D126N; or
lix. one or more of, such as 1, 2, 3, 4, 5 or 6 of, E84Q, E85K, E92Q, E97S, D126G and E167A In the above, the first letter refers to the amino acid in SEQ ID NO: 2 being replaced, the number is the position in SEQ ID NO: 2 and the second letter refers to the amino acid with which the first is to be substituted. Hence, E84D refers to substitution of glutamic acid (E) at position 84 with aspartic acid (D).

The variant may include any number of the substitutions in any one of i to lix, such as 1, 2, 3, 4, 5, 6 or 7. The variant preferably includes all of the substitutions shown in any one of i to lix above.

In a preferred embodiment, the variant comprises the substitutions in any one of i to xv above. The variant may include any number of the substitutions in any one of i to xv, such as 1, 2, 3, 4, 5, 6 or 7. The variant preferably includes all of the substitutions shown in any one of i to xv above.

If the one or more modifications are intended to improve the ability of the monomer to recognise or discriminate a polynucleotide, they are preferably made in addition to the modifications discussed above that improve polynucleotide capture, such as E84Q, E85K, E92Q, E97S, D126G and E167A.

The one or more modifications made to the identified region may concern the substitution of one or more amino acids in the region with amino acids present at the corresponding position(s) in homologues or paralogues of lysenin. Four examples of homologues of lysenin are shown in SEQ ID NOs: 14 to 17. The advantage of such substitutions is that they are likely to result in mutant monomers that form pores since the homologue monomers also form pores. For example, mutations may be made at any one or more of the positions in SEQ ID NO: 2 that differ between SEQ ID NO: 2 and any one of SEQ ID NOS: 14 to 17. Such a mutation may be a substitution of an amino acid in SEQ ID NO: 2 with an amino acid from the corresponding position in any one of SEQ ID NOS: 14 to 17, preferably in any one of SEQ ID NOs: 14 to 16. Alternatively, the mutation at any one of these positions may be a substitution with any amino acid, or may be a deletion or insertion mutation, such as substitutions, deletion or insertion of 1 to 30 amino acids such as of 2 to 20, 3 to 10 or 4 to 8 amino acids. Other than the mutations disclosed herein, and the mutations disclosed in the prior art, for example in WO 2013/153359, the amino acids that are conserved or identical between SEQ ID NO: 2 and all of SEQ ID NOs: 14 to 17, more preferably all of SEQ ID NOS: 14 to 16, are preferably conserved or present in a variant of the invention. Conservative mutations may be made at any one or more of these positions that are conserved or identical between SEQ ID NO: 2 and SEQ ID NOS: 14 to 17, or more preferably SEQ ID NOS: 14 to 16.

The invention provides a lysenin mutant monomer that comprises any one or more of the amino acids described herein as being substituted into a specific position of SEQ ID NO: 2 at a position in the structure of the lysenin monomer that corresponds to the specific position in SEQ ID NO: 2. Corresponding positions may be determined by standard techniques in the art. For example, the PILEUP and BLAST algorithms mentioned above can be used to align the sequence of a lysenin monomer with SEQ ID NO: 2 and hence to identify corresponding residues.

The mutant monomer typically retains the ability to form the same 3D structure as the wild type lysenin monomer, such as the same 3D structure as a lysenin monomer having the sequence of SEQ ID NO: 2. The 3D structure of the lysenin monomer is known in the art and is disclosed, for example, in the De Colbis et al., Structure, 2012 (20):1498-1507. The mutant monomer typically retains the ability to form a homooligomeric and/or a heterooligomeric pore with other lysenin monomers. The mutant monomer typically retains the ability to refold to form the same 3D structure as the wild-type lysenin monomer when present in a pore. The 3D structure of the lysenin monomer in a lysenin pore is shown in FIG. 7 herein. Any number of mutations, such as from 2 to 100, 3 to 80, 4 to 70, 5 to 60, 10 to 50 or 20 to 40, may be made in the wild-type lysenin sequence in addition to the mutations described herein, provided that the lysenin mutant monomer retains one or more of the improved properties imparted on it by the mutations of the invention.

Typically, the lysenin monomer will retain the ability to contribute two beta sheets to the barrel of the lysenin pore when it assembles with other identical mutant monomers, or with different lysenin mutant monomers to form a pore.

The variant further preferably comprises one or more of E84Q/E85K/E92Q/E97S/D126G or, where appropriate, all of E84Q/E85K/E92Q/E97S/D126G. By "where appropriate", we mean if the positions are still present in the mutant monomer or are not modified with a different amino acid.

In addition to the specific mutations discussed above, the variant may include other mutations. These mutations do not necessarily enhance the ability of the monomer to interact with a polynucleotide. The mutations may facilitate, for example, expression and/or purification. Over the entire length of the amino acid sequence of SEQ ID NO: 2, a variant will preferably be at least 50% homologous to that sequence based on amino acid similarity or identity. More preferably, the variant may be at least 55%, at least 60%, at least 65%, at least 70%, at least 75%, at least 80%, at least 85%, at least 90% and more preferably at least 95%, 97% or 99% homologous based on amino acid similarity or identity to the amino acid sequence of SEQ ID NO: 2 over the entire sequence. There may be at least 80%, for example at least 85%, 90% or 95%, amino acid similarity or identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) *Nucleic Acids Research* 12, p387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Centre for Biotechnology Information (www.ncbi.nlm.nih.gov/). Similarity can be measured using pairwise identity or by applying a scoring matrix such as BLOSUM62 and converting to an equivalent identity. Since they represent functional rather than evolved changes, deliberately mutated positions would be masked when determining homology. Similarity may be determined more sensitively by the application of position-specific scoring matrices using, for example, PSIBLAST on a comprehensive database of protein sequences. A different scoring matrix could be used that reflect amino acid chemico-physical properties rather than frequency of substitution over evolutionary time scales (e.g. charge).

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 3 below. Where amino acids have similar polarity, this can also be determined by reference to the hydropathy scale for amino acid side chains in Table 4.

TABLE 3

Chemical properties of amino acids

| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged (+) | Trp | aromatic, hydrophobic, neutral |
| Leu | aliphatic, hydrophobic, neutral | Tyr | aromatic, polar, hydrophobic |

TABLE 4

Hydropathy scale

| Side Chain | Hydropathy |
| --- | --- |
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

The variant may comprise one or more substitutions outside of the region specified above in which amino acids are replaced with those at the corresponding position(s) in homologues and paralogues of lysenin. Four examples of homologues of lysenin are shown in SEQ ID NOs: 14 to 17.

One or more amino acid residues of the amino acid sequence of SEQ ID NO: 2 may additionally be deleted from the variants described above. Up to 1, 2, 3, 4, 5, 10, 20 or 30 residues may be deleted, or more.

Variants may include fragments of SEQ ID NO: 2. Such fragments retain pore forming activity. This may be assayed as described above. Fragments may be at least 50, 100, 150, 200 or 250 amino acids in length. Such fragments may be used to produce the pores of the invention. Since the region of from about position 44 to about position 126 of SEQ ID NO: 2 can be modified by one or more deletions in accordance with the invention, a fragment does not have to contain the entire region. Hence, fragments shorter than the length of the unmodified region are envisaged by the invention. A fragment preferably comprises the pore forming domain of SEQ ID NO: 2. A fragment more preferably comprises the region from about position 44 to about position 126 of SEQ ID NO: 2 which is modified in accordance with the invention.

One or more amino acids may be alternatively or additionally added to the variants described above. An extension may be provided at the amino terminal or carboxy terminal of the amino acid sequence of the variant of SEQ ID NO: 2, including a fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO: 2 and which retains its ability to form a pore. A variant typically contains the region of SEQ ID NO: 2 that is responsible for pore formation, namely from about position 44 to about position 126 and this region is modified in accordance with the invention as discussed above. It may contain a fragment of this region as discussed above. In addition to the modifications of the invention, a variant of SEQ ID NO: 2 may include one or more additional modifications, such as substitutions, additions or deletions. These modifications are preferably located in the stretches in the variant that correspond to from about position 1 to about position 43 and from about position 127 to about position 297 of SEQ ID NO: 2 (i.e. outside of the region modified in accordance with the invention).

The mutant monomers may be modified to assist their identification or purification, for example by the addition of histidine residues (a hist tag), aspartic acid residues (an asp tag), a streptavidin tag or a flag tag, or by the addition of a signal sequence to promote their secretion from a cell where the polypeptide does not naturally contain such a sequence. An alternative to introducing a genetic tag is to chemically react a tag onto a native or engineered position on the pore. An example of this would be to react a gel-shift reagent to a cysteine engineered on the outside of the pore. This has been demonstrated as a method for separating hemolysin hetero-oligomers (Chem Biol. 1997 July; 4(7):497-505).

The mutant monomer may be labelled with a revealing label. The revealing label may be any suitable label which allows the pore to be detected. Suitable labels include, but are not limited to, fluorescent molecules, radioisotopes, e.g. $^{125}I$, $^{35}S$, enzymes, antibodies, antigens, polynucleotides, polyethylene glycols (PEGs), peptides and ligands such as biotin.

The mutant monomer may also be produced using D-amino acids. For instance, the mutant monomer may comprise a mixture of L-amino acids and D-amino acids. This is conventional in the art for producing such proteins or peptides.

The mutant monomer contains one or more specific modifications to facilitate interaction with a polynucleotide. The mutant monomer may also contain other non-specific modifications as long as they do not interfere with pore formation. A number of non-specific side chain modifications are known in the art and may be made to the side chains of the mutant monomer. Such modifications include, for example, reductive alkylation of amino acids by reaction with an aldehyde followed by reduction with $NaBH_4$, amidination with methylacetimidate or acylation with acetic anhydride.

The mutant monomer can be produced using standard methods known in the art. The monomer may be made synthetically or by recombinant means. For example, the monomer may be synthesized by in vitro translation and transcription (IVTT). Suitable methods for producing pore monomers are discussed in International Application Nos. PCT/GB09/001690 (published as WO 2010/004273), PCT/GB09/001679 (published as WO 2010/004265) or PCT/GB10/000133 (published as WO 2010/086603). Methods for inserting pores into membranes are discussed below.

Polynucleotide sequences encoding a mutant monomer may be derived and replicated using standard methods in the art. Such sequences are discussed in more detail below. Polynucleotide sequences encoding a mutant monomer may be expressed in a bacterial host cell using standard techniques in the art. The mutant monomer may be produced in a cell by in situ expression of the polypeptide from a recombinant expression vector. The expression vector optionally carries an inducible promoter to control the expression of the polypeptide.

A mutant monomer may be produced in large scale following purification by any protein liquid chromatography system from pore producing organisms or after recombinant expression as described below. Typical protein liquid chromatography systems include FPLC, AKTA systems, the Bio-Cad system, the Bio-Rad BioLogic system and the Gilson HPLC system. The mutant monomer may then be inserted into a naturally occurring or artificial membrane for use in accordance with the invention. Methods for inserting pores into membranes are discussed below.

In some embodiments, the mutant monomer is chemically modified. The mutant monomer can be chemically modified in any way and at any site. The mutant monomer is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. Suitable non-natural amino acids include, but are not limited to, 4-azido-L-phenylalanine (Faz) and any one of the amino acids numbered 1-71 in FIG. 1 of Liu C. C. and Schultz P. G., Annu. Rev. Biochem., 2010, 79, 413-444. The mutant monomer may be chemically modified by the attachment of any molecule. For instance, the mutant monomer may be chemically modified by attachment of a polyethylene glycol (PEG), a nucleic acid, such as DNA, a dye, a fluorophore or a chromophore.

In some embodiments, the mutant monomer is chemically modified with a molecular adaptor that facilitates the interaction between a pore comprising the monomer and a target analyte, a target nucleotide or target polynucleotide. The presence of the adaptor improves the host-guest chemistry of the pore and the nucleotide or polynucleotide and thereby improves the sequencing ability of pores formed from the mutant monomer. The principles of host-guest chemistry are well-known in the art. The adaptor has an effect on the physical or chemical properties of the pore that improves its interaction with the nucleotide or polynucleotide. The adaptor may alter the charge of the barrel or channel of the pore or specifically interact with or bind to the nucleotide or polynucleotide thereby facilitating its interaction with the pore.

The molecular adaptor is preferably a cyclic molecule, for example a cyclodextrin, a species that is capable of hybridization, a DNA binder or intercalator, a peptide or peptide analogue, a synthetic polymer, an aromatic planar molecule, a small positively-charged molecule or a small molecule capable of hydrogen-bonding.

The adaptor may be cyclic. A cyclic adaptor preferably has the same symmetry as the pore.

The adaptor typically interacts with the analyte, nucleotide or polynucleotide via host-guest chemistry. The adaptor is typically capable of interacting with the nucleotide or polynucleotide. The adaptor comprises one or more chemical groups that are capable of interacting with the nucleotide or polynucleotide. The one or more chemical groups preferably interact with the nucleotide or polynucleotide by non-covalent interactions, such as hydrophobic interactions, hydrogen bonding, Van der Waal's forces, rc-cation interactions and/or electrostatic forces. The one or more chemical groups that are capable of interacting with the nucleotide or polynucleotide are preferably positively charged. The one or more chemical groups that are capable of interacting with the nucleotide or polynucleotide more preferably comprise amino groups. The amino groups can be attached to primary, secondary or tertiary carbon atoms. The adaptor even more preferably comprises a ring of amino groups, such as a ring of 6, 7, 8 or 9 amino groups. The adaptor most preferably comprises a ring of 6 or 9 amino groups. A ring of protonated amino groups may interact with negatively charged phosphate groups in the nucleotide or polynucleotide.

The correct positioning of the adaptor within the pore can be facilitated by host-guest chemistry between the adaptor and the pore comprising the mutant monomer. The adaptor preferably comprises one or more chemical groups that are capable of interacting with one or more amino acids in the pore. The adaptor more preferably comprises one or more chemical groups that are capable of interacting with one or more amino acids in the pore via non-covalent interactions, such as hydrophobic interactions, hydrogen bonding, Van der Waal's forces, TC-cation interactions and/or electrostatic forces. The chemical groups that are capable of interacting with one or more amino acids in the pore are typically hydroxyls or amines. The hydroxyl groups can be attached to primary, secondary or tertiary carbon atoms. The hydroxyl groups may form hydrogen bonds with uncharged amino acids in the pore. Any adaptor that facilitates the interaction between the pore and the nucleotide or polynucleotide can be used.

Suitable adaptors include, but are not limited to, cyclodextrins, cyclic peptides and cucurbiturils. The adaptor is preferably a cyclodextrin or a derivative thereof. The cyclodextrin or derivative thereof may be any of those disclosed in Eliseev, A. V., and Schneider, H-J. (1994) *J. Am. Chem. Soc.* 116, 6081-6088. The adaptor is more preferably heptakis-6-amino-β-cyclodextrin (am$_7$-βCD), 6-monodeoxy-6-monoamino-β-cyclodextrin (am$_1$-βCD) or heptakis-(6-deoxy-6-guanidino)-cyclodextrin (gu$_7$-βCD). The guanidino group in guy-βCD has a much higher pKa than the primary amines in am$_7$-βCD and so it is more positively charged. This gu$_7$-βCD adaptor may be used to increase the dwell time of the nucleotide in the pore, to increase the accuracy of the residual current measured, as well as to increase the base detection rate at high temperatures or low data acquisition rates.

If a succinimidyl 3-(2-pyridyldithio)propionate (SPDP) crosslinker is used as discussed in more detail below, the adaptor is preferably heptakis(6-deoxy-6-amino)-6-N-mono (2-pyridyl)dithiopropanoyl-β-cyclodextrin (am$_6$amPDP$_1$-βCD).

More suitable adaptors include γ-cyclodextrins, which comprise 8 sugar units (and therefore have eight-fold symmetry). The γ-cyclodextrin may contain a linker molecule or may be modified to comprise all or more of the modified sugar units used in the β-cyclodextrin examples discussed above.

The molecular adaptor is preferably covalently attached to the mutant monomer. The adaptor can be covalently attached to the pore using any method known in the art. The adaptor is typically attached via chemical linkage. If the molecular adaptor is attached via cysteine linkage, the one or more cysteines have preferably been introduced to the mutant by substitution. The mutant monomers of the invention can of course comprise a cysteine residue at one or both of positions 272 and 283. The mutant monomer may be chemically modified by attachment of a molecular adaptor to one or both of these cysteines. Alternatively, the mutant monomer may be chemically modified by attachment of a molecule to one or more cysteines or non-natural amino acids, such as FAz, introduced at other positions.

The reactivity of cysteine residues may be enhanced by modification of the adjacent residues. For instance, the basic groups of flanking arginine, histidine or lysine residues will change the pKa of the cysteines thiol group to that of the more reactive S$^-$ group. The reactivity of cysteine residues may be protected by thiol protective groups such as dTNB. These may be reacted with one or more cysteine residues of the mutant monomer before a linker is attached. The molecule may be attached directly to the mutant monomer. The molecule is preferably attached to the mutant monomer using a linker, such as a chemical crosslinker or a peptide linker.

Suitable chemical crosslinkers are well-known in the art. Preferred crosslinkers include 2,5-dioxopyrrolidin-1-yl 3-(pyridin-2-yldisulfanyl)propanoate, 2,5-dioxopyrrolidin-1-yl 4-(pyridin-2-yldisulfanyl)butanoate and 2,5-dioxopyrrolidin-1-yl 8-(pyridin-2-yldisulfanyl)octananoate. The most preferred crosslinker is succinimidyl 3-(2-pyridyldithio)propionate (SPDP). Typically, the molecule is covalently attached to the bifunctional crosslinker before the molecule/crosslinker complex is covalently attached to the mutant monomer but it is also possible to covalently attach the bifunctional crosslinker to the monomer before the bifunctional crosslinker/monomer complex is attached to the molecule.

The linker is preferably resistant to dithiothreitol (DTT). Suitable linkers include, but are not limited to, iodoacetamide-based and maleimide-based linkers.

In other embodiment, the monomer may be attached to a polynucleotide binding protein. This forms a modular sequencing system that may be used in the methods of the invention. Polynucleotide binding proteins are discussed below.

The polynucleotide binding protein may be covalently attached to the mutant monomer. The protein can be covalently attached to the pore using any method known in the art. The monomer and protein may be chemically fused or genetically fused. The monomer and protein are genetically fused if the whole construct is expressed from a single polynucleotide sequence. Genetic fusion of a pore to a polynucleotide binding protein is discussed in International Application No. PCT/GB09/001679 (published as WO 2010/004265).

If the polynucleotide binding protein is attached via cysteine linkage, the one or more cysteines have preferably been introduced to the mutant by substitution. Such substitutions are typically made in loop regions which have low conservation amongst homologues indicating that mutations or insertions may be tolerated. They are therefore suitable for attaching a polynucleotide binding protein. Such substitutions are typically made in residues 1 to 43 and 127 to 297 of SEQ ID NO: 2. The reactivity of cysteine residues may be enhanced by modification as described above.

The polynucleotide binding protein may be attached directly to the mutant monomer or via one or more linkers. The polynucleotide binding protein may be attached to the mutant monomer using the hybridization linkers described in International Application No. PCT/GB10/000132 (published as WO 2010/086602). Alternatively, peptide linkers may be used. Peptide linkers are amino acid sequences. The length, flexibility and hydrophilicity of the peptide linker are typically designed such that it does not to disturb the functions of the monomer and molecule. Preferred flexible peptide linkers are stretches of 2 to 20, such as 4, 6, 8, 10 or 16, serine and/or glycine amino acids. More preferred flexible linkers include (SG)$_1$, (SG)$_2$, (SG)$_3$, (SG)$_4$, (SG)$_5$ and (SG)$_8$ wherein S is serine and G is glycine. Preferred rigid linkers are stretches of 2 to 30, such as 4, 6, 8, 16 or 24, proline amino acids. More preferred rigid linkers include (P)$_{12}$ wherein P is proline.

The mutant monomer may be chemically modified with a molecular adaptor and a polynucleotide binding protein.

Making Mutant Lysenin Monomers

The invention also provides a method of improving the ability of a lysenin monomer comprising the sequence shown in SEQ ID NO: 2 to characterise a polynucleotide.

The method comprises making one or more modifications and/or substitutions of the invention in SEQ ID NO: 2. Any of the embodiments discussed above with reference to the mutant lysenin monomers and below with reference to characterising polynucleotides equally apply to this method of the invention.

Constructs

The invention also provides a construct comprising two or more covalently attached monomers derived from lysenin wherein at least one of the monomers is a mutant lysenin monomer of the invention. The construct of the invention retains its ability to form a pore. One or more constructs of the invention may be used to form pores for characterising a target analyte. One or more constructs of the invention may be used to form pores for characterising a target polynucleotide, such as sequencing a target polynucleotides. The construct may comprise 2, 3, 4, 5, 6, 7, 8, 9 or 10 or more monomers. The two or more monomers may be the same or different.

At least monomer in the construct is a mutant monomer of the invention. 2 or more, 3 or more, 4 or more, 5 or more, 6 or more, 7 or more, 8 or more, 9 or more or 10 or more monomers in the construct may be mutant monomers of the invention. All of the monomers in the construct are preferably mutant monomers of the invention. The mutant monomers may be the same or different. In a preferred embodiment, the construct comprises two mutant monomers of the invention.

The mutant monomers of the invention in the construct are preferably approximately the same length or are the same length. The barrels of the mutant monomers of the invention in the construct are preferably approximately the same length or are the same length. Length may be measured in number of amino acids and/or units of length. The mutant monomers of the invention in the construct preferably have the same number of amino acids deleted from positions 34 to 70 and/or positions 71 to 107 as described above.

The other monomers in the construct do not have to be mutant monomers of the invention. For instance, at least one monomer may comprise the sequence shown in SEQ ID NO: 2. At least one monomer in the construct may be a paralogue or homologue of SEQ ID NO: 2. Suitable homologues are shown in SEQ ID NOs: 14 to 17.

Alternatively, at least one monomer may comprise a variant of SEQ ID NO: 2 which is at least 50% homologous to SEQ ID NO: 2 over its entire sequence based on amino acid identity, but does not include any of the specific mutations required by the mutant monomers of the invention or in which no amino acids have been deleted as described above. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. The variant may be a fragment or any other variant discussed above. Constructs of the invention may also comprise a variant of SEQ ID NO: 14, 15, 16 or 17 which is at least 50% homologous or at least any of the other level of homology mentioned above to SEQ ID NO: 14, 15, 16 or 17 over its entire sequence based on amino acid identity.

All of the monomers in the construct may be a mutant monomer of the invention. The mutant monomers may be the same or different. In a more preferred embodiment, the construct comprises two monomers and at least one of the monomers is a mutant monomer of the invention.

The monomers may be genetically fused. Monomers are genetically fused if the whole construct is expressed from a single polynucleotide sequence. The coding sequences of the monomers may be combined in any way to form a single polynucleotide sequence encoding the construct. Genetic fusion is discussed in International Application No. PCT/GB09/001679 (published as WO 2010/004265).

The monomers may be genetically fused in any configuration. The monomers may be fused via their terminal amino acids. For instance, the amino terminus of the one monomer may be fused to the carboxy terminus of another monomer.

The two or more monomers may be genetically fused directly together. The monomers are preferably genetically fused using a linker. The linker may be designed to constrain the mobility of the monomers. Preferred linkers are amino acid sequences (i.e. peptide linkers). Any of the peptide linkers discussed above may be used.

The length, flexibility and hydrophilicity of the peptide linker are each typically designed such that they do not to disturb the functions of the monomer and molecule. Preferred flexible peptide linkers are stretches of 2 to 20, such as 4, 6, 8, 10 or 16, serine and/or glycine amino acids. More preferred flexible linkers include $(SG)_1$, $(SG)_2$, $(SG)_3$, $(SG)_4$, $(SG)_5$ and $(SG)_8$ wherein S is serine and G is glycine. Preferred rigid linkers are stretches of 2 to 30, such as 4, 6, 8, 16 or 24, proline amino acids. More preferred rigid linkers include $(P)_{12}$ wherein P is proline.

In another preferred embodiment, the monomers are chemically fused. Monomers are chemically fused if they are chemically attached, for instance via a chemical cross-linker. Any of the chemical crosslinkers discussed above may be used. The linker may be attached to one or more cysteine residues or non-natural amino acids, such as Faz, introduced into a mutant monomer Alternatively, the linker may be attached to a terminus of one of the monomers in the construct. Monomers are typically linked via one or more of residues 1 to 43 and 127 to 297 of SEQ ID NO: 2.

If a construct contains different monomers, crosslinkage of monomers to themselves may be prevented by keeping the concentration of linker in a vast excess of the monomers. Alternatively, a "lock and key" arrangement may be used in which two linkers are used. Only one end of each linker may react together to form a longer linker and the other ends of the linker each react with a different monomers. Such linkers are described in International Application No. PCT/GB10/000132 (published as WO 2010/086602).

The invention also provides a method of producing a construct of the invention. The method comprises covalently attaching at least one mutant lysenin monomer of the invention to one or more monomers derived from lysenin. Any of the embodiments discussed above with reference to the construct of the invention equally apply to the methods of producing the constructs.

Polynucleotides

The present invention also provides polynucleotide sequences which encode a mutant monomer of the invention. The mutant monomer may be any of those discussed above. The polynucleotide sequence preferably comprises a sequence at least 50%, 60%, 70%, 80%, 90% or 95% homologous based on nucleotide identity to the sequence of SEQ ID NO: 1 over the entire sequence. There may be at least 80%, for example at least 85%, 90% or 95% nucleotide identity over a stretch of 300 or more, for example 375, 450, 525 or 600 or more, contiguous nucleotides ("hard homology"). Homology may be calculated as described above. The polynucleotide sequence may comprise a sequence that differs from SEQ ID NO: 1 on the basis of the degeneracy of the genetic code.

The present invention also provides polynucleotide sequences which encode any of the genetically fused constructs of the invention. The polynucleotide preferably comprises two or more sequences as shown in SEQ ID NO: 1 or a variant thereof as described above.

Polynucleotide sequences may be derived and replicated using standard methods in the art. Chromosomal DNA encoding wild-type Lysenin may be extracted from a pore producing organism, such as *Eisenia fetida*. The gene encoding the pore monomer may be amplified using PCR involving specific primers. The amplified sequence may then undergo site-directed mutagenesis. Suitable methods of site-directed mutagenesis are known in the art and include, for example, combine chain reaction. Polynucleotides encoding a construct of the invention can be made using well-known techniques, such as those described in Sambrook, J. and Russell, D. (2001). Molecular Cloning: A Laboratory Manual, 3rd Edition. Cold Spring Harbor Laboratory Press, Cold Spring Harbor, N.Y.

The resulting polynucleotide sequence may then be incorporated into a recombinant replicable vector such as a cloning vector. The vector may be used to replicate the polynucleotide in a compatible host cell. Thus polynucleotide sequences may be made by introducing a polynucleotide into a replicable vector, introducing the vector into a compatible host cell, and growing the host cell under conditions which bring about replication of the vector. The vector may be recovered from the host cell. Suitable host cells for cloning of polynucleotides are known in the art and described in more detail below.

The polynucleotide sequence may be cloned into a suitable expression vector. In an expression vector, the polynucleotide sequence is typically operably linked to a control sequence which is capable of providing for the expression of the coding sequence by the host cell. Such expression vectors can be used to express a pore subunit.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Multiple copies of the same or different polynucleotide sequences may be introduced into the vector.

The expression vector may then be introduced into a suitable host cell. Thus, a mutant monomer or construct of the invention can be produced by inserting a polynucleotide sequence into an expression vector, introducing the vector into a compatible bacterial host cell, and growing the host cell under conditions which bring about expression of the polynucleotide sequence. The recombinantly-expressed monomer or construct may self-assemble into a pore in the host cell membrane. Alternatively, the recombinant pore produced in this manner may be removed from the host cell and inserted into another membrane. When producing pores comprising at least two different subunits, the different subunits may be expressed separately in different host cells as described above, removed from the host cells and assembled into a pore in a separate membrane, such as a sheep erythrocyte membrane or liposomes containing sphingomyelin.

For example, lysenin monomers may be oligomerised by adding a lipid mixture comprising sphingomyelin and one ore more of the following lipids: phosphatidylserine; POPE; Cholesterol; and Soy PC and incubating the mixture, for example at 30° C. for 60 minutes. The oligomerised monomers may be purified by any suitable method, for example by SDS-PAGE and gel purification as described in WO2013/153359.

The vectors may be for example, plasmid, virus or phage vectors provided with an origin of replication, optionally a promoter for the expression of the said polynucleotide sequence and optionally a regulator of the promoter. The vectors may contain one or more selectable marker genes, for example a tetracycline resistance gene. Promoters and other expression regulation signals may be selected to be compatible with the host cell for which the expression vector is designed. A T7, trc, lac, ara or $\lambda_L$ promoter is typically used.

The host cell typically expresses the pore subunit at a high level. Host cells transformed with a polynucleotide sequence will be chosen to be compatible with the expression vector used to transform the cell. The host cell is typically bacterial and preferably *Escherichia coli*. Any cell with a λ DE3 lysogen, for example C41 (DE3), BL21 (DE3), JM109 (DE3), B834 (DE3), TUNER, Origami and Origami B, can express a vector comprising the T7 promoter. In addition to the conditions listed above any of the methods cited in Proc Natl Acad Sci USA. 2008 Dec. 30; 105(52):20647-52 may be used to express the lysenin proteins.

Pores

The invention also provides various pores. The pores of the invention are ideal for characterising analytes. The pores of the invention are especially ideal for characterising, such as sequencing, polynucleotides because they can discriminate between different nucleotides with a high degree of sensitivity. The pores can be used to characterise nucleic acids, such as DNA and RNA, including sequencing the nucleic acid and identifying single base changes. The pores of the invention can even distinguish between methylated and unmethylated nucleotides. The base resolution of pores of the invention is surprisingly high. The pores show almost complete separation of all four DNA nucleotides. The pores can be further used to discriminate between deoxycytidine monophosphate (dCMP) and methyl-dCMP based on the dwell time in the pore and the current flowing through the pore.

The pores of the invention can also discriminate between different nucleotides under a range of conditions. In particular, the pores will discriminate between nucleotides under conditions that are favourable to the characterising, such as sequencing, of polynucleotides. The extent to which the pores of the invention can discriminate between different nucleotides can be controlled by altering the applied potential, the salt concentration, the buffer, the temperature and the presence of additives, such as urea, betaine and DTT. This allows the function of the pores to be fine-tuned, particularly when sequencing. This is discussed in more detail below. The pores of the invention may also be used to identify polynucleotide polymers from the interaction with one or more monomers rather than on a nucleotide by nucleotide basis.

A pore of the invention may be isolated, substantially isolated, purified or substantially purified. A pore of the invention is isolated or purified if it is completely free of any other components, such as lipids or other pores. A pore is substantially isolated if it is mixed with carriers or diluents which will not interfere with its intended use. For instance, a pore is substantially isolated or substantially purified if it is present in a form that comprises less than 10%, less than 5%, less than 2% or less than 1% of other components, such as lipids or other pores. Alternatively, a pore of the invention may be present in a lipid bilayer.

A pore of the invention may be present as an individual or single pore. Alternatively, a pore of the invention may be present in a homologous or heterologous population or plurality of two or more pores.

Homo-Oligomeric Pores

The invention also provides a homo-oligomeric pore derived from lysenin comprising identical mutant monomers of the invention. The monomers are identical in terms of their amino acid sequence. The homo-oligomeric pore of the invention is ideal for characterising, such as sequencing, polynucleotides. The homo-oligomeric pore of the invention may have any of the advantages discussed above. The advantages of specific homo-oligomeric pores of the invention are indicated in the Examples.

The homo-oligomeric pore may contain any number of mutant monomers. The pore typically comprises two or more mutant monomers. The homo-oligomeric pore may contain any number of mutant monomers. The pore typically comprises at least 6, at least 7, at least 8, at least 9 or at least 10 identical mutant monomers, such as 6, 7, 8, 9 or 10 mutant monomers. The pore preferably comprises eight or nine identical mutant monomers. The pore most preferably comprises nine identical mutant monomers. This number of monomers is referred to herein as a "sufficient number".

One or more, such as 2, 3, 4, 5, 6, 7, 8, 9 or 10, of the mutant monomers is preferably chemically modified as discussed above or below.

One or more of the mutant monomers is preferably chemically modified as discussed above or below. In other words, one or more of the monomers being chemically modified (and the others not being chemically modified) does not prevent the pore from being homo-oligomeric as long as the amino acid sequence of each of the monomers is identical.

Methods for making lysenin pores are described in the Examples and in Yamaji et al., J. Biol. Chem. 1998; 273(9): 5300-6.

Hetero-Oligomeric Pores

The invention also provides a hetero-oligomeric pore derived from lysenin comprising at least one mutant monomer of the invention, wherein at least one of the monomers differs from the others. The monomer differs from the others in terms of its amino acid sequence. The hetero-oligomeric pore of the invention is ideal for characterising, such as sequencing, polynucleotides. Hetero-oligomeric pores can be made using methods known in the art (e.g. Protein Sci. 2002 July; 11(7):1813-24).

The hetero-oligomeric pore contains sufficient monomers to form the pore. The monomers may be of any type, including, for example, wild-type. The pore typically comprises two or more monomers. The pore typically comprises at least 6, at least 7, at least 8, at least 9 or at least 10 monomers, such as 6, 7, 8, 9 or 10 monomers. The pore preferably comprises eight or nine monomers. The pore most preferably comprises nine monomers. This number of monomers is referred to herein as a "sufficient number".

The pore may comprise at least one monomer comprising the sequence shown in SEQ ID NO: 2, a paralogue thereof, a homologue thereof or a variant thereof which does not have a mutation required by the mutant monomers of the invention or in which no amino acids have been deleted as described above. Suitable variants are any of those discussed above with reference to the constructs of the invention, including SEQ ID NOs: 2, 14, 15, 16 and 17 and variants thereof. In this embodiment, the remaining monomers are preferably mutant monomers of the invention.

In a preferred embodiment, the pore comprises (a) one mutant monomer of the invention and (b) a sufficient number of identical monomers to form the pore, wherein the mutant monomer in (a) is different from the identical monomers in (b). The identical monomers in (b) preferably comprise the sequence shown in SEQ ID NO: 2, a paralogue thereof, a homologue thereof or a variant thereof which does not have a mutation required by the mutant monomers of the invention.

A hetero-oligomeric pore of the invention preferably comprises only one mutant lysenin monomer of the invention.

In another preferred embodiment, all of the monomers in the hetero-oligomeric pore are mutant monomers of the invention and at least one of them differs from the others.

The mutant monomers of the invention in the pore are preferably approximately the same length or are the same length. The barrels of the mutant monomers of the invention in the pore are preferably approximately the same length or are the same length. Length may be measured in number of amino acids and/or units of length. The mutant monomers of the invention in the pore preferably have the same number of amino acids deleted from positions 34 to 70 and/or positions 71 to 107.

In all the embodiments discussed above, one or more of the mutant monomers is preferably chemically modified as discussed above or below. The presence of a chemical modification on one monomer does not result in the pore being hetero-oligomeric. The amino acid sequence of at least one monomer must differ from the sequence(s) of the other monomers. Methods for making pores are discussed in more detail below.

Construct-Containing Pores

The invention also provides a pore comprising at least one construct of the invention. A construct of the invention comprises two or more covalently attached monomers derived from lysenin, wherein at least one of the monomers is a mutant lysenin monomer of the invention. In other words, a construct must contain more than one monomer. At least two of the monomers in the pore are in the form of a construct of the invention. The monomers may be of any type.

A pore typically contains (a) one construct comprising two monomers and (b) a sufficient number of monomers to form the pore. The construct may be any of those discussed above. The monomers may be any of those discussed above, including mutant monomers of the invention.

Another typical pore comprises more than one construct of the invention, such as two, three or four constructs of the invention. Such pores further comprise a sufficient number of monomers to form the pore. The monomer may be any of those discussed above. A further pore of the invention comprises only constructs comprising 2 monomers. A specific pore according to the invention comprises several constructs each comprising two monomers. The constructs may oligomerise into a pore with a structure such that only one monomer from each construct contributes to the pore. Typically, the other monomers of the construct (i.e. the ones not forming the pore) will be on the outside of the pore.

Mutations can be introduced into the construct as described above. The mutations may be alternating, i.e. the mutations are different for each monomer within a two monomer construct and the constructs are assembled as a homo-oligomer resulting in alternating modifications. In other words, monomers comprising MutA and MutB are fused and assembled to form an A-B:A-B:A-B:A-B pore. Alternatively, the mutations may be neighbouring, i.e. identical mutations are introduced into two monomers in a construct and this is then oligomerised with different mutant monomers. In other words, monomers comprising MutA are fused follow by oligomerisation with MutB-containing monomers to form A-A:B:B:B:B:B:B.

One or more of the monomers of the invention in a construct-containing pore may be chemically-modified as discussed above or below.

Chemically-Modified Pores of the Invention

In another aspect, the invention provides a chemically-modified lysenin pore comprising one or more mutant monomers which are chemically modified such that the open diameter of the barrel/channel of an assembled pore is reduced, narrowed or constricted at one site or more along the length of the barrel; such as two, three, four or five sites. The pore may comprise any number of monomers discussed above with reference to the homo-oligomeric and hetero-oligomeric pores of the invention. The pore preferably comprises nine chemically-modified monomers. The chemically-modified pore may be homo-oligomeric as described above. In other words, all of the monomers in the chemically-modified pore may have the same amino acid sequence and be chemically modified in the same way. The chemically-modified pore may be hetero-oligomeric as described above. In other words, the pore may comprise (a) only one monomer which is chemically modified, (b) more than one, such as two, three, four, five, six, seven or eight, chemically-modified monomers in which at least two, such as three, four, five, six or seven, of the chemically-modified monomers differ from one another or (c) only chemically-modified monomers (i.e. all of the monomers are chemically modified) in which at least two, such as three, four, five, six, seven, eight or nine, of the chemically-modified monomers differ from one another. The monomers may differ from one another in terms of their amino acid sequences, their chemical modifications or both their amino acid sequences and their chemical modifications. The chemically-modified monomer(s) may be any of theose discussed above and/or below.

The invention also provides a mutant lysenin monomer that is chemically-modified in any of the ways discussed below. The mutant monomer may be any of those discussed above or below. As a result, a mutant monomer of the invention, such as a variant of SEQ ID NO: 2 comprising a modification at one or more of the following positions K37, G43, K45, V47, S49, T51, H83, V88, T91, T93, V95, Y96, S98, K99, V100, I101, P108, P109, T110, S111, K112 and T114 or a variant comprising the barrel deletions discussed above, may be chemically-modified in accordance with the invention as discussed below.

The mutant monomer can be chemically-modified such that the diameter of the barrel of an assembled pore is reduced or narrowed by any factor of reduction which is dependent on the size of the analyte to be passed through the pore. The width of the constriction zone will typically determine the extent of disruption of the measurement signal during translocation of the analyte due to for example the analyte reducing the ion flow through the pore. The greater the disruption in signal, typically the greater the sensitivity in measurement. Thus the constriction zone may be chosen to be slightly wider than the analyte to be translocated. For translocation for example of ssDNA, the width of the constriction zone may be chosen from a value in the range of 0.8 to 3.0 nm.

Chemical modification may also determine the length of the constriction zone which in turn will determine the number of polymer units, for example nucleotides, that contribute to the measurement signal. The nucleotides that contribute to the current signal at any particular time may be referred to as a k-mer where k is an integer and which may be a whole or fractional number. In the case of measurement of a polynucleotide having 4 types of nucleobase, a 3-mer will give rise to $4^3$ potential signal levels. Larger values of k give rise to a greater number of signal levels. Typically it is desirable to provide a short constriction zone as this simplifies analysis of the measurement signal data.

The chemical modification is such that a chemical molecule is preferably covalently attached to the mutant monomer or the one or more mutant monomers. The chemical molecule can be covalently attached to the pore, mutant monomer or one or more mutant monomers using any method known in the art. The chemical molecule is typically attached via chemical linkage.

The mutant monomer or one or more mutant monomers is/are preferably chemically modified by attachment of a molecule to one or more cysteines (cysteine linkage), attachment of a molecule to one or more lysines, attachment of a molecule to one or more non-natural amino acids or enzyme modification of an epitope. If the chemical modifier is attached via cysteine linkage, the one or more cysteines have preferably been introduced to the mutant by substitution. Suitable methods for carrying out such modifications are well-known in the art. Suitable non-natural amino acids include, but are not limited to, 4-azido-L-phenylalanine (Faz) and any one of the amino acids numbered 1-71 in FIG. 1 of Liu C. C. and Schultz P. G., Annu. Rev. Biochem., 2010, 79, 413-444.

The mutant monomer or one or more mutant monomers may be chemically modified by the attachment of any molecule which has the effect of reducing or narrowing the diameter of the barrel of an assembled pore at any location or site. For instance, the mutant monomer may be chemically modified by attachment of (i) Maleimides such as: 4-phenylazomaleinanil, 1,N-(2-Hydroxyethyl)maleimide, N-Cyclohexylmaleimide, 1,3-Maleimidopropionic Acid, 1,1-4-Aminophenyl-1H-pyrrole,2,5,dione, 1,1-4-Hydroxyphenyl-1H-pyrrole,2,5,dione, N-Ethylmaleimide, N-Methoxycarbonylmaleimide N-tert-Butylmaleimide, N-(2-Aminoethy)maleinide, 3-Maleimido-PROXYL, N-(4-Chlorophenyl)maleimide, 1-[4-(dimethylamino)-3,5-dinitrophenyl]-1H-pyrrole-2,5-dione, N-[4-(2-Benizmidazolyl)phenyl]maleimide, N-[4-(2-benzoxazoyl)phenyl]maleimide, N-(1 NAPHTHYL)-MALEIMIDE, N-(2,4-XYLYL)MALEIMIDE, N-(2,4-DIFLUOROPHENYL)MALEIMIDE, N-(3-CHLORO-PARA-TOLYL)-MALEIMIDE, 1-(2-Amino-ethyl)-pyrrole-2,5-dione hydrochloride, 1-cyclopentyl-3-methyl-2,5-dihydro-1H-pyrrole-2,5-dione, 1-(3-aminopropyl)-2,5-dihydro-1H-pyrrole-2,5-dione hydrochloride, 3-methyl-1-[2-ox-2-(piperazin-1-yl)ethyl]-2,5-dihydro-1-H-pyrrole-2,5-dione hydrochloride, 1-benzyl-2,5-dihydro-1H-pyrrole-2,5-dione, 3-methyl-1-(3,3,3-trifluropropyl)-2,5-dihydro-1H-pyrrole-2,5-dione, 1-[4-(methylamino)cyclohexyl]-2,5-dihydro-1H-pyrrole-2,5-dione trifluroacetic acid. SMILES O=C1C=CC(=O)N1CC=2C=CN=CC2, SMILES O=C1C=CC(=O)N1CN2CCNCC2. 1-benzyl-3-methyl-2,5-dihydro-1H-pyrrole-2,5-dione, 1-(2-fluorophenyl)-3-methyl-2,5-dihydro 1H-pyrrole-2,5-dione, N-(4-PHENOXYPHENYL)MALEIMIDE, N-(4-NITROPHENYL) MALEIMIDE; (ii) Iodocetamides such as: 3-(2-Iodoacetamido)-PROXYL, N-(cyclopropylmethyl)-2- iodoacetamide, 2-iodo-N-(2-phenylethyl)acetamide, 2-iodo-N-(2,2,2-trifluoroethyl)acetamide, N-(4-ACETYLPHENYL)-2-IODOACETAMIDE, N-(4-(AMINOSULFONYL)PHENYL)-2-IODOACETAMIDE, N-(1,3-BENZOTHIAZOL-2-YL)-2-IODOACETAMIDE, N-(2,6-DIETHYLPHENYL)-2-IODOACETAMIDE, N-(2-benzoyl-4-chlorophenyl)-2-iodoacetamide; (iii) Bromoacetamides: such as N-(4-(ACETYLAMINO)PHENYL)-2-BROMOACETAMIDE, N-(2-ACETYLPHENYL)-2-BROMOACETAMIDE, 2-BROMO-N-(2-CYANOPHENYL)ACETAMIDE, 2-BROMO-N-(3-(TRIFLUOROMETHYL)PHENYL)ACETAMIDE, N-(2-benzoylphenyl)-2-bromoacetamide, 2-bromo-N-(4-fluorophenyl)-3-methylbutanamide, N-Benzyl-2-bromo-N-phenylpropionamide, N-(2-BROMO-BUTYRYL)-4-CHLORO-BENZENESULFONAMIDE, 2-Bromo-N-methyl-N-phenylacetamide, 2-bromo-N-phenethyl-acetartide. 2-ADAMANTAN-1-YL-2-BROMO-N-CYCLOHEXYL-ACETAMIDE, 2-bromo-N-(2-methylphenyl)butanamide, Monobromoacetanilide; (iv) Disulphides such as: ALDRITHIOL-2, ALDRITHIOL-4, ISOPROPYL DISULFIDE, 1-(Isobutyldisulfanyl)-2-methylpropane, Dibenzyl disulfide, 4-AMINOPHENYL DISULFIDE, 3-(2-Pyridyldithio)propionic acid, 3-(2-Pyridyldithio)propionic acid hydrazide, 3-(2-Pyridyldithio)propionic acid N-succinimidyl ester, am6amPDP1-βCD; and (v) Thiols such as: 4-Phenylthiazole-2-thiol, Purpald, 5,6,7,8-TETRAHYDRO-QUINAZOLINE-2-THIOL.

The mutant monomer or one or more mutant monomers may be chemically modified by attachment of polyethylene glycol (PEG), a nucleic acid, such as DNA, a dye, a fluorophore or a chromophore. In some embodiments, the mutant monomer or one or more mutant monomers is/are chemically modified with a molecular adaptor that facilitates the interaction between a pore comprising the monomer and a target analyte, a target nucleotide or target polynucleotide. The presence of the adaptor improves the host-guest chemistry of the pore and the nucleotide or polynucleotide and thereby improves the sequencing ability of pores formed from the mutant monomer.

The mutant monomer or one or more mutant monomers may be chemically modified by the attachment of any molecule which has the effect of reducing or narrowing the open diameter of the barrel of an assembled pore at any of positions: K37, V47, S49, T55, S86, E92, E94. More preferably the mutant monomer may be chemically modified by the attachment of any molecule which has the effect of reducing or narrowing the open diameter of the barrel of an assembled pore at positions E92 and E94. In one embodiment the mutant monomer or one or more mutant monomers is/are chemically modified by attachment of a molecule to one or more cysteines (cysteine linkage) at these positions.

The reactivity of cysteine residues may be enhanced by modification of the adjacent residues. For instance, the basic groups of flanking arginine, histidine or lysine residues will change the pKa of the cysteines thiol group to that of the more reactive S$^-$ group. The reactivity of cysteine residues may be protected by thiol protective groups such as dTNB. These may be reacted with one or more cysteine residues of the mutant monomer before a linker is attached.

The molecule may be attached directly to the mutant monomer or the one or more mutant monomers. The molecule is preferably attached to the mutant monomer using a linker, such as a chemical crosslinker or a peptide linker. Suitable chemical crosslinkers are well-known in the art. Preferred crosslinkers include 2,5-dioxopyrrolidin-1-yl 3-(pyridin-2-yldisulfanyl)propanoate, 2,5-dioxopyrrolidin-1-yl 4-(pyridin-2-yldisulfanyl)butanoate and 2,5-dioxopyrrolidin-1-yl 8-(pyridin-2-yldisulfanyl)octananoate. The most preferred crosslinker is succinimidyl 3-(2-pyridyldithio)propionate (SPDP). Typically, the molecule is covalently attached to the bifunctional crosslinker before the molecule/crosslinker complex is covalently attached to the mutant monomer but it is also possible to covalently attach the bifunctional crosslinker to the monomer before the bifunctional crosslinker/monomer complex is attached to the molecule.

The linker is preferably resistant to dithiothreitol (DTT). Suitable linkers include, but are not limited to, iodoacetamide-based and maleimide-based linkers.

The pores chemically modified in this way show the specific advantage of (i) improvements to the sharpness of the read head (ii) improved discrimination between bases and (iii) improved range i.e., improved signal to noise ratio.

By modifying a particular position within the barrel with a chemical molecule a new reader-head can be introduced or an old reader head can be modified. Due to the size of the modified molecule, the physical size of the reader head can be altered significantly. Similarly, due to the chemical nature of the modified molecule, properties of the reader-head can be altered. Combination of the two effects has been demonstrated to result in a reader-head with improved resolution and better discrimination of bases. Not only has the relative contribution to the signal of different bases at different positions been altered, read-head positions at the extreme show much less discrimination meaning their contribution toward the signal is much reduced and therefore the length of the Kmer being assayed at a given moment is shorter. This sharper read-head makes the process of deconvolution of Kmers from raw signal simpler.

Producing Pores of the Invention

The invention also provides a method of producing a pore of the invention. The method comprises allowing at least one mutant monomer of the invention or at least one construct of the invention to oligomerise with a sufficient number of mutant lysenin monomers of the invention, constructs of the invention, lysenin monomers or monomers derived from lysenin to form a pore. If the method concerns making a homo-oligomeric pore of the invention, all of the monomers used in the method are mutant lysenin monomers of the invention having the same amino acid sequence. If the method concerns making a hetero-oligomeric pore of the invention, at least one of the monomers is different from the others.

Typically, the monomers are expressed in host cells as described above, removed from the host cells and assembled into a pore in a separate membrane, such as a sheep erythrocyte membrane or liposomes containing sphingomyelin.

For example, lysenin monomers may be oligomerised by adding a lipid mixture comprising sphingomyelin and one ore more of the following lipids: phosphatidylserine; POPE; Cholesterol; and Soy PC and incubating the mixture, for example at 30° C. for 60 minutes. The oligomerised monomers may be purified by any suitable method, for example by SDS-PAGE and gel purification as described in WO2013/153359.

Any of the embodiments discussed above with reference to the pores of the invention equally apply to the methods of producing the pores.

Methods of Characterising Analytes

The invention provides a method of characterising a target analyte. The method comprises contacting the target analyte with a pore of the invention such that the target analyte moves through the pore. The pore may be any of those discussed above. One or more characteristics of the target analyte are then measured as the analyte moves with respect to the pore using standard methods known in the art. One or more characteristics of the target analyte are preferably measured as the analyte moves through the pore. Steps (a) and (b) are preferably carried out with a potential applied across the pore. As discussed in more detail below, the applied potential typically results in the formation of a complex between the pore and a polynucleotide binding protein. The applied potential may be a voltage potential. Alternatively, the applied potential may be a chemical potential. An example of this is using a salt gradient across an amphiphilic layer. A salt gradient is disclosed in Holden et al., J Am Chem Soc. 2007 Jul. 11; 129(27):8650-5.

The method of the invention is for characterising a target analyte. The method is for characterising at least one analyte. The method may concern characterising two or more analytes. The method may comprise characterising any number of analytes, such as 2, 5, 10, 15, 20, 30, 40, 50, 100 or more analytes.

The target analyte is preferably a metal ion, an inorganic salt, a polymer, an amino acid, a peptide, a polypeptide, a protein, a nucleotide, an oligonucleotide, a polynucleotide, a dye, a bleach, a pharmaceutical, a diagnostic agent, a recreational drug, an explosive or an environmental pollutant. The method may concern characterising two or more analytes of the same type, such as two or more proteins, two or more nucleotides or two or more pharmaceuticals. Alternatively, the method may concern characterising two or more analytes of different types, such as one or more proteins, one or more nucleotides and one or more pharmaceuticals.

The target analyte can be secreted from cells. Alternatively, the target analyte can be an analyte that is present inside cells such that the analyte must be extracted from the cells before the invention can be carried out.

The analyte is preferably an amino acid, a peptide, a polypeptides and/or a protein. The amino acid, peptide, polypeptide or protein can be naturally-occurring or non-naturally-occurring. The polypeptide or protein can include within them synthetic or modified amino acids. A number of different types of modification to amino acids are known in the art. Suitable amino acids and modifications thereof are above. For the purposes of the invention, it is to be understood that the target analyte can be modified by any method available in the art.

The protein can be an enzyme, an antibody, a hormone, a growth factor or a growth regulatory protein, such as a cytokine. The cytokine may be selected from interleukins, preferably IFN-1, IL-1, IL-2, IL-4, IL-5, IL-6, IL-10, IL-12 and IL-13, interferons, preferably IL-$\gamma$, and other cytokines such as TNF-$\alpha$. The protein may be a bacterial protein, a fungal protein, a virus protein or a parasite-derived protein.

The target analyte is preferably a nucleotide, an oligonucleotide or a polynucleotide. A nucleotide typically contains a nucleobase, a sugar and at least one phosphate group. The nucleobase is typically heterocyclic. Nucleobases include, but are not limited to, purines and pyrimidines and more specifically adenine, guanine, thymine, uracil and cytosine. The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), 5-methylcytidine monophosphate, 5-methylcytidine diphosphate, 5-methylcytidine triphosphate, 5-hydroxymethylcytidine monophosphate, 5-hydroxymethylcytidine diphosphate, 5-hydroxymethylcytidine triphosphate, cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP), 5-methyl-2'-deoxycytidine monophosphate, 5-methyl-2'-deoxycytidine diphosphate, 5-methyl-2'-deoxycytidine triphosphate, 5-hydroxymethyl-2'-deoxycytidine monophosphate, 5-hydroxymethyl-2'-deoxycytidine diphosphate and 5-hydroxymethyl-2'-deoxycytidine triphosphate. The nucleotides are preferably selected from AMP, TMP, GMP, UMP, dAMP, dTMP, dGMP or dCMP. The nucleotides may be abasic (i.e. lack a nucleobase). The nucleotides may contain additional modifications. In particular, suitable modified nucleotides include, but are not limited to, 2'amino pyrimidines (such as 2'-amino cytidine and 2'-amino uridine), 2'-hydroxyl purines (such as, 2'-fluoro pyrimidines (such as 2'-fluorocytidine and 2'fluoro uridine), hydroxyl pyrimidines (such as 5'-$\alpha$-P-borano uridine), 2'-O-methyl nucleotides (such as 2'-O-methyl adenosine, 2'-O-methyl guanosine, 2'-O-methyl cytidine and 2'-O-methyl uridine), 4'-thio pyrimidines (such as 4'-thio uridine and 4'-thio cytidine) and nucleotides have modifications of the nucleobase (such as 5-pentynyl-2'-deoxy uridine, 5-(3-aminopropyl)-uridine and 1,6-diaminohexyl-N-5-carbamoylmethyl uridine).

Oligonucleotides are short nucleotide polymers which typically have 50 or fewer nucleotides, such 40 or fewer, 30 or fewer, 20 or fewer, 10 or fewer or 5 or fewer nucleotides. The oligonucleotides may comprise any of the nucleotides discussed above, including the abasic and modified nucleotides. The method of the invention is preferably for characterising a target polynucleotide. A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the target polynucleotide can be oxidized or methylated. One or more nucleotides in the target polynucleotide may be damaged. For instance, the polynucleotide may comprise a pyrimidine dimer. Such dimers are typically associated with damage by ultraviolet light and are the primary cause of skin melanomas. One or more nucleotides in the target polynucleotide may be modified, for instance with a label or a tag. Suitable labels are described above. The target polynucleotide may comprise one or more spacers.

Nucleotides are defined above. Nucleotides present in the polynucleotide typically include, but are not limited to, adenosine monophosphate (AMP), guanosine monophosphate (GMP), thymidine monophosphate (TMP), uridine monophosphate (UMP), cytidine monophosphate (CMP), cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP) and deoxycytidine monophosphate (dCMP). The nucleotides are preferably selected from AMP, TMP, GMP, CMP, UMP, dAMP, dTMP, dGMP, dCMP and dUMP.

A nucleotide may be abasic (i.e. lack a nucleobase).

The nucleotides in the polynucleotide may be attached to each other in any manner. The nucleotides are typically attached by their sugar and phosphate groups as in nucleic acids. The nucleotides may be connected via their nucleobases as in pyrimidine dimers.

The polynucleotide may be single stranded or double stranded. At least a portion of the polynucleotide is preferably double stranded. A single stranded polynucleotide may have one or more primers hybridised thereto and hence comprise one or more short regions of double stranded polynucleotide. The primers may be the same type of polynucleotide as the target polynucleotide or may be a different type of polynucleotide.

The polynucleotide can be a nucleic acid, such as deoxyribonucleic acid (DNA) or ribonucleic acid (RNA). The target polynucleotide can comprise one strand of RNA hybridized to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains.

The whole or only part of the target polynucleotide may be characterised using this method. The target polynucleotide can be any length. For example, the polynucleotide can be at least 10, at least 50, at least 100, at least 150, at least 200, at least 250, at least 300, at least 400 or at least 500 nucleotide pairs in length. The polynucleotide can be 1000 or more nucleotide pairs, 5000 or more nucleotide pairs in length or 100000 or more nucleotide pairs in length.

The target analyte, such as a target polynucleotide, is present in any suitable sample. The invention is typically carried out on a sample that is known to contain or suspected to contain the target analyte, such as the target polynucleotide. Alternatively, the invention may be carried out on a sample to confirm the identity of one or more target analytes, such as one or more target polynucleotides, whose presence in the sample is known or expected.

The sample may be a biological sample. The invention may be carried out in vitro on a sample obtained from or extracted from any organism or microorganism. The organism or microorganism is typically archaean, prokaryotic or eukaryotic and typically belongs to one the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep or pigs or may alternatively be pets such as cats or dogs. Alternatively a sample of plant origin is typically obtained from a commercial crop, such as a cereal, legume, fruit or vegetable, for example wheat, barley, oats, canola, maize, soya, rice, bananas, apples, tomatoes, potatoes, grapes, tobacco, beans, lentils, sugar cane, cocoa, cotton.

The sample may be a non-biological sample. The non-biological sample is preferably a fluid sample. Examples of a non-biological sample include surgical fluids, water such as drinking water, sea water or river water, and reagents for laboratory tests.

The sample is typically processed prior to being assayed, for example by centrifugation or by passage through a membrane that filters out unwanted molecules or cells, such as red blood cells. The sample may be measured immediately upon being taken. The sample may also be typically stored prior to assay, preferably below −70° C.

The pore is typically present in a membrane. Any membrane may be used in accordance with the invention. Suitable membranes are well-known in the art. The membrane preferably comprises sphingomyelin. The membrane is preferably an amphiphilic layer. An amphiphilic layer is a layer formed from amphiphilic molecules, such as phospholipids, which have both at least one hydrophilic portion and at least one lipophilic or hydrophobic portion. The amphiphilic molecules may be synthetic or naturally occurring. Non-naturally occurring amphiphiles and amphiphiles which form a monolayer are known in the art and include, for example, blockcopolymers (Gonzalez-Perez et al., Langmuir, 2009, 25, 10447-10450). Block copolymers are polymeric materials in which two or more monomer sub-units that are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphiphiles. The copolymer may be a triblock, tetrablock or pentablock copolymer.

The amphiphilic layer may be a monolayer or a bilayer. The amphiphilic layer is typically a planar lipid bilayer or a supported bilayer.

The amphiphilic layer is typically a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Suitable methods are disclosed in the Example. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

In a preferred embodiment, the lipid bilayer is formed as described in International Application No. PCT/GB08/004127 (published as WO 2009/077734). In another preferred embodiment, the membrane is a solid state layer. A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as $Si3N4$, $Al_2O_3$, and SiO, organic and inorganic polymers such as polyamide, plastics such as Teflon® or elastomers such as two-component addition-cure silicone rubber, and glasses. The solid state layer may be formed from monatomic layers, such as graphene, or layers that are only a few atoms thick. Suitable graphene layers are disclosed in International Application No. PCT/US2008/010637 (published as WO 2009/035647).

The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial lipid bilayer. The layer may comprise other transmembrane and/or intramembrane proteins as well as other molecules in addition to the pore. Suitable apparatus and conditions are discussed below. The method of the invention is typically carried out in vitro. The analyte, such as a target polynucleotide, may be coupled to the membrane. This may be done using any known method. If the membrane is an amphiphilic layer, such as a lipid bilayer (as discussed in detail above), the analyte, such as a target polynucleotide, is preferably coupled to the membrane via a polypeptide present in the membrane or a hydrophobic anchor present in the membrane. The hydrophobic anchor is preferably a lipid, fatty acid, sterol, carbon nanotube or amino acid.

The analyte, such as a target polynucleotide, may be coupled directly to the membrane. The analyte, such as a target polynucleotide, is preferably coupled to the membrane via a linker. Preferred linkers include, but are not limited to, polymers, such as polynucleotides, polyethylene glycols (PEGs) and polypeptides. If a polynucleotide is coupled directly to the membrane, then some data will be lost as the characterising run cannot continue to the end of the polynucleotide due to the distance between the membrane and the interior of the pore. If a linker is used, then the polynucleotide can be processed to completion. If a linker is used, the linker may be attached to the polynucleotide at any position. The linker is preferably attached to the polynucleotide at the tail polymer.

The coupling may be stable or transient. For certain applications, the transient nature of the coupling is preferred. If a stable coupling molecule were attached directly to either the 5' or 3' end of a polynucleotide, then some data will be lost as the characterising run cannot continue to the end of the polynucleotide due to the distance between the bilayer and the interior of the pore. If the coupling is transient, then when the coupled end randomly becomes free of the bilayer, then the polynucleotide can be processed to completion. Chemical groups that form stable or transient links with the membrane are discussed in more detail below. The analyte, such as a target polynucleotide, may be transiently coupled to an amphiphilic layer, such as a lipid bilayer using cholesterol or a fatty acyl chain. Any fatty acyl chain having a length of from 6 to 30 carbon atoms, such as hexadecanoic acid, may be used.

In preferred embodiments, the analyte, such as a target polynucleotide, is coupled to an amphiphilic layer. Coupling of analytes, such as a target polynucleotide, to synthetic lipid bilayers has been carried out previously with various different tethering strategies. These are summarised in Table 5 below.

TABLE 5

| Attachment group | Type of coupling | Reference |
| --- | --- | --- |
| Thiol | Stable | Yoshina-Ishii, C. and S. G. Boxer (2003). "Arrays of mobile tethered vesicles on supported lipid bilayers." *J Am Chem Soc* 125(13): 3696-7. |
| Biotin | Stable | Nikolov, V., R. Lipowsky, et al. (2007). "Behavior of giant vesicles with anchored DNA molecules." *Biophys J* 92(12): 4356-68 |
| Cholesterol | Transient | Pfeiffer, I. and F. Hook (2004). "Bivalent cholesterol-based coupling of oligonucletides to lipid membrane assemblies." *J Am Chem Soc* 126(33): 10224-5 |
| Lipid | Stable | van Lengerich, B., R. J. Rawle, et al. "Covalent attachment of lipid vesicles to a fluid-supported bilayer allows observation of DNA-mediated vesicle interactions." *Langmuir* 26(11): 8666-72 |

Polynucleotides may be functionalized using a modified phosphoramidite in the synthesis reaction, which is easily compatible for the addition of reactive groups, such as thiol, cholesterol, lipid and biotin groups. These different attachment chemistries give a suite of attachment options for polynucleotides. Each different modification group tethers the polynucleotide in a slightly different way and coupling is not always permanent so giving different dwell times for the polynucleotide to the bilayer. The advantages of transient coupling are discussed above.

Coupling of polynucleotides can also be achieved by a number of other means provided that a reactive group can be added to the polynucleotide. The addition of reactive groups to either end of DNA has been reported previously. A thiol group can be added to the 5' of ssDNA using polynucleotide kinase and ATPγS (Grant, G. P. and P. Z. Qin (2007). "A facile method for attaching nitroxide spin labels at the 5' terminus of nucleic acids." *Nucleic Acids Res* 35(10): e77). A more diverse selection of chemical groups, such as biotin, thiols and fluorophores, can be added using terminal transferase to incorporate modified oligonucleotides to the 3' of ssDNA (Kumar, A., P. Tchen, et al. (1988). "Nonradioactive labelling of synthetic oligonucleotide probes with terminal deoxynucleotidyl transferase." *Anal Biochem* 169(2): 376-82).

Alternatively, the reactive group could be considered to be the addition of a short piece of DNA complementary to one already coupled to the bilayer, so that attachment can be achieved via hybridisation. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." *Proc Natl Acad Sci USA* 89(20): 9823-5). Alternatively either ssDNA or dsDNA could be ligated to native dsDNA and then the two strands separated by thermal or chemical denaturation. To native dsDNA, it is possible to add either a piece of ssDNA to one or both of the ends of the duplex, or dsDNA to one or both ends. Then, when the duplex is melted, each single strand will have either a 5' or 3' modification if ssDNA was used for ligation or a modification at the 5' end, the 3' end or both if dsDNA was used for ligation. If the polynucleotide is a synthetic strand, the coupling chemistry can be incorporated during the chemical synthesis of the polynucleotide. For instance, the polynucleotide can be synthesized using a primer a reactive group attached to it.

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. By using an antisense primer that has a reactive group, such as a cholesterol, thiol, biotin or lipid, each copy of the target DNA amplified will contain a reactive group for coupling.

The pore used in the method of the invention is a pore of the invention (i.e. a pore comprising at least one mutant monomer of the invention or at least one construct of the invention). The pore may be chemically modified in any of the ways discussed above. The pore is preferably modified with a covalent adaptor that is capable of interacting with the target analyte as discussed above.

The method is preferably for characterising a target polynucleotide and step (a) comprises contacting the target polynucleotide with the pore and a polynucleotide binding protein and the polynucleotide binding protein controls the movement of the target polynucleotide through the pore. The polynucleotide binding protein may be any protein that is capable of binding to the polynucleotide and controlling its movement through the pore. It is straightforward in the art to determine whether or not a polynucleotide binding protein binds to a polynucleotide. The polynucleotide binding protein typically interacts with and modifies at least one property of the polynucleotide. The polynucleotide binding protein may modify the polynucleotide by cleaving it to form individual nucleotides or shorter chains of nucleotides, such as di- or trinucleotides. The moiety may modify the polynucleotide by orienting it or moving it to a specific position, i.e. controlling its movement.

The polynucleotide binding protein is preferably a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide binding protein typically comprises a polynucleotide binding domain and a catalytic domain. The polynucleotide handling enzyme does not need to display enzymatic activity as long as it is capable of binding the target sequence and controlling its movement through the pore. For instance, the enzyme may be modified to remove its enzymatic activity or may be used under conditions which prevent it from acting as an enzyme. Such conditions are discussed in more detail below.

The polynucleotide handling enzyme is preferably derived from a nucleolytic enzyme. The polynucleotide handling enzyme used in the construct of the enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in International Application No. PCT/GB10/000133 (published as WO 2010/086603).

Preferred enzymes are polymerases, exonucleases, helicases and topoisomerases, such as gyrases. Suitable enzymes include, but are not limited to, exonuclease I from *E. coli* (SEQ ID NO: 6), exonuclease III enzyme from *E. coli* (SEQ ID NO: 8), RecJ from *T. thermophilus* (SEQ ID NO: 10) and bacteriophage lambda exonuclease (SEQ ID NO: 12) and variants thereof. Three subunits comprising the sequence shown in SEQ ID NO: 10 or a variant thereof interact to form a trimer exonuclease. The enzyme may be Phi29 DNA polymerase (SEQ ID NO: 4) or a variant thereof. The enzyme may be a helicase or derived from a helicase. Typical helicases are He1308, RecD or XPD, for example He1308 Mbu (SEQ ID NO: 13) or a variant thereof.

The enzyme is most preferably derived from a helicase, such as a He1308 helicase, a RecD helicase, such as TraI helicase or a TrwC helicase, a XPD helicase or a Dda helicase. The helicase may be any of the helicases, modified helicases or helicase constructs disclosed in International Application Nos. PCT/GB2012/052579 (published as WO 2013/057495); PCT/GB2012/053274 (published as WO 2013/098562); PCT/GB2012/053273 (published as WO2013098561); PCT/GB2013/051925 (published as WO 2014/013260); PCT/GB2013/051924 (published as WO 2014/013259); PCT/GB2013/051928 (published as WO 2014/013262) and PCT/GB2014/052736.

The helicase preferably comprises the sequence shown in SEQ ID NO: 18 (Dda) or a variant thereof. Variants may differ from the native sequences in any of the ways discussed below for transmembrane pores. A preferred variant of SEQ ID NO: 18 comprises (a) E94C and A360C or (b) E94C, A360C, C109A and C136A and then optionally (ΔM1)G1G2 (i.e. deletion of M1 and then addition G1 and G2).

A variant of SEQ ID NOs: 4, 6, 8, 10, 12, 13 or 18 is an enzyme that has an amino acid sequence which varies from that of SEQ ID NO: 4, 6, 8, 10, 12, 13 or 18 and which retains polynucleotide binding ability. The variant may include modifications that facilitate binding of the polynucleotide and/or facilitate its activity at high salt concentrations and/or room temperature.

Over the entire length of the amino acid sequence of SEQ ID NO: 4, 6, 8, 10, 12, 13 or 18, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 4, 6, 8, 10, 12, 13 or 18 over the entire sequence. There may be at least 80%, for example at least 85%, 90% or 95%, amino acid identity over a stretch of 200 or more, for example 230, 250, 270 or 280 or more, contiguous amino acids ("hard homology"). Homology is determined as described above. The variant may differ from the wild-type sequence in any of the ways discussed above with reference to SEQ ID NO: 2. The enzyme may be covalently attached to the pore as discussed above.

There are two main strategies for sequencing polynucleotides using nanopores, namely strand sequencing and exonuclease sequencing. The method of the invention may concern either strand sequencing or exonuclease sequencing.

In strand sequencing, the DNA is translocated through the nanopore either with or against an applied potential. Exonucleases that act progressively or processively on double stranded DNA can be used on the cis side of the pore to feed the remaining single strand through under an applied potential or the trans side under a reverse potential. Likewise, a helicase that unwinds the double stranded DNA can also be used in a similar manner. A polymerase may also be used. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential.

In one embodiment, the method of characterising a target polynucleotide involves contacting the target sequence with a pore and a helicase enzyme. Any helicase may be used in the method. Helicases may work in two modes with respect to the pore. First, the method is preferably carried out using a helicase such that it controls movement of the target sequence through the pore with the field resulting from the applied voltage. In this mode the 5' end of the DNA is first captured in the pore, and the enzyme controls movement of the DNA into the pore such that the target sequence is passed through the pore with the field until it finally translocates through to the trans side of the bilayer. Alternatively, the method is preferably carried out such that a helicase enzyme controls movement of the target sequence through the pore against the field resulting from the applied voltage. In this mode the 3' end of the DNA is first captured in the pore, and the enzyme controls movement of the DNA through the pore such that the target sequence is pulled out of the pore against the applied field until finally ejected back to the cis side of the bilayer.

In exonuclease sequencing, an exonuclease releases individual nucleotides from one end of the target polynucleotide and these individual nucleotides are identified as discussed below. In another embodiment, the method of characterising a target polynucleotide involves contacting the target sequence with a pore and an exonuclease enzyme. Any of the exonuclease enzymes discussed above may be used in the method. The enzyme may be covalently attached to the pore as discussed above.

Exonucleases are enzymes that typically latch onto one end of a polynucleotide and digest the sequence one nucleotide at a time from that end. The exonuclease can digest the polynucleotide in the 5' to 3' direction or 3' to 5' direction. The end of the polynucleotide to which the exonuclease binds is typically determined through the choice of enzyme used and/or using methods known in the art. Hydroxyl groups or cap structures at either end of the polynucleotide may typically be used to prevent or facilitate the binding of the exonuclease to a particular end of the polynucleotide.

The method involves contacting the polynucleotide with the exonuclease so that the nucleotides are digested from the end of the polynucleotide at a rate that allows characterisation or identification of a proportion of nucleotides as discussed above. Methods for doing this are well known in the art. For example, Edman degradation is used to successively digest single amino acids from the end of polypeptide such that they may be identified using High Performance Liquid Chromatography (HPLC). A homologous method may be used in the present invention.

The rate at which the exonuclease functions is typically slower than the optimal rate of a wild-type exonuclease. A suitable rate of activity of the exonuclease in the method of the invention involves digestion of from 0.5 to 1000 nucleotides per second, from 0.6 to 500 nucleotides per second, 0.7 to 200 nucleotides per second, from 0.8 to 100 nucleotides per second, from 0.9 to 50 nucleotides per second or 1 to 20 or 10 nucleotides per second. The rate is preferably 1, 10, 100, 500 or 1000 nucleotides per second. A suitable rate of exonuclease activity can be achieved in various ways. For example, variant exonucleases with a reduced optimal rate of activity may be used in accordance with the invention.

The method of the invention involves measuring one or more characteristics of the target analyte, such as a target polynucleotide. The method may involve measuring two, three, four or five or more characteristics of the target analyte, such as a target polynucleotide. For target polynucleotides, the one or more characteristics are preferably selected from (i) the length of the target polynucleotide, (ii) the identity of the target polynucleotide, (iii) the sequence of the target polynucleotide, (iv) the secondary structure of the target polynucleotide and (v) whether or not the target polynucleotide is modified. Any combination of (i) to (v) may be measured in accordance with the invention.

For (i), the length of the polynucleotide may be measured using the number of interactions between the target polynucleotide and the pore.

For (ii), the identity of the polynucleotide may be measured in a number of ways. The identity of the polynucleotide may be measured in conjunction with measurement of the sequence of the target polynucleotide or without measurement of the sequence of the target polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the target polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the target polynucleotide is modified by methylation, by oxidation, by damage, with one or more proteins or with one or more labels, tags or spacers. Specific modifications will result in specific interactions with the pore which can be measured using the methods described below. For instance, methylcytosine may be distinguished from cytosine on the basis of the current flowing through the pore during its interaction with each nucleotide.

The invention also provides a method of estimating the sequence of a target polynucleotide. The invention further provides a method of sequencing a target polynucleotide.

A variety of different types of measurements may be made. This includes without limitation: electrical measurements and optical measurements. Possible electrical measurements include: current measurements, impedance measurements, tunnelling measurements (Ivanov A P et al., Nano Lett. 2011 Jan. 12; 11(1):279-85), and FET measurements (International Application WO 2005/124888). A suitable optical method involving the measurement of fluorescence is disclosed by J. Am. Chem. Soc. 2009, 131 1652-1653. Optical measurements may be combined with electrical measurements (Soni G V et al., Rev Sci Instrum. 2010 January; 81(1):014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO-2000/28312. Alternatively, electrical measurements may be made using a multi-channel system, for example as described in International Application WO-2009/077734 and International Application WO-2011/067559.

In a preferred embodiment, the method comprises:
(a) contacting the target polynucleotide with a pore of the invention and a polynucleotide binding protein such that the target polynucleotide moves through the pore and the binding protein controls the movement of the target polynucleotide through the pore; and
(b) measuring the current passing through the pore as the polynucleotide moves with respect to the pore wherein the current is indicative of one or more characteristics of the target polynucleotide and thereby characterising the target polynucleotide.

The methods may be carried out using any apparatus that is suitable for investigating a membrane/pore system in which a pore is inserted into a membrane. The method may be carried out using any apparatus that is suitable for transmembrane pore sensing. For example, the apparatus comprises a chamber comprising an aqueous solution and a barrier that separates the chamber into two sections. The barrier has an aperture in which the membrane containing the pore is formed.

The methods may be carried out using the apparatus described in International Application No. PCT/GB08/000562 (WO 2008/102120).

The methods may involve measuring the current passing through the pore as the analyte, such as a target polynucleotide, moves with respect to the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods of the invention may involve the measuring of a current passing through the pore as the analyte, such as a target polynucleotide, moves with respect to the pore. Suitable conditions for measuring ionic currents through transmembrane protein pores are known in the art and disclosed in the Example. The method is typically carried out with a voltage applied across the membrane and pore. The voltage used is typically from +2 V to −2 V, typically −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl) or caesium chloride (CsCl) is typically used. KCl is preferred. The salt concentration may be at saturation. The salt concentration may be 3M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is HEPES. Another suitable buffer is Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

The method is typically carried out in the presence of free nucleotides or free nucleotide analogues and an enzyme cofactor that facilitate the action of the polynucleotide binding protein, such as a helicase or an exonuclease. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the helicase to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $mg^{2+}$.

The target polynucleotide may be contacted with the pore and the polynucleotide binding protein in any order. It is preferred that, when the target polynucleotide is contacted with the polynucleotide binding protein and the pore, the target polynucleotide firstly forms a complex with the polynucleotide binding protein. When the voltage is applied across the pore, the target polynucleotide/protein complex then forms a complex with the pore and controls the movement of the polynucleotide through the pore.

Methods of Identifying an Individual Nucleotide

The present invention also provides a method of characterising an individual nucleotide. In other words, the target analyte is an individual nucleotide. The method comprises contacting the nucleotide with a pore of the invention such that the nucleotide interacts with the pore and measuring the current passing through the pore during the interaction and thereby characterising the nucleotide. The invention therefore involves nanopore sensing of an individual nucleotide. The invention also provides a method of identifying an individual nucleotide comprising measuring the current passing through the pore during the interaction and thereby determining the identity of the nucleotide. Any of the pores of the invention discussed above may be used. The pore is preferably chemically modified with a molecular adaptor as discussed above.

The nucleotide is present if the current flows through the pore in a manner specific for the nucleotide (i.e. if a distinctive current associated with the nucleotide is detected flowing through the pore). The nucleotide is absent if the current does not flow through the pore in a manner specific for the nucleotide.

The invention can be used to differentiate nucleotides of similar structure on the basis of the different effects they have on the current passing through a pore. Individual nucleotides can be identified at the single molecule level from their current amplitude when they interact with the pore. The invention can also be used to determine whether or not a particular nucleotide is present in a sample. The invention can also be used to measure the concentration of a particular nucleotide in a sample.

The pore is typically present in a membrane. The methods may be carried out using any suitable membrane/pore system described above.

An individual nucleotide is a single nucleotide. An individual nucleotide is one which is not bound to another nucleotide or polynucleotide by a nucleotide bond. A nucleotide bond involves one of the phosphate groups of a nucleotide being bound to the sugar group of another nucleotide. An individual nucleotide is typically one which is not bound by a nucleotide bond to another polynucleotide of at least 5, at least 10, at least 20, at least 50, at least 100, at least 200, at least 500, at least 1000 or at least 5000 nucleotides. For example, the individual nucleotide has been digested from a target polynucleotide sequence, such as a DNA or RNA strand. The methods of the invention may be used to identify any nucleotide. The nucleotide can be any of those discussed above.

The nucleotide may be derived from the digestion of a nucleic acid sequence such as ribonucleic acid (RNA) or deoxyribonucleic acid (DNA). Nucleic acid sequences can be digested using any method known in the art. Suitable methods include, but are not limited to, those using enzymes or catalysts. Catalytic digestion of nucleic acids is disclosed in Deck et al., Inorg. Chem., 2002; 41: 669-677.

Individual nucleotides from a single polynucleotide may be contacted with the pore in a sequential manner in order to sequence the whole or part of the polynucleotide. Sequencing polynucleotides is discussed in more detail above.

The nucleotide may be contacted with the pore on either side of the membrane. The nucleotide may be introduced to the pore on either side of the membrane. The nucleotide may be contacted with the side of the membrane that allows the nucleotide to pass through the pore to the other side of the membrane. For example, the nucleotide is contacted with an end of the pore, which in its native environment allows the entry of ions or small molecules, such as nucleotides, into the barrel or channel of the pore such that the nucleotide may pass through the pore. In such cases, the nucleotide interacts with the pore and/or adaptor as it passes across the membrane through the barrel or channel of the pore. Alternatively, the nucleotide may be contacted with the side of the membrane that allows the nucleotide to interact with the pore via or in conjunction with the adaptor, dissociate from the pore and remain on the same side of the membrane. The present invention provides pores in which the position of the adaptor is fixed. As a result, the nucleotide is preferably contacted with the end of the pore which allows the adaptor to interact with the nucleotide.

The nucleotide may interact with the pore in any manner and at any site. As discussed above, the nucleotide preferably reversibly binds to the pore via or in conjunction with the adaptor. The nucleotide most preferably reversibly binds to the pore via or in conjunction with the adaptor as it passes through the pore across the membrane. The nucleotide can also reversibly bind to the barrel or channel of the pore via or in conjunction with the adaptor as it passes through the pore across the membrane.

During the interaction between the nucleotide and the pore, the nucleotide affects the current flowing through the pore in a manner specific for that nucleotide. For example, a particular nucleotide will reduce the current flowing through the pore for a particular mean time period and to a particular extent. In other words, the current flowing through the pore is distinctive for a particular nucleotide. Control experiments may be carried out to determine the effect a particular nucleotide has on the current flowing through the pore. Results from carrying out the method of the invention on a test sample can then be compared with those derived from such a control experiment in order to identify a particular nucleotide in the sample or determine whether a particular nucleotide is present in the sample. The frequency at which the current flowing through the pore is affected in a manner indicative of a particular nucleotide can be used to determine the concentration of that nucleotide in the sample. The ratio of different nucleotides within a sample can also be calculated. For instance, the ratio of dCMP to methyl-dCMP can be calculated.

The method may involve the use of any apparatus, sample or condition discussed above.

Methods of Forming Sensors

The invention also provides a method of forming a sensor for characterising a target polynucleotide. The method comprises forming a complex between a pore of the invention and a polynucleotide binding protein, such as a helicase or an exonuclease. The complex may be formed by contacting the pore and the protein in the presence of the target polynucleotide and then applying a potential across the pore. The applied potential may be a chemical potential or a voltage potential as described above. Alternatively, the complex may be formed by covalently attaching the pore to the protein. Methods for covalent attachment are known in the art and disclosed, for example, in International Application Nos. PCT/GB09/001679 (published as WO 2010/004265) and PCT/GB10/000133 (published as WO 2010/086603). The complex is a sensor for characterising the target polynucleotide. The method preferably comprises forming a complex between a pore of the invention and a helicase. Any of the embodiments discussed above equally apply to this method.

The invention also provides a sensor for characterising a target polynucleotide. The sensor comprises a complex between a pore of the invention and a polynucleotide binding protein. Any of the embodiments discussed above equally apply to the sensor of the invention.

Kits

The present invention also provides a kit for characterising, such as sequencing, a target polynucleotide. The kit comprises (a) a pore of the invention and (b) a membrane. The kit preferably further comprises a polynucleotide binding protein, such as a helicase or an exonuclease. Any of the embodiments discussed above equally applicable to the kits of the invention.

The kits of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotide sequences, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise nucleotides.

Apparatus

The invention also provides an apparatus for characterising, such as sequencing, target polynucleotides in a sample. The apparatus may comprise (a) a plurality of pores of the invention and (b) a plurality of polynucleotide binding proteins, such as helicases or exonucleases. The apparatus may be any conventional apparatus for analyte analysis, such as an array or a chip.

The array or chip typically contains multiple wells of membrane, such as a block co-polymer membrane, each with a single nanopore inserted. The array may be integrated within an electronic chip.

The apparatus preferably comprises:
    a sensor device that is capable of supporting the plurality of pores and being operable to perform polynucleotide characterising or sequencing using the pores and proteins;
    at least one reservoir for holding material for performing the characterising or sequencing;
    a fluidics system configured to controllably supply material from the at least one reservoir to the sensor device; and
    a plurality of containers for receiving respective samples, the fluidics system being configured to supply the samples selectively from the containers to the sensor device.

The apparatus may be any of those described in International Application No. PCT/GB10/000789 (published as WO 2010/122293), International Application No. PCT/GB10/002206 (published as WO 2011/067559) or International Application No. PCT/US99/25679 (published as WO 00/28312).

The following Examples illustrate the invention.

Example 1

This example describes how a helicase—T4 Dda—E94C/C109A/C136A/A360C (SEQ ID NO: 18 with mutations E94C/C109A/C136A/A360C) was used to control the movement of DNA through a number of different mutant lysenin nanopores. All of the nanopores tested exhibited changes in current as the DNA translocated through the nanopore. The mutant nanopores tested exhibited either 1) increased range, 2) reduced noise, 3) improved signal:noise, 4) increased capture when compared to a mutant control nanopore or 5) altered size of the read-head when compared to a baseline.

Figure 5:
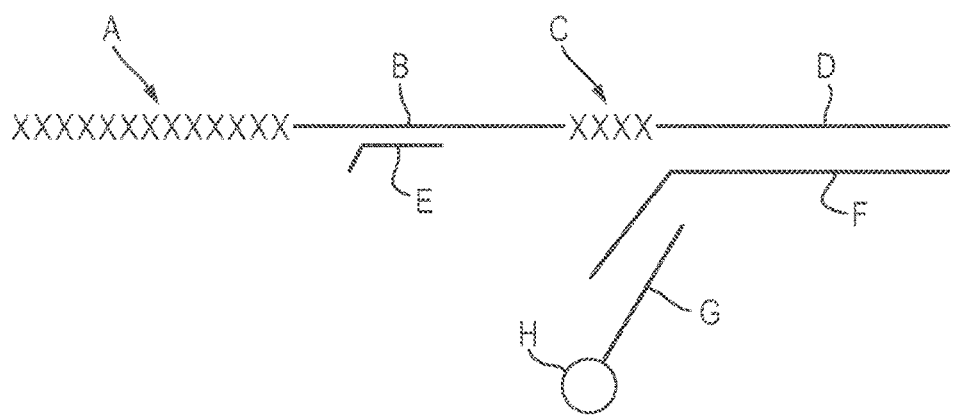
FIG. 5 shows the adapter used in the examples. A corresponds to 30 iSpC3. B corresponds to SEQ ID NO: 19. C corresponds to 4 iSp18. D corresponds to SEQ ID NO: 20. E corresponds to SEQ ID NO: 21 which has 5BNA-G//iBNA-G//iBNA-T//iBNA-T//i-BNA-A attached to its 5' end. F corresponds to SEQ ID NO: 22 which has a 5' phosphate. G corresponds to SEQ ID NO: 24. H corresponds to a cholesterol.
Figure 6:
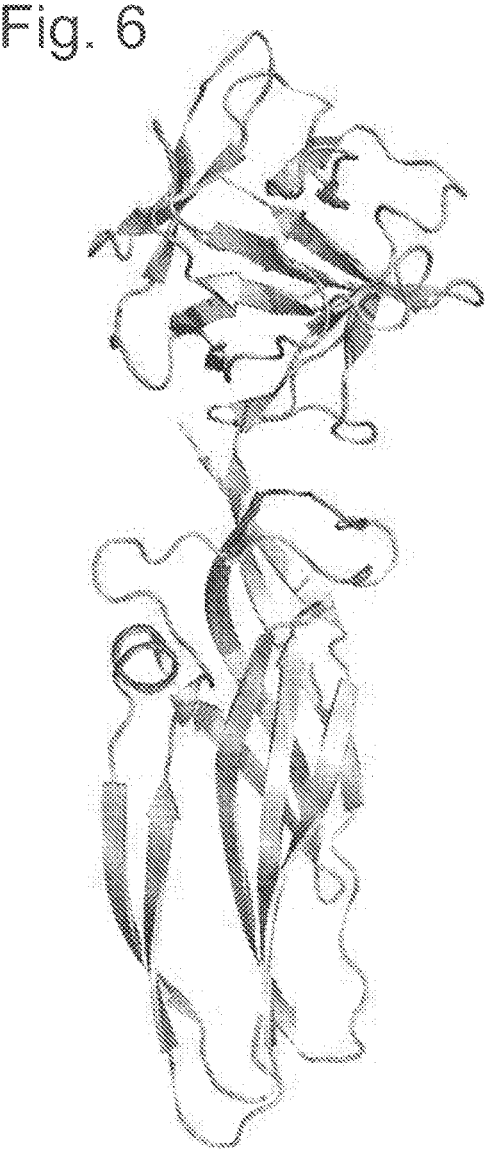
FIG. 6 shows the 3D structure of a monomer of lysenin. Upon interaction with sphingomyelin containing membranes, lysenin monomers assemble together to form a nonameric pore via an intermediate pre-pore. During the assembly process, the polypeptide section shown in black (corresponding to amino acids 65-74 of SEQ ID NO: 2) converts into the bottom loop of the beta barrel shown in FIG. 7. The two beta sheets on either side of the polypeptide section shown in black and the polypeptide sections linking those beta sheets to the polypeptide section shown in black (corresponding to amino acids 34-64 and 75-107 of SEQ ID NO: 2) extend to form the beta barrel of the pore as shown in FIG. 7. Such large structural changes make it difficult to predict the beta barrel region of the lysenin pore by studying the monomeric structure.

Materials and Methods
DNA Construct Preparation
    70 uL of T4 Dda—E94C/C109A/C136A/A360C was buffer exchanged (using a Zeba column) into 70 uL 1× KOAc buffer, with 2 mM EDTA.
    70 uL of the T4 Dda—E94C/C109A/C136A/A360C buffer exchange mix was added to 70 uL of 2 uM DNA adapter (See FIG. 5 for details of sequences). The sample was then mixed and incubated for 5 mins at room temperature.
    1 uL of 140 mM TMAD was added and the sample mixed and incubated for 60 min at room temperature. This sample was known as sample A. A 2 ul aliquot was then removed for Agilent analysis.
HS/ATP Step
    The reagents in the table below were mixed and incubated at room temperature for 25 minutes. This sample was known as sample B.

| Reagent | Volume | Final |
|---|---|---|
| Sample A (500 nM) | 139 | 220 nM |
| 2× HS buffer (100 mM Hepes, 2M KCl, pH8) | 150 | 1× |

-continued

| Reagent | Volume | Final |
|---|---|---|
| 600 mM MgCl2 | 7 | 14 mM |
| 100 mM rATP | 4.2 | 14 mM |
| Final | 300.2 | |

SPRI Purification 1.1 mL of SPRI beads was added to sample B and then the sample was mixed and incubated for 5 mins.

The beads were pelleted and the supernatant removed. The beads were then washed with 50 mM Tris·HCl, 2.5 M NaCl, 20% PEG8000.

Sample C was eluted in 70 uL of 10 mM Tris·HCl, 20 mM NaCl.

Ligation of 10 kb Lambda C to Adapter with Enzyme

The reagents in the table below were incubated at 20° C. for 10 mins in a thermocycler.

| | Volume μl | |
|---|---|---|
| nH2O | 310.2 | |
| 10 kb Lambda C DNA (SEQ ID NO: 23, 168.7 nM) | 14.82 | 5 nM |
| Sample C (500 nM) | 25 | 25 nM |
| Ligation buffer (5×) | 100 | 1× |
| NEBNext Quick T4 DNA Ligase (2000 U · ul$^{-1}$) | 50 | 5% |
| Total | 500 | |

The reaction mixture (1×500 ul aliquot) was then SPRI purified with 200 ul of 20% SPRI beads, washed in 750 ul of wash buffer 1 and eluted in 125 ul of elution buffer 1. A final DNA sequence (SEQ ID NO: 24) was hybridised to the DNA. This sample was known as the sample D.

Components of Ligation Buffer (5×)

| Reagent | Volume | Final |
|---|---|---|
| 1M Tris · HCl pH8 | 15 | 150 mM |
| 1M MgCl2 | 5 | 50 mM |
| 100 mM ATP | 5 | 5 mM |
| 40% PEG 8000 | 75 | 30% |
| Total | 100 μL | |

Components of Wash Buffer 1

| Reagent | Volume | Final |
|---|---|---|
| Water | 1100 | |
| 1M Tris · HCl pH8 | 100 | 50 mM |
| 5M NaCl | 300 | 750 mM |
| 40% PEG 8000 | 500 | 10% |
| Total | 2000 μL | |

Components of Elution Buffer 1

| Reagent | Volume | Final |
|---|---|---|
| Water | 906.7 | up to 1000 μL |
| 0.5M CAPS pH10 | 80 | 40 mM |
| 3M KCl | 13.3 | 40 mM |
| Total | 1000 μL | |

Electrophysiology Experiments

Electrical measurements were acquired from single lysenin nanopores inserted in block co-polymer in buffer (25 mM K Phosphate buffer, 150 mM Potassium Ferrocyanide (II), 150 mM Potassium Ferricyanide (III), pH 8.0). After achieving a single pore inserted in the block co-polymer, then buffer (2 mL, 25 mM K Phosphate buffer, 150 mM Potassium Ferrocyanide (II), 150 mM Potassium Ferricyanide (III), pH 8.0) was flowed through the system to remove any excess lysenin nanopores. 150 uL of 500 mM KCl, 25 mM K Phosphate, pH8.0 was then flowed through the system. After 10 minutes a further 150 uL of 500 mM KCl, 25 mM K Phosphate, pH8.0 was flowed through the system and then the T4 Dda—E94C/C109A/C136A/A360C, DNA, fuel (MgCl2, ATP) pre-mix (150 μL total, Sample D) was then flowed into the single nanopore experimental system. The experiment was run at 180 mV and helicase-controlled DNA movement monitored.

Results

A number of different nanopores were investigated in order to determine the effect of mutations to regions of the transmembrane pore. The mutant pores which were investigated are listed below with the baseline nanopore with which they were compared (Baseline pores 1-4). A number of different parameters were investigated in order to identify improved nanopores 1) the average noise of the signal (where noise is equal to the standard deviation of all events in a strand, calculated over all strands) which in an improved nanopore would be lower than the baseline, 2) the average current range which was a measure of the spread of current levels within a signal and which in an improved nanopore would be higher than the baseline, 3) the average signal to noise quoted in the table is the signal to noise (average current range divided by average noise of the signal) over all strands and in an improved nanopore would be higher than the baseline, 4) the capture rate of DNA which in an improved nanopore would be higher than the baseline and 5) the read head size which in an improved nanopore could be increased or decreased depending on the size of the readhead of the baseline.

Each table below includes the relevant data for the corresponding baseline nanopore Table 6=mutant 1, table 7=mutant 2, table 8=mutant 3 and table 9=mutant 10 which was then compared to the mutated pores.

Lysenin mutant 1=Lysenin—(E84Q/E85K/E92Q/E97S/D126G)9 (SEQ ID NO: 2 with mutations E84Q/E85K/E92Q/E97S/D126G). (Baseline 1)

Lysenin mutant 2=Lysenin—(E84Q/E85K/E92Q/E94D/E97S/D126G)9 (SEQ ID NO: 2 with mutations E84Q/E85K/E92Q/E94D/E97S/D126G). (Baseline 2)

Lysenin mutant 3=Lysenin—(E84Q/E85K/E92Q/E94Q/E97S/D126G)9 (SEQ ID NO: 2 with mutations E84Q/E85K/E92Q/E94Q/E97S/D126G). (Baseline 3)

Lysenin mutant 4=Lysenin—(E84Q/E85K/S89Q/E92Q/E97S/D126G)9 (SEQ ID NO: 2 with mutations E84Q/E85K/S89Q/E92Q/E97S/D126G).

Lysenin mutant 5=Lysenin—(E84Q/E85K/T91S/E92Q/E97S/D126G)9 (SEQ ID NO: 2 with mutations E84Q/E85K/T91S/E92Q/E97S/D126G).

Lysenin mutant 6=Lysenin—(E84Q/E85K/E92Q/E97S/S98Q/D126G)9 (SEQ ID NO: 2 with mutations E84Q/E85K/E92Q/E97S/S98Q/D126G).

Lysenin mutant 7=Lysenin—(E84Q/E85K/E92Q/E97S/V100S/D126G)9 (SEQ ID NO: 2 with mutations E84Q/E85K/E92Q/E97S/V100S/D126G).

Lysenin mutant 8=Lysenin—(E84Q/E85K/E92Q/E94D/E97S/S80K/D126G)9 (SEQ ID NO: 2 with mutations E84Q/E85K/E92Q/E94D/E97S/S80K/D126G).

Lysenin mutant 9=Lysenin—(E84Q/E85K/E92Q/E94D/E97S/T106R/D126G)9 (SEQ ID NO: 2 with mutations E84Q/E85K/E92Q/E94D/E97S/T106R/D126G).

Lysenin mutant 10=Lysenin—(E84Q/E85K/E92Q/E94D/E97S/T106K/D126G)9 (SEQ ID NO: 2 with mutations E84Q/E85K/E92Q/E94D/E97S/T106K/D126G). (Baseline 4)

Lysenin mutant 11=Lysenin—(E84Q/E85K/E92Q/E94D/E97S/T104R/D126G)9 (SEQ ID NO: 2 with mutations E84Q/E85K/E92Q/E94D/E97S/T104R/D126G).

Lysenin mutant 12=Lysenin—(E84Q/E85K/E92Q/E94D/E97S/T104K/D126G)9 (SEQ ID NO: 2 with mutations E84Q/E85K/E92Q/E94D/E97S/T104K/D126G).

Lysenin mutant 13=Lysenin—(S78N/E84Q/E85K/E92Q/E94D/E97S/D126G)9 (SEQ ID NO: 2 with mutations S78N/E84Q/E85K/E92Q/E94D/E97S/D126G).

Lysenin mutant 14=Lysenin—(S82N/E84Q/E85K/E92Q/E94D/E97S/D126G)9 (SEQ ID NO: 2 with mutations S82N/E84Q/E85K/E92Q/E94D/E97S/D126G).

Lysenin mutant 15=Lysenin—(E76N/E84Q/E85K/E92Q/E94Q/E97S/D126G)9 (SEQ ID NO: 2 with mutations E76N/E84Q/E85K/E92Q/E94Q/E97S/D126G).

Lysenin mutant 16=Lysenin—(E76S/E84Q/E85K/E92Q/E94Q/E97S/D126G)9 (SEQ ID NO: 2 with mutations E76S/E84Q/E85K/E92Q/E94Q/E97S/D126G).

Lysenin mutant 17=Lysenin—(E84Q/E85K/E92Q/E94Q/Y96D/D97S/T106K/D126G)9 (SEQ ID NO: 2 with mutations E84Q/E85K/E92Q/E94Q/Y96D/D97S/T106K/D126G).

Lysenin mutant 18=Lysenin—(K45D/E84Q/E85K/E92Q/E94K/D97S/T106K/D126G)9 (SEQ ID NO: 2 with mutations K45D/E84Q/E85K/E92Q/E94K/D97S/T106K/D126G).

Lysenin mutant 19=Lysenin—(K45R/E84Q/E85K/E92Q/E94D/D97S/T106K/D126G)9 (SEQ ID NO: 2 with mutations K45R/E84Q/E85K/E92Q/E94D/D97S/T106K/D126G).

Lysenin mutant 20=Lysenin—(D35N/E84Q/E85K/E92Q/E94D/D97S/T106K/D126G)9 (SEQ ID NO: 2 with mutations D35N/E84Q/E85K/E92Q/E94D/D97S/T106K/D126G).

Lysenin mutant 21=Lysenin—(K37N/E84Q/E85K/E92Q/E94D/D97S/T106K/D126G)9 (SEQ ID NO: 2 with mutations K37N/E84Q/E85K/E92Q/E94D/D97S/T106K/D126G).

Lysenin mutant 22=Lysenin—(K37S/E84Q/E85K/E92Q/E94D/D97S/T106K/D126G)9 (SEQ ID NO: 2 with mutations K37S/E84Q/E85K/E92Q/E94D/D97S/T106K/D126G).

Lysenin mutant 23=Lysenin—(E84Q/E85K/E92D/E94Q/D97S/T106K/D126G)9 (SEQ ID NO: 2 with mutations E84Q/E85K/E92D/E94Q/D97S/T106K/D126G).

Lysenin mutant 24=Lysenin—(E84Q/E85K/E92E/E94Q/D97S/T106K/D126G)9 (SEQ ID NO: 2 with mutations E84Q/E85K/E92E/E94Q/D97S/T106K/D126G).

Lysenin mutant 25=Lysenin—(K37S/E84Q/E85K/E92Q/E94D/D97S/T104K/T106K/D126G)9 (SEQ ID NO: 2 with mutations K37S/E84Q/E85K/E92Q/E94D/D97S/T104K/T106K/D126G).

Lysenin mutant 26=Lysenin—(E84Q/E85K/M90I/E92Q/E94D/E97S/T106K/D126G)9 (SEQ ID NO: 2 with mutations E84Q/E85K/M90I/E92Q/E94D/E97S/T106K/D126G).

Lysenin mutant 27=Lysenin—(K45T/V47K/E84Q/E85K/E92Q/E94D/E97S/T106K/D126G)9 (SEQ ID NO: 2 with mutations K45T/V47K/E84Q/E85K/E92Q/E94D/E97S/T106K/D126G).

Lysenin mutant 28=Lysenin—(T51K/E84Q/E85K/E92Q/E94D/E97S/T106K/D126G)9 (SEQ ID NO: 2 with mutations T51K/E84Q/E85K/E92Q/E94D/E97S/T106K/D126G).

Lysenin mutant 29=Lysenin—(K45Y/S49K/E84Q/E85K/E92Q/E94D/E97S/T106K/D126G)9 (SEQ ID NO: 2 with mutations K45Y/S49K/E84Q/E85K/E92Q/E94D/E97S/T106K/D126G).

Lysenin mutant 30=Lysenin—(S49L/E84Q/E85K/E92Q/E94D/E97S/T106K/D126G)9 (SEQ ID NO: 2 with mutations S49L/E84Q/E85K/E92Q/E94D/E97S/T106K/D126G).

Lysenin mutant 31=Lysenin—(E84Q/E85K/V88I/M90A/E92Q/E94D/E97S/T106K/D126G)9 (SEQ ID NO: 2 with mutations E84Q/E85K/V88I/M90A/E92Q/E94D/E97S/T106K/D126G).

Lysenin mutant 32=Lysenin—(K45N/S49K/E84Q/E85K/E92D/E94N/E97S/T106K/D126G)9 (SEQ ID NO: 2 with mutations K45N/S49K/E84Q/E85K/E92D/E94N/E97S/T106K/D126G).

Lysenin mutant 33=Lysenin—(K45N/V47K/E84Q/E85K/E92D/E94N/E97S/T106K/D126G)9 (SEQ ID NO: 2 with mutations K45N/V47K/E84Q/E85K/E92D/E94N/E97S/T106K/D126G).

TABLE 6

| Mutant No. | Difference from Baseline Nanopore | Range (pA) | Noise (pA) | Signal:Noise | Advantages and Observations |
|---|---|---|---|---|---|
| 1 | Baseline 1 | 11.1 | 1.56 | 7.12 | |
| 2 | E94D | 15.7 | 2.03 | 7.73 | Increased S:N and reduction in channel gating with and without DNA in pore |
| 3 | E94Q | 23.6 | 3.55 | 6.65 | Doubled the range, reduction in channel gating with and without DNA in pore |
| 4 | S89Q | 11.96 | 1.38 | 8.67 | Lower noise |
| 5 | T91S | 12.21 | 1.31 | 9.32 | Lower noise |
| 6 | S98Q | 10.63 | 1.27 | 8.37 | Lower noise |
| 7 | V100S | 12.58 | 1.5 | 8.39 | Slight increase in range |

TABLE 7

| Mutant No. | Difference from Baseline Nanopore | Range (pA) | Noise (pA) | Signal:Noise | Advantages and Observations |
|---|---|---|---|---|---|
| 2 | Baseline 2 | 15.7 | 2.03 | 7.73 | |
| 8 | S80K | 15.29 | 2.9 | 5.27 | Improves capture rate slightly |
| 9 | T106R | 15.83 | 2.55 | 6.21 | Increases capture rate drastically |
| 10 | T106K | 15.73 | 1.99 | 7.90 | Increases capture rate drastically |
| 11 | T104R | 17.36 | 3.59 | 4.84 | Increases capture rate drastically |
| 12 | T104K | 15.55 | 2.57 | 6.05 | Increases capture rate drastically |
| 13 | S78N | 14.54 | 1.77 | 8.21 | Reduces noise |
| 14 | S82N | 15.03 | 1.81 | 8.30 | Reduces noise |

TABLE 8

| Mutant No. | Difference from Baseline Nanopore | Range (pA) | Noise (pA) | Signal:Noise | Advantages and Observations |
|---|---|---|---|---|---|
| 3 | Baseline 3 | 23.6 | 3.55 | 6.65 | |
| 15 | E76N | 16.99 | 2.3 | 7.39 | Decreases noise drastically |
| 16 | E76S | 18.35 | 2.38 | 7.71 | Decreases noise drastically |

TABLE 9

| Mutant No. | Difference from Baseline Nanopore | Range (pA) | Noise (pA) | Signal:Noise | Advantages and Observations |
|---|---|---|---|---|---|
| 10 | Baseline 4 | 13.48 | 1.35 | 9.99 | |
| 17 | E94Q/Y96D | 16.53 | 1.07 | 15.45 | Increase in range and decrease in noise, reduction in size of the read-head |
| 18 | K45D/E94K | 14.11 | 1.05 | 13.44 | Decrease in noise |
| 19 | K45R | 11.09 | 1.09 | 10.17 | Decrease in noise |
| 20 | D35N | 15.91 | 1.68 | 9.47 | Increase in range |
| 21 | K37N | 14.39 | 1.28 | 11.24 | Increase in range and decrease in noise |
| 22 | K37S | 14.47 | 1.28 | 11.30 | Increase in range and decrease in noise |
| 23 | E92D/E94Q | 20.59 | 2.05 | 10.04 | Increase in range |
| 24 | E92E/E94Q | 21.45 | 1.83 | 11.72 | Increase in range |
| 25 | K37S/T104K | 13.96 | 1.24 | 11.26 | Decrease in noise |
| 26 | M90I | 14.08 | 1.14 | 12.35 | Decrease in noise |
| 27 | K45T/V47K | 15.4 | 1.46 | 10.55 | Increase in range |
| 28 | T51K | 19.33 | 1.89 | 10.23 | Increase in range |
| 29 | K45Y/S49K | 20.69 | 1.71 | 12.10 | Increase in range |
| 30 | S49L | 12.51 | 1.1 | 11.37 | Decrease in noise |
| 31 | V88I/M90A | 13.08 | 1.17 | 11.18 | Decrease in noise |
| 32 | K45N/S49K/E92D/E94N | 15.84 | 1.44 | 11.00 | Increase in range |
| 33 | K45N/V47K/E92D/E94N | 12.31 | 1.13 | 10.89 | Decrease in noise |

Readhead Analysis

For lysenin mutants 1 and 10 we obtained a model of the expected ionic current distribution of all possible 9mer polynucleotides. The model may comprise a mean and standard deviation of the current distribution of each 9mer.

We examined and compared the structure of the model obtained for lysenin mutant 1 and 10. The figures (See FIGS. 1 and 2) provide an example of such a comparison. In the case of each model (i.e. lysenin 1 or 10) we combined the mean of the distributions for all 9mers of the form A,x_2, x_3,x_4,x_5,x_6,x_7,x_8,x_9 here x_{i} represent arbitrary polynucleotides chosen from {A,C,G,T}), the combination applied to the means being to take a median. This median averaging is repeated for all nucleotides {A,C,G,T} in position 1, and for all positions, such that we obtain 36 median values encoding the median effect of each nucleotide when it is present in any of the 9 positions of a 9mer.

Figure 2:
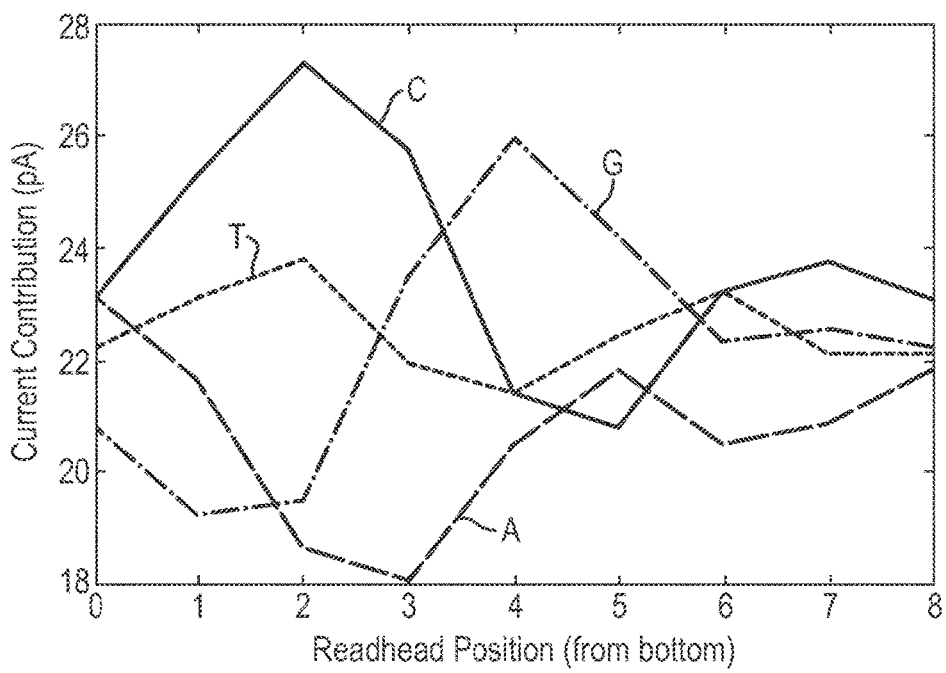
FIG. 2 shows the median plot for lysenin mutant 10.

The FIGS. 1 (lysenin mutant 1) and 2 (lysenin mutant 2) plot these medians for two different pores. The plots in FIGS. 1 and 2 show the level of discrimination between all bases at each position in the readhead. The greater the discrimination the bigger the difference between the current contribution levels at that particular position. If a position is not part of the readhead the current contribution at that position will be similar for all four bases. FIG. 2 (lysenin mutant 10) shows similar current contributions for all four bases at positions 6 to 8 of the readhead. FIG. 1 (lysenin mutant 1) does not show similar current contributions for all four bases at any position in the readhead. Therefore lysenin mutant 10 has a shorter readhead than lysenin mutant 1. A shorter read head can be advantageous as fewer bases contribute to the signal at any one time which can lead to improved base calling accuracy.

Example 2

This example describes the protocol used to produce a chemically modified assembled pore with a reduced diameter of a barrel/channel.

Monomeric Lysenin sample (about 10 umol) was first reduced to ensure maximum reactivity of the cysteine residues and therefore high efficiency coupling reaction. The monomeric lysenin sample (about 10 umol) was incubated with 1 mM dithiothreitol (DTT) for 5-15 minutes. Cellular debris and suspended aggregates were then pelleted through centrifugation, 20,000 rpm for 10 min. The soluble fraction was then recovered and buffer exchanged to 1 mM Tris, 1 mM EDTA, pH 8.0, using 7 Kd molecular weight cut off Zeba spin columns (ThermoFisher).

The molecule that was to be attached (e.g.: 2-iodo-N-(2, 2,2-trifluoroethyl)acetamide) was dissolved to a concentration of 100 mM in a suitable solvent, typically DMSO. This was added to buffer exchanged Lysenin monomer sample to a final concentration of 1 mM. The resulting solution was incubated at 30° C. for 2 hours. Modified sample (100 uL) was then oligomerised by adding 20 uL of a 5 lipid mixture from Encapsula Nanosciences (Phosphatidylserine (0.325 mg/ml): POPE (0.55 mg/ml): Cholesterol (0.45 mg/ml): Soy PC (0.9 mg/ml): Sphingomyelin (0.275 mg/ml)). The sample was incubated at 30° C. for 60 minutes. Sample was then subjected to SDS-PAGE and purified from gel as described in International application number PCT/GB2013/050667 (published as WO2013/153359).

Example 3

This example compared a chemically modified assembled lysenin pore with a reduced diameter of a barrel/channel (Lysenin—(E84Q/E85K/E92Q/E94C/E97S/T106K/D126G/C272A/C283A)9 with 2-iodo-N-(2,2,2-trifluoroethyl)acetamide attached via E94C (SEQ ID NO: 2 with mutations E84Q/E85K/E92Q/E94C/E97S/T106K/D126G/C272A/C283A) with Lysenin—(E84Q/E85K/E92Q/E94D/E97S/T106K/D126G/C272A/C283A)9 (SEQ ID NO: 2 with mutations E84Q/E85K/E92Q/E94D/E97S/T106K/D126G/C272A/C283A).

Materials and Methods

The DNA construct was prepared as described in example 1. Electrophysiology experiments were carried out as described in Example 1.

Results

The electrophysiology experiments showed that the chemically modified assembled pore (Lysenin—(E84Q/E85K/E92Q/E94C/E97S/T106K/D126G/C272A/C283A)9 with 2-iodo-N-(2,2,2-trifluoroethyl)acetamide attached via E94C (SEQ ID NO: 2 with mutations E84Q/E85K/E92Q/E94C/E97S/T106K/D126G/C272A/C283A) exhibited a median range of 21 pA which was greater than Lysenin—(E84Q/E85K/E92Q/E94D/E97S/T106K/D126G/C272A/C283A)9 which exhibited a median range of 12 pA. This increase in median range provided greater current space for the resolution of kmers.

Figure 3:
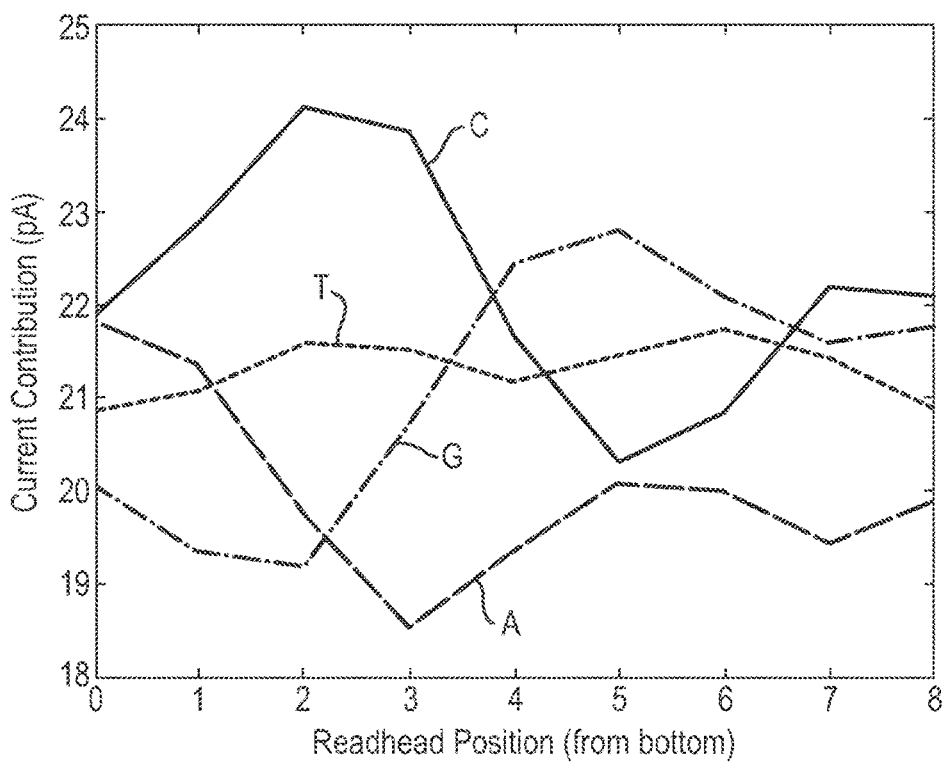
FIG. 3 shows the median plot for lysenin mutant—Lysenin—(E84Q/E85K/E92Q/E94D/E97S/T106K/D126G/C272A/C283A)9 (SEQ ID NO: 2 with mutations E84Q/E85K/E92Q/E94D/E97S/T106K/D126G/C272A/C283A).
Figure 4:
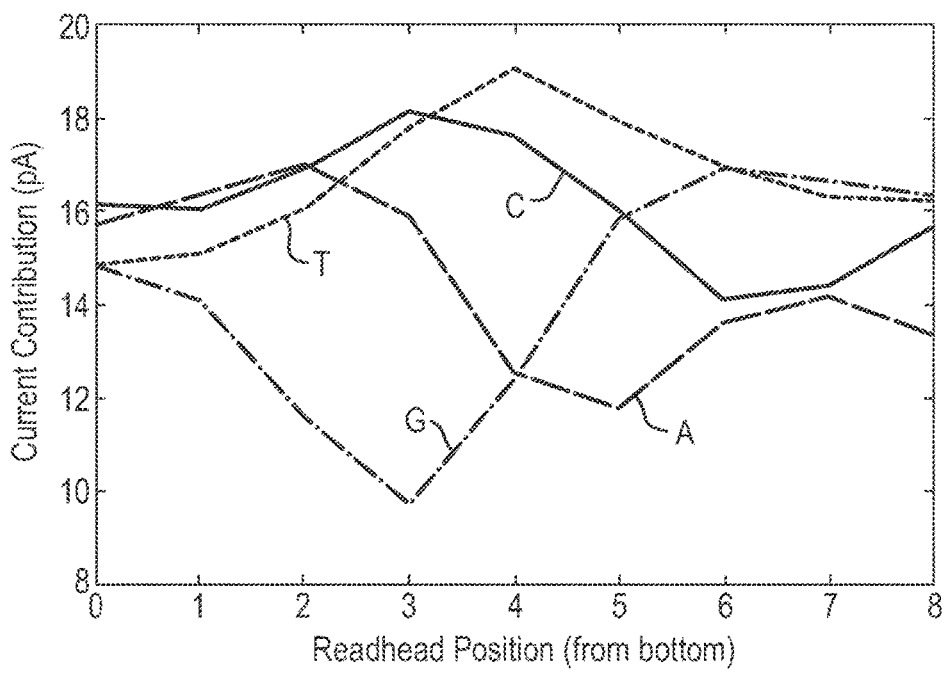
FIG. 4 shows the median plot for lysenin mutant—Lysenin—(E84Q/E85K/E92Q/E94C/E97S/T106K/D126G/C272A/C283A)9 with 2-iodo-N-(2,2,2-trifluoroethyl)acetamide attached via E94C (SEQ ID NO: 2 with mutations E84Q/E85K/E92Q/E94C/E97S/T106K/D126G/C272A/C283A).

FIGS. 3 (Lysenin—(E84Q/E85K/E92Q/E94D/E97S/T106K/D126G/C272A/C283A)9) and 4 ((Lysenin—(E84Q/E85K/E92Q/E94C/E97S/T106K/D126G/C272A/C283A)9 with 2-iodo-N-(2,2,2-trifluoroethyl)acetamide attached via E94C (SEQ ID NO: 2 with mutations E84Q/E85K/E92Q/E94C/E97S/T106K/D126G/C272A/C283A) showed plots of the medians as described in Example 1. The relative contribution to the signal of different bases at different positions had been altered when FIG. 4 was compared to FIG. 3, read-head positions at the extreme (positions 7 to 8) in FIG. 4 showed much less discrimination meaning their contribution toward the signal was much reduced and therefore the length of the Kmer being assayed at a given moment was shorter. This shorter readhead can be advantageous as fewer bases contribute to the signal at any one time which can lead to improved base calling accuracy.

Similar experiments to that described in Example 3 were carried out on Lysenin—(E84Q/E85S/E92C/E94D/E97S/T106K/D126G/C272A/C283A)9 with 2-iodo-N-(2-phenylethyl)acetamide attached via E92C (SEQ ID NO: 2 with mutations E84Q/E85S/E92C/E94D/E97S/T106K/D126G/C272A/C283A) and Lysenin—(E84Q/E85S/E92C/E94D/E97S/T106K/D126G/C272A/C283A)9 with 1-benzyl-2,5-dihydro-1H-pyrrole-2,5-dione attached via E92C (SEQ ID NO: 2 with mutations E84Q/E85S/E92C/E94D/E97S/T106K/D126G/C272A/C283A).

The invention claimed is:

1. A mutant lysenin monomer comprising a variant of the amino acid sequence set forth in SEQ ID NO: 2, wherein the variant comprises one of the following combinations of amino acid substitutions:
E94D/K99Q/T106K;
E94D/T93K/T106K;
E94D/T91K/T106K;
H83K/E94D/T106K;
E94Q/Y96D/T106K;
K45D/E94K/T106K;
K45R/E94D/T106K;
E94D/S98K/K99L/T106K;
K37N/E94D/T106K;
K37W/E94D/T106K;
K37S/E94D/T106K;
K45N/E94N/T106K;
K37Q/E94D/E102N/T106K;
K37S/E94D/E102S/T106K;
K37S/E94D/T104K/T106K;
K45Q/E94Q/T106K;
K45T/V47K/E94D/T106K;
V47S/E94D/T106K;
T51K/E94D/T106K;
K45Y/S49K/E94D/T106K;
S49L/E94D/T106K;
K45R/T106K;
V47K/E94D/T106K;
G43K/E94D/T106K;
V88I/M90A/E94D/T106K;
V47N/V88T/E94D/T106K;
K45N/S49K/E94N/E92D/T106K;
K45N/V47K/E92D/E94N/T106K; or
E94D/K99Q/T106K.

* * * * *

SEQUENCE LISTING

<160> NUMBER OF SEQ ID NOS: 24

<210> SEQ ID NO 1
<211> LENGTH: 897
<212> TYPE: DNA
<213> ORGANISM: Eisenia fetida

<400> SEQUENCE: 1

```
atgagtgcga aggctgctga aggttatgaa caaatcgaag ttgatgtggt tgctgtgtgg     60
aaggaaggtt atgtgtatga aaatcgtggt agtacctccg tggatcaaaa aattaccatc    120
acgaaaggca tgaagaacgt taatagcgaa acccgtacgg tcaccgcgac gcattctatt    180
ggcagtacca tctccacggg tgacgccttt gaaatcggct ccgtggaagt ttcatattcg    240
catagccacg aagaatcaca agtttcgatg accgaaacgg aagtctacga atcaaaagtg    300
attgaacaca ccattacgat cccgccgacc tcgaagttca cgcgctggca gctgaacgca    360
gatgtcggcg gtgctgacat tgaatatatg tacctgatcg atgaagttac cccgattggc    420
ggtacgcaga gtattccgca agtgatcacc tcccgtgcaa aaattatcgt tggtcgccag    480
attatcctgg gcaagaccga aattcgtatc aaacatgctg aacgcaagga atatatgacc    540
gtggttagcc gtaaatcttg gccggcgcc acgctgggtc acagtaaact gtttaagttc    600
gtgctgtacg aagattgggg cggttttcgc atcaaaaccc tgaatacgat gtattctggt    660
tatgaatacg cgtatagctc tgaccagggc ggtatctact tcgatcaagg caccgacaac    720
ccgaaacagc gttgggccat taataagagc ctgccgctgc gccatggtga tgtcgtgacc    780
tttatgaaca aatacttcac gcgttctggt ctgtgctatg atgacggccc ggcgaccaat    840
gtgtattgtc tggataaacg cgaagacaag tggattctgg aagttgtcgg ctaatga      897
```

<210> SEQ ID NO 2
<211> LENGTH: 297
<212> TYPE: PRT
<213> ORGANISM: Eisenia fetida

<400> SEQUENCE: 2

```
Met Ser Ala Lys Ala Ala Glu Gly Tyr Glu Gln Ile Glu Val Asp Val
1               5                   10                  15

Val Ala Val Trp Lys Glu Gly Tyr Val Tyr Glu Asn Arg Gly Ser Thr
            20                  25                  30

Ser Val Asp Gln Lys Ile Thr Ile Thr Lys Gly Met Lys Asn Val Asn
        35                  40                  45

Ser Glu Thr Arg Thr Val Thr Ala Thr His Ser Ile Gly Ser Thr Ile
50                  55                  60

Ser Thr Gly Asp Ala Phe Glu Ile Gly Ser Val Glu Val Ser Tyr Ser
65                  70                  75                  80

His Ser His Glu Glu Ser Gln Val Ser Met Thr Glu Thr Glu Val Tyr
                85                  90                  95

Glu Ser Lys Val Ile Glu His Thr Ile Thr Ile Pro Pro Thr Ser Lys
            100                 105                 110

Phe Thr Arg Trp Gln Leu Asn Ala Asp Val Gly Gly Ala Asp Ile Glu
        115                 120                 125

Tyr Met Tyr Leu Ile Asp Glu Val Thr Pro Ile Gly Gly Thr Gln Ser
130                 135                 140

Ile Pro Gln Val Ile Thr Ser Arg Ala Lys Ile Ile Val Gly Arg Gln
145                 150                 155                 160

Ile Ile Leu Gly Lys Thr Glu Ile Arg Ile Lys His Ala Glu Arg Lys
                165                 170                 175

Glu Tyr Met Thr Val Val Ser Arg Lys Ser Trp Pro Ala Ala Thr Leu
            180                 185                 190

Gly His Ser Lys Leu Phe Lys Phe Val Leu Tyr Glu Asp Trp Gly Gly
        195                 200                 205

Phe Arg Ile Lys Thr Leu Asn Thr Met Tyr Ser Gly Tyr Glu Tyr Ala
210                 215                 220

Tyr Ser Ser Asp Gln Gly Gly Ile Tyr Phe Gln Gly Thr Asp Asn
225                 230                 235                 240

Pro Lys Gln Arg Trp Ala Ile Asn Lys Ser Leu Pro Leu Arg His Gly
                245                 250                 255

Asp Val Val Thr Phe Met Asn Lys Tyr Phe Thr Arg Ser Gly Leu Cys
            260                 265                 270

Tyr Asp Asp Gly Pro Ala Thr Asn Val Tyr Cys Leu Asp Lys Arg Glu
        275                 280                 285

Asp Lys Trp Ile Leu Glu Val Val Gly
290                 295

<210> SEQ ID NO 3
<211> LENGTH: 1830
<212> TYPE: DNA
<213> ORGANISM: Bacteriophage phi-29

<400> SEQUENCE: 3
atgaaacaca tgccgcgtaa aatgtatagc tgcgcgtttg aaaccacgac caaagtggaa    60
gattgtcgcg tttgggccta tggctacatg aacatcgaag atcattctga atacaaaatc   120
ggtaacagtc tggatgaatt tatggcatgg gtgctgaaag ttcaggcgga tctgtacttc   180
cacaacctga atttgatgg cgcattcatt atcaactggc tggaacgtaa tggctttaaa   240
tggagcgcgg atggtctgcc gaacacgtat aataccatta tctctcgtat gggccagtgg   300
tatatgattg atatctgcct gggctacaaa ggtaaacgca aaattcatac cgtgatctat   360
gatagcctga aaaaactgcc gtttccggtg aagaaaattg cgaaagattt caaactgacg   420
```

```
gttctgaaag gcgatattga ttatcacaaa gaacgtccgg ttggttacaa aatcaccccg    480
gaagaatacg catacatcaa aaacgatatc cagatcatcg cagaagcgct gctgattcag    540
tttaaacagg gcctggatcg catgaccgcg ggcagtgata gcctgaaagg tttcaaagat    600
atcatcacga ccaaaaaatt caaaaaagtg ttcccgacgc tgagcctggg tctggataaa    660
gaagttcgtt atgcctaccg cggcggtttt acctggctga cgatcgtttt caagaaaaaa    720
gaaattggcg agggtatggt gtttgatgtt aatagtctgt atccggcaca gatgtacagc    780
cgcctgctgc gtatggcga ccgatcgtg ttcgagggta atatgtttg ggatgaagat    840 tacccgctgc atattcagca catccgttgt gaatttgaac tgaaagaagg ctatattccg    900
accattcaga tcaaacgtag tcgcttctat aagggtaacg aatacctgaa agctctggc    960 ggtgaaatcg cggatctgtg gctgagtaac gtggatctgg aactgatgaa agaacactac   1020
gatctgtaca acgttgaata catcagcggc ctgaaattta agccacgac cggtctgttc   1080 aaagatttca tcgataaatg gacctacatc aaaacgacct ctgaaggcgc gattaaacag   1140
ctggccaaac tgatgctgaa cagcctgtat ggcaaattcg cctctaatcc ggatgtgacc   1200
ggtaaagttc cgtacctgaa agaaaatggc gcactgggtt ttcgcctggg cgaagaagaa   1260
acgaaagatc cggtgtatac cccgatgggt gttttcatta cggcctgggc acgttacacg   1320
accatcaccg cggcccaggc atgctatgat cgcattatct actgtgatac cgattctatt   1380
catctgacgg gcaccgaaat cccggatgtg attaaagata tcgttgatcc gaaaaaactg   1440
ggttattggg cccacgaaag tacgtttaaa cgtgcaaaat acctgcgcca gaaaacctac   1500
atccaggata tctacatgaa agaagtggat ggcaaactgg ttgaaggttc tccggatgat   1560
tacaccgata tcaaattcag tgtgaaatgc gccggcatga cggataaaat caaaaaagaa   1620
gtgaccttcg aaaacttcaa agttggtttc agccgcaaaa tgaaaccgaa accggtgcag   1680
gttccgggcg tgtgtggttct ggtggatgat acgtttacca ttaaatctgg cggtagtgcg   1740
tggagccatc cgcagttcga aaaaggcggt ggctctggtg gcggttctgg cggtagtgcc   1800
tggagccacc cgcagtttga aaaataataa                                    1830
```

<210> SEQ ID NO 4
<211> LENGTH: 608
<212> TYPE: PRT
<213> ORGANISM: Bacteriophage phi-29

<400> SEQUENCE: 4

Met Lys His Met Pro Arg Lys Met Tyr Ser Cys Ala Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe

```
            115                 120                 125
Pro Val Lys Lys Ile Ala Lys Asp Phe Lys Leu Thr Val Leu Lys Gly
        130                 135                 140
Asp Ile Asp Tyr His Lys Glu Arg Pro Val Gly Tyr Lys Ile Thr Pro
145                 150                 155                 160
Glu Glu Tyr Ala Tyr Ile Lys Asn Asp Ile Gln Ile Ala Glu Ala
                165                 170                 175
Leu Leu Ile Gln Phe Lys Gln Gly Leu Asp Arg Met Thr Ala Gly Ser
                180                 185                 190
Asp Ser Leu Lys Gly Phe Lys Asp Ile Ile Thr Thr Lys Lys Phe Lys
                195                 200                 205
Lys Val Phe Pro Thr Leu Ser Leu Gly Leu Asp Lys Glu Val Arg Tyr
        210                 215                 220
Ala Tyr Arg Gly Gly Phe Thr Trp Leu Asn Asp Arg Phe Lys Glu Lys
225                 230                 235                 240
Glu Ile Gly Glu Gly Met Val Phe Asp Val Asn Ser Leu Tyr Pro Ala
                245                 250                 255
Gln Met Tyr Ser Arg Leu Leu Pro Tyr Gly Glu Pro Ile Val Phe Glu
                260                 265                 270
Gly Lys Tyr Val Trp Asp Glu Asp Tyr Pro Leu His Ile Gln His Ile
                275                 280                 285
Arg Cys Glu Phe Glu Leu Lys Glu Gly Tyr Ile Pro Thr Ile Gln Ile
        290                 295                 300
Lys Arg Ser Arg Phe Tyr Lys Gly Asn Glu Tyr Leu Lys Ser Ser Gly
305                 310                 315                 320
Gly Glu Ile Ala Asp Leu Trp Leu Ser Asn Val Asp Leu Glu Leu Met
                325                 330                 335
Lys Glu His Tyr Asp Leu Tyr Asn Val Glu Tyr Ile Ser Gly Leu Lys
                340                 345                 350
Phe Lys Ala Thr Thr Gly Leu Phe Lys Asp Phe Ile Asp Lys Trp Thr
                355                 360                 365
Tyr Ile Lys Thr Thr Ser Glu Gly Ala Ile Lys Gln Leu Ala Lys Leu
        370                 375                 380
Met Leu Asn Ser Leu Tyr Gly Lys Phe Ala Ser Asn Pro Asp Val Thr
385                 390                 395                 400
Gly Lys Val Pro Tyr Leu Lys Glu Asn Gly Ala Leu Gly Phe Arg Leu
                405                 410                 415
Gly Glu Glu Glu Thr Lys Asp Pro Val Tyr Thr Pro Met Gly Val Phe
                420                 425                 430
Ile Thr Ala Trp Ala Arg Tyr Thr Thr Ile Thr Ala Ala Gln Ala Cys
                435                 440                 445
Tyr Asp Arg Ile Ile Tyr Cys Asp Thr Asp Ser Ile His Leu Thr Gly
        450                 455                 460
Thr Glu Ile Pro Asp Val Ile Lys Asp Ile Val Asp Pro Lys Lys Leu
465                 470                 475                 480
Gly Tyr Trp Ala His Glu Ser Thr Phe Lys Arg Ala Lys Tyr Leu Arg
                485                 490                 495
Gln Lys Thr Tyr Ile Gln Asp Ile Tyr Met Lys Glu Val Asp Gly Lys
                500                 505                 510
Leu Val Glu Gly Ser Pro Asp Asp Tyr Thr Asp Ile Lys Phe Ser Val
                515                 520                 525
Lys Cys Ala Gly Met Thr Asp Lys Ile Lys Lys Glu Val Thr Phe Glu
                530                 535                 540
```

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys Ser
                565                 570                 575

Gly Gly Ser Ala Trp Ser His Pro Gln Phe Glu Lys Gly Gly Gly Ser
            580                 585                 590

Gly Gly Gly Ser Gly Gly Ser Ala Trp Ser His Pro Gln Phe Glu Lys
        595                 600                 605

<210> SEQ ID NO 5
<211> LENGTH: 1390
<212> TYPE: DNA
<213> ORGANISM: Escherichia coli

<400> SEQUENCE: 5

| | |
|---|---|
| atgatgaacg atggcaaaca gcagagcacc ttcctgtttc atgattatga aaccttcggt | 60 |
| acccatccgg ccctggatcg tccggcgcag tttgcggcca ttcgcaccga tagcgaattc | 120 |
| aatgtgattg cgaaccggaa gtgttttat tgcaaaccgg ccgatgatta tctgccgcag | 180 |
| ccgggtgcgg tgctgattac cggtattacc ccgcaggaag cgcgcgcgaa aggtgaaaac | 240 |
| gaagcggcgt tgccgcgcg cattcatagc ctgtttaccg tgccgaaaac ctgcattctg | 300 |
| ggctataaca atgtgcgctt cgatgatgaa gttacccgta atatctttta tcgtaacttt | 360 |
| tatgatccgt atgcgtggag ctggcagcat gataacagcc gttgggatct gctggatgtg | 420 |
| atgcgcgcgt gctatgcgct cgcccggaa ggcattaatt ggccggaaaa cgatgatggc | 480 |
| ctgccgagct ttcgtctgga acatctgacc aaagccaacg gcattgaaca tagcaatgcc | 540 |
| catgatgcga tggccgatgt ttatgcgacc attgcgatgg cgaaactggt taaaacccgt | 600 |
| cagccgcgcc tgtttgatta tctgtttacc caccgtaaca acacaaact gatggcgctg | 660 |
| attgatgttc cgcagatgaa accgctggtg catgtgagcg gcatgtttgg cgcctggcgc | 720 |
| ggcaacacca gctgggtggc cccgctggcc tggcacccgg aaaatcgtaa cgccgtgatt | 780 |
| atggttgatc tggccggtga tattagcccg ctgctggaac tggatagcga taccctgcgt | 840 |
| gaacgcctgt ataccgccaa aaccgatctg gcgataatg ccgccgtgcc ggtgaaactg | 900 |
| gttcacatta acaaatgccc ggtgctggcc caggcgaaca ccctgcgccc ggaagatgcg | 960 |
| gatcgtctgg gtattaatcg ccagcattgt ctggataatc tgaaaatcct gcgtgaaaac | 1020 |
| ccgcaggtgc gtgaaaaagt ggtggcgatc ttcgcggaag cggaaccgtt caccccgagc | 1080 |
| gataacgtga tgcgcagct gtataacggc ttctttagcg atgccgatcg cgcggcgatg | 1140 |
| aaaatcgttc tggaaaccga accgcgcaat ctgccggcgc tggatattac ctttgttgat | 1200 |
| aaacgtattg aaaaactgct gtttaattat cgtgcgcgca attttccggg tacccctggat | 1260 |
| tatgccgaac agcagcgttg gctggaacat cgtcgtcagg ttttcacccc ggaatttctg | 1320 |
| cagggttatg cggatgaact gcagatgctg gttcagcagt atgccgatga taaagaaaaa | 1380 |
| gtggcgctgc | 1390 |

<210> SEQ ID NO 6
<211> LENGTH: 485
<212> TYPE: PRT
<213> ORGANISM: Escherichia coli

<400> SEQUENCE: 6

Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
            35                  40                  45

Phe Tyr Cys Lys Pro Ala Asp Asp Tyr Leu Pro Gln Pro Gly Ala Val
            50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Cys Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
            115                 120                 125

Gln His Asp Asn Ser Arg Trp Asp Leu Leu Asp Val Met Arg Ala Cys
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
            165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
            195                 200                 205

Phe Thr His Arg Asn Lys His Lys Leu Met Ala Leu Ile Asp Val Pro
            210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
            245                 250                 255

Asn Ala Val Ile Met Val Asp Leu Ala Gly Asp Ile Ser Pro Leu Leu
            260                 265                 270

Glu Leu Asp Ser Asp Thr Leu Arg Glu Arg Leu Tyr Thr Ala Lys Thr
            275                 280                 285

Asp Leu Gly Asp Asn Ala Ala Val Pro Val Lys Leu Val His Ile Asn
            290                 295                 300

Lys Cys Pro Val Leu Ala Gln Ala Asn Thr Leu Arg Pro Glu Asp Ala
305                 310                 315                 320

Asp Arg Leu Gly Ile Asn Arg Gln His Cys Leu Asp Asn Leu Lys Ile
            325                 330                 335

Leu Arg Glu Asn Pro Gln Val Arg Glu Lys Val Val Ala Ile Phe Ala
            340                 345                 350

Glu Ala Glu Pro Phe Thr Pro Ser Asp Asn Val Asp Ala Gln Leu Tyr
            355                 360                 365

Asn Gly Phe Phe Ser Asp Ala Asp Arg Ala Ala Met Lys Ile Val Leu
            370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
            405                 410                 415

Gly Thr Leu Asp Tyr Ala Glu Gln Gln Arg Trp Leu Glu His Arg Arg
            420                 425                 430

```
Gln Val Phe Thr Pro Glu Phe Leu Gln Gly Tyr Ala Asp Glu Leu Gln
        435                 440                 445

Met Leu Val Gln Gln Tyr Ala Asp Asp Lys Glu Lys Val Ala Leu Leu
    450                 455                 460

Lys Ala Leu Trp Gln Tyr Ala Glu Glu Ile Val Ser Gly Ser Gly His
465                 470                 475                 480

His His His His His
            485

<210> SEQ ID NO 7
<211> LENGTH: 804
<212> TYPE: DNA
<213> ORGANISM: Escherichia coli

<400> SEQUENCE: 7
atgaaatttg tctcttttaa tatcaacggc ctgcgcgcca gacctcacca gcttgaagcc    60
atcgtcgaaa agcaccaacc ggatgtgatt ggcctgcagg agacaaaagt tcatgacgat   120
atgtttccgc tcgaagaggt ggcgaagctc ggctacaact gtttttatca cgggcagaaa   180
ggccattatg gcgtggcgct gctgaccaaa gagacgccga ttgccgtgcg tcgcggcttt   240
cccggtgacg acgaagaggc gcagcggcgg attattatgg cggaaatccc ctcactgctg   300
ggtaatgtca ccgtgatcaa cggttacttc ccgcagggtg aaagccgcga ccatccgata   360 aaattccccgg caaaagcgca gttttatcag aatctgcaaa actacctgga aaccgaactc   420
aaacgtgata atccggtact gattatgggc gatatgaata tcagccctac agatctggat   480
atcggcattg gcgaagaaaa ccgtaagcgc tggctgcgta ccgtaaatg ctctttcctg    540 ccggaagagc gcgaatggat ggacaggctg atgagctggg ggttggtcga taccttccgc   600
catgcgaatc cgcaaacagc agatcgtttc tcatggtttg attaccgctc aaaaggtttt   660
gacgataacc gtggtctgcg catcgacctg ctgctcgcca gccaaccgct ggcagaatgt   720
tgcgtagaaa ccggcatcga ctatgaaatc gcagcatgg aaaaaccgtc cgatcacgcc    780
cccgtctggg cgaccttccg ccgc                                          804

<210> SEQ ID NO 8
<211> LENGTH: 268
<212> TYPE: PRT
<213> ORGANISM: Escherichia coli

<400> SEQUENCE: 8

Met Lys Phe Val Ser Phe Asn Ile Asn Gly Leu Arg Ala Arg Pro His
1               5                   10                  15

Gln Leu Glu Ala Ile Val Glu Lys His Gln Pro Asp Val Ile Gly Leu
            20                  25                  30

Gln Glu Thr Lys Val His Asp Asp Met Phe Pro Leu Glu Glu Val Ala
        35                  40                  45

Lys Leu Gly Tyr Asn Val Phe Tyr His Gly Gln Lys Gly His Tyr Gly
    50                  55                  60

Val Ala Leu Leu Thr Lys Glu Thr Pro Ile Ala Val Arg Arg Gly Phe
65                  70                  75                  80

Pro Gly Asp Asp Glu Glu Ala Gln Arg Arg Ile Ile Met Ala Glu Ile
                85                  90                  95

Pro Ser Leu Leu Gly Asn Val Thr Val Ile Asn Gly Tyr Phe Pro Gln
            100                 105                 110

Gly Glu Ser Arg Asp His Pro Ile Lys Phe Pro Ala Lys Ala Gln Phe
        115                 120                 125
```

```
        Tyr Gln Asn Leu Gln Asn Tyr Leu Glu Thr Glu Leu Lys Arg Asp Asn
        130                 135                 140

Pro Val Leu Ile Met Gly Asp Met Asn Ile Ser Pro Thr Asp Leu Asp
        145                 150                 155                 160

Ile Gly Ile Gly Glu Glu Asn Arg Lys Arg Trp Leu Arg Thr Gly Lys
                        165                 170                 175

Cys Ser Phe Leu Pro Glu Glu Arg Glu Trp Met Asp Arg Leu Met Ser
                    180                 185                 190

Trp Gly Leu Val Asp Thr Phe Arg His Ala Asn Pro Gln Thr Ala Asp
                195                 200                 205

Arg Phe Ser Trp Phe Asp Tyr Arg Ser Lys Gly Phe Asp Asn Arg
        210                 215                 220

Gly Leu Arg Ile Asp Leu Leu Ala Ser Gln Pro Leu Ala Glu Cys
        225                 230                 235                 240

Cys Val Glu Thr Gly Ile Asp Tyr Gly Ile Arg Ser Met Glu Lys Pro
                        245                 250                 255

Ser Asp His Ala Pro Val Trp Ala Thr Phe Arg Arg
                    260                 265
```

<210> SEQ ID NO 9
<211> LENGTH: 1275
<212> TYPE: DNA
<213> ORGANISM: Thermus thermophilus

<400> SEQUENCE: 9

```
atgtttcgtc gtaaagaaga tctggatccg ccgctggcac tgctgccgct gaaaggcctg      60
cgcgaagccg ccgcactgct ggaagaagcg ctgcgtcaag gtaaacgcat cgtgttcac     120 ggcgactatg atgcggatgg cctgaccggc accgcgatcc tggttcgtgg tctggccgcc    180
ctgggtgcgg atgttcatcc gtttatcccg caccgcctgg aagaaggcta tggtgtcctg    240
atggaacgct ccccggaaca tctggaagcc tcggacctgt ttctgaccgt tgactgcggc    300
attaccaacc atgcggaact cgcgcgaactg ctggaaaatg gcgtggaagt cattgttacc    360
gatcatcata cgccgggcaa aacgccgccc cgggtctgg tcgtgcatcc ggcgctgacg      420
ccggatctga agaaaaaacc gaccggcgca ggcgtggcgt ttctgctgct gtgggcactg    480
catgaacgcc tggcctgcc ccgccgctg aatacgcgg acctggcagc cgttggcacc       540
attgccgacg ttgccccgct gtggggttgg aatcgtgcac tggtgaaaga aggtctggca    600
cgcatcccgg cttcatcttg ggtgggcctg cgtctgctgg ctgaagccgt gggctatacc    660
ggcaaagcgg tcgaagtcgc tttccgcatc gcgccgcgca tcaatgcggc ttcccgcctg    720
ggcgaagcgg aaaaagccct gcgcctgctg ctgacggatg atgcggcaga agctcaggcg    780
ctggtcggcg aactgcaccg tctgaacgcc gtcgtcaga ccctggaaga agcgatgctg     840
cgcaaactgc tgccgcaggc cgaccccgaa gcgaaagcca tcgttctgct ggacccggaa    900
ggccatccgg gtgttatggg tattgtggcc tctcgcatcc tggaagcgac cctgcgcccg    960
gtctttctgg tggcccaggg caaaggcacc gtgcgttcgc tggctccgat tccgccgtc   1020 gaagcactgc gcagcgcgga agatctgctg ctgcgttatg tggtcataa agaagcggcg   1080 ggtttcgcaa tggatgaagc gctgtttccg gcgttcaaag cacgcgttga agcgtatgcc   1140
gcacgtttcc cggatccggt tcgtgaagtg gcactgctgg atctgctgcc ggaaccgggc   1200
ctgctgccga ggtgttccg tgaactggca ctgctggaac cgtatggtga aggtaacccg   1260
gaaccgctgt tcctg                                                   1275
```

<210> SEQ ID NO 10
<211> LENGTH: 425
<212> TYPE: PRT
<213> ORGANISM: Thermus thermophilus

<400> SEQUENCE: 10

| Met | Phe | Arg | Arg | Lys | Glu | Asp | Leu | Asp | Pro | Leu | Ala | Leu | Leu | Pro |
| 1 | | | | 5 | | | | | 10 | | | | | 15 |

| Leu | Lys | Gly | Leu | Arg | Glu | Ala | Ala | Leu | Leu | Glu | Glu | Ala | Leu | Arg |
| | | | | 20 | | | | | 25 | | | | | 30 |

| Gln | Gly | Lys | Arg | Ile | Arg | Val | His | Gly | Asp | Tyr | Asp | Ala | Asp | Gly | Leu |
| | | | 35 | | | | | 40 | | | | | 45 | | |

| Thr | Gly | Thr | Ala | Ile | Leu | Val | Arg | Gly | Leu | Ala | Ala | Leu | Gly | Ala | Asp |
| | 50 | | | | | 55 | | | | | 60 | | | | |

| Val | His | Pro | Phe | Ile | Pro | His | Arg | Leu | Glu | Glu | Gly | Tyr | Gly | Val | Leu |
| 65 | | | | | 70 | | | | | 75 | | | | | 80 |

| Met | Glu | Arg | Val | Pro | Glu | His | Leu | Glu | Ala | Ser | Asp | Leu | Phe | Leu | Thr |
| | | | | 85 | | | | | 90 | | | | | 95 | |

| Val | Asp | Cys | Gly | Ile | Thr | Asn | His | Ala | Glu | Leu | Arg | Glu | Leu | Leu | Glu |
| | | | 100 | | | | | 105 | | | | | 110 | | |

| Asn | Gly | Val | Glu | Val | Ile | Val | Thr | Asp | His | His | Thr | Pro | Gly | Lys | Thr |
| | | | 115 | | | | | 120 | | | | | 125 | | |

| Pro | Pro | Pro | Gly | Leu | Val | Val | His | Pro | Ala | Leu | Thr | Pro | Asp | Leu | Lys |
| | 130 | | | | | 135 | | | | | 140 | | | | |

| Glu | Lys | Pro | Thr | Gly | Ala | Gly | Val | Ala | Phe | Leu | Leu | Leu | Trp | Ala | Leu |
| 145 | | | | | 150 | | | | | 155 | | | | | 160 |

| His | Glu | Arg | Leu | Gly | Leu | Pro | Pro | Pro | Leu | Glu | Tyr | Ala | Asp | Leu | Ala |
| | | | | 165 | | | | | 170 | | | | | 175 | |

| Ala | Val | Gly | Thr | Ile | Ala | Asp | Val | Ala | Pro | Leu | Trp | Gly | Trp | Asn | Arg |
| | | | 180 | | | | | 185 | | | | | 190 | | |

| Ala | Leu | Val | Lys | Glu | Gly | Leu | Ala | Arg | Ile | Pro | Ala | Ser | Ser | Trp | Val |
| | | | 195 | | | | | 200 | | | | | 205 | | |

| Gly | Leu | Arg | Leu | Leu | Ala | Glu | Ala | Val | Gly | Tyr | Thr | Gly | Lys | Ala | Val |
| | 210 | | | | | 215 | | | | | 220 | | | | |

| Glu | Val | Ala | Phe | Arg | Ile | Ala | Pro | Arg | Ile | Asn | Ala | Ala | Ser | Arg | Leu |
| 225 | | | | | 230 | | | | | 235 | | | | | 240 |

| Gly | Glu | Ala | Glu | Lys | Ala | Leu | Arg | Leu | Leu | Leu | Thr | Asp | Asp | Ala | Ala |
| | | | | 245 | | | | | 250 | | | | | 255 | |

| Glu | Ala | Gln | Ala | Leu | Val | Gly | Glu | Leu | His | Arg | Leu | Asn | Ala | Arg | Arg |
| | | | 260 | | | | | 265 | | | | | 270 | | |

| Gln | Thr | Leu | Glu | Glu | Ala | Met | Leu | Arg | Lys | Leu | Leu | Pro | Gln | Ala | Asp |
| | | | 275 | | | | | 280 | | | | | 285 | | |

| Pro | Glu | Ala | Lys | Ala | Ile | Val | Leu | Leu | Asp | Pro | Glu | Gly | His | Pro | Gly |
| | 290 | | | | | 295 | | | | | 300 | | | | |

| Val | Met | Gly | Ile | Val | Ala | Ser | Arg | Ile | Leu | Glu | Ala | Thr | Leu | Arg | Pro |
| 305 | | | | | 310 | | | | | 315 | | | | | 320 |

| Val | Phe | Leu | Val | Ala | Gln | Gly | Lys | Gly | Thr | Val | Arg | Ser | Leu | Ala | Pro |
| | | | | 325 | | | | | 330 | | | | | 335 | |

| Ile | Ser | Ala | Val | Glu | Ala | Leu | Arg | Ser | Ala | Glu | Asp | Leu | Leu | Leu | Arg |
| | | | 340 | | | | | 345 | | | | | 350 | | |

| Tyr | Gly | Gly | His | Lys | Glu | Ala | Ala | Gly | Phe | Ala | Met | Asp | Glu | Ala | Leu |
| | | | 355 | | | | | 360 | | | | | 365 | | |

| Phe | Pro | Ala | Phe | Lys | Ala | Arg | Val | Glu | Ala | Tyr | Ala | Ala | Arg | Phe | Pro |

```
                370              375              380
Asp Pro Val Arg Glu Val Ala Leu Leu Asp Leu Pro Glu Pro Gly
385                 390                 395                 400

Leu Leu Pro Gln Val Phe Arg Glu Leu Ala Leu Leu Glu Pro Tyr Gly
            405                 410                 415

Glu Gly Asn Pro Glu Pro Leu Phe Leu
            420                 425

<210> SEQ ID NO 11
<211> LENGTH: 738
<212> TYPE: DNA
<213> ORGANISM: Bacteriophage lambda

<400> SEQUENCE: 11
tccggaagcg gctctggtag tggttctggc atgacaccgg acattatcct gcagcgtacc      60
gggatcgatg tgagagctgt cgaacagggg gatgatgcgt ggcacaaatt acggctcggc     120
gtcatcaccg cttcagaagt tcacaacgtg atagcaaaac cccgctccgg aaagaagtgg     180
cctgacatga aaatgtccta cttccacacc ctgcttgctg aggtttgcac cggtgtggct     240
ccggaagtta acgctaaagc actggcctgg gaaaaacagt acgagaacga cgccagaacc     300
ctgtttgaat tcacttccgg cgtgaatgtt actgaatccc cgatcatcta tcgcgacgaa     360
agtatgcgta ccgcctgctc tcccgatggt ttatgcagtg acggcaacgg ccttgaactg     420
aaatgcccgt ttacctcccg ggatttcatg aagttccggc tcggtggttt cgaggccata     480
aagtcagctt acatggccca ggtgcagtac agcatgtggg tgacgcgaaa aaatgcctgg     540
tactttgcca actatgaccc gcgtatgaag cgtgaaggcc tgcattatgt cgtgattgag     600
cgggatgaaa agtacatggc gagttttgac gagatcgtgc cggagttcat cgaaaaaatg     660
gacgaggcac tggctgaaat tggttttgta tttggggagc aatggcgatc tggctctggt     720
tccggcagcg gttccgga                                                  738

<210> SEQ ID NO 12
<211> LENGTH: 226
<212> TYPE: PRT
<213> ORGANISM: Bacteriophage lambda

<400> SEQUENCE: 12

Met Thr Pro Asp Ile Ile Leu Gln Arg Thr Gly Ile Asp Val Arg Ala
1               5                   10                  15

Val Glu Gln Gly Asp Asp Ala Trp His Lys Leu Arg Leu Gly Val Ile
            20                  25                  30

Thr Ala Ser Glu Val His Asn Val Ile Ala Lys Pro Arg Ser Gly Lys
        35                  40                  45

Lys Trp Pro Asp Met Lys Met Ser Tyr Phe His Thr Leu Leu Ala Glu
    50                  55                  60

Val Cys Thr Gly Val Ala Pro Glu Val Asn Ala Lys Ala Leu Ala Trp
65                  70                  75                  80

Gly Lys Gln Tyr Glu Asn Asp Ala Arg Thr Leu Phe Glu Phe Thr Ser
                85                  90                  95

Gly Val Asn Val Thr Glu Ser Pro Ile Ile Tyr Arg Asp Glu Ser Met
            100                 105                 110

Arg Thr Ala Cys Ser Pro Asp Gly Leu Cys Ser Asp Gly Asn Gly Leu
        115                 120                 125

Glu Leu Lys Cys Pro Phe Thr Ser Arg Asp Phe Met Lys Phe Arg Leu
    130                 135                 140
```

Gly Gly Phe Glu Ala Ile Lys Ser Ala Tyr Met Ala Gln Val Gln Tyr
145                 150                 155                 160

Ser Met Trp Val Thr Arg Lys Asn Ala Trp Tyr Phe Ala Asn Tyr Asp
                165                 170                 175

Pro Arg Met Lys Arg Glu Gly Leu His Tyr Val Val Ile Glu Arg Asp
            180                 185                 190

Glu Lys Tyr Met Ala Ser Phe Asp Glu Ile Val Pro Glu Phe Ile Glu
        195                 200                 205

Lys Met Asp Glu Ala Leu Ala Glu Ile Gly Phe Val Phe Gly Glu Gln
    210                 215                 220

Trp Arg
225

<210> SEQ ID NO 13
<211> LENGTH: 760
<212> TYPE: PRT
<213> ORGANISM: Methanococcoides burtonii
<400> SEQUENCE: 13

Met Met Ile Arg Glu Leu Asp Ile Pro Arg Asp Ile Ile Gly Phe Tyr
1               5                   10                  15

Glu Asp Ser Gly Ile Lys Glu Leu Tyr Pro Pro Gln Ala Glu Ala Ile
            20                  25                  30

Glu Met Gly Leu Leu Glu Lys Lys Asn Leu Leu Ala Ala Ile Pro Thr
        35                  40                  45

Ala Ser Gly Lys Thr Leu Leu Ala Glu Leu Ala Met Ile Lys Ala Ile
    50                  55                  60

Arg Glu Gly Gly Lys Ala Leu Tyr Ile Val Pro Leu Arg Ala Leu Ala
65                  70                  75                  80

Ser Glu Lys Phe Glu Arg Phe Lys Glu Leu Ala Pro Phe Gly Ile Lys
                85                  90                  95

Val Gly Ile Ser Thr Gly Asp Leu Asp Ser Arg Ala Asp Trp Leu Gly
            100                 105                 110

Val Asn Asp Ile Ile Val Ala Thr Ser Glu Lys Thr Asp Ser Leu Leu
        115                 120                 125

Arg Asn Gly Thr Ser Trp Met Asp Glu Ile Thr Thr Val Val Val Asp
130                 135                 140

Glu Ile His Leu Leu Asp Ser Lys Asn Arg Gly Pro Thr Leu Glu Val
145                 150                 155                 160

Thr Ile Thr Lys Leu Met Arg Leu Asn Pro Asp Val Gln Val Val Ala
                165                 170                 175

Leu Ser Ala Thr Val Gly Asn Ala Arg Glu Met Ala Asp Trp Leu Gly
            180                 185                 190

Ala Ala Leu Val Leu Ser Glu Trp Arg Pro Thr Asp Leu His Glu Gly
        195                 200                 205

Val Leu Phe Gly Asp Ala Ile Asn Phe Pro Gly Ser Gln Lys Lys Ile
    210                 215                 220

Asp Arg Leu Glu Lys Asp Asp Ala Val Asn Leu Val Leu Asp Thr Ile
225                 230                 235                 240

Lys Ala Glu Gly Gln Cys Leu Val Phe Glu Ser Ser Arg Arg Asn Cys
                245                 250                 255

Ala Gly Phe Ala Lys Thr Ala Ser Ser Lys Val Ala Lys Ile Leu Asp
            260                 265                 270

Asn Asp Ile Met Ile Lys Leu Ala Gly Ile Ala Glu Glu Val Glu Ser

```
                    275                 280                 285
Thr Gly Glu Thr Asp Thr Ala Ile Val Leu Ala Asn Cys Ile Arg Lys
        290                 295                 300
Gly Val Ala Phe His His Ala Gly Leu Asn Ser Asn His Arg Lys Leu
305                 310                 315                 320
Val Glu Asn Gly Phe Arg Gln Asn Leu Ile Lys Val Ile Ser Ser Thr
                325                 330                 335
Pro Thr Leu Ala Ala Gly Leu Asn Leu Pro Ala Arg Arg Val Ile Ile
            340                 345                 350
Arg Ser Tyr Arg Arg Phe Asp Ser Asn Phe Gly Met Gln Pro Ile Pro
        355                 360                 365
Val Leu Glu Tyr Lys Gln Met Ala Gly Arg Ala Gly Arg Pro His Leu
    370                 375                 380
Asp Pro Tyr Gly Glu Ser Val Leu Leu Ala Lys Thr Tyr Asp Glu Phe
385                 390                 395                 400
Ala Gln Leu Met Glu Asn Tyr Val Glu Ala Asp Ala Glu Asp Ile Trp
                405                 410                 415
Ser Lys Leu Gly Thr Glu Asn Ala Leu Arg Thr His Val Leu Ser Thr
            420                 425                 430
Ile Val Asn Gly Phe Ala Ser Thr Arg Gln Glu Leu Phe Asp Phe Phe
        435                 440                 445
Gly Ala Thr Phe Phe Ala Tyr Gln Gln Asp Lys Trp Met Leu Glu Glu
    450                 455                 460
Val Ile Asn Asp Cys Leu Glu Phe Leu Ile Asp Lys Ala Met Val Ser
465                 470                 475                 480
Glu Thr Glu Asp Ile Glu Asp Ala Ser Lys Leu Phe Leu Arg Gly Thr
                485                 490                 495
Arg Leu Gly Ser Leu Val Ser Met Leu Tyr Ile Asp Pro Leu Ser Gly
            500                 505                 510
Ser Lys Ile Val Asp Gly Phe Lys Asp Ile Gly Lys Ser Thr Gly Gly
        515                 520                 525
Asn Met Gly Ser Leu Glu Asp Asp Lys Gly Asp Asp Ile Thr Val Thr
    530                 535                 540
Asp Met Thr Leu Leu His Leu Val Cys Ser Thr Pro Asp Met Arg Gln
545                 550                 555                 560
Leu Tyr Leu Arg Asn Thr Asp Tyr Thr Ile Val Asn Glu Tyr Ile Val
                565                 570                 575
Ala His Ser Asp Glu Phe His Glu Ile Pro Asp Lys Leu Lys Glu Thr
            580                 585                 590
Asp Tyr Glu Trp Phe Met Gly Glu Val Lys Thr Ala Met Leu Leu Glu
        595                 600                 605
Glu Trp Val Thr Glu Val Ser Ala Glu Asp Ile Thr Arg His Phe Asn
    610                 615                 620
Val Gly Glu Gly Asp Ile His Ala Leu Ala Asp Thr Ser Glu Trp Leu
625                 630                 635                 640
Met His Ala Ala Ala Lys Leu Ala Glu Leu Leu Gly Val Glu Tyr Ser
                645                 650                 655
Ser His Ala Tyr Ser Leu Glu Lys Arg Ile Arg Tyr Gly Ser Gly Leu
            660                 665                 670
Asp Leu Met Glu Leu Val Gly Ile Arg Gly Val Gly Arg Val Arg Ala
        675                 680                 685
Arg Lys Leu Tyr Asn Ala Gly Phe Val Ser Val Ala Lys Leu Lys Gly
    690                 695                 700
```

```
Ala Asp Ile Ser Val Leu Ser Lys Leu Val Gly Pro Lys Val Ala Tyr
705                 710                 715                 720

Asn Ile Leu Ser Gly Ile Gly Val Arg Val Asn Asp Lys His Phe Asn
                725                 730                 735

Ser Ala Pro Ile Ser Ser Asn Thr Leu Asp Thr Leu Leu Asp Lys Asn
            740                 745                 750

Gln Lys Thr Phe Asn Asp Phe Gln
        755                 760
```

<210> SEQ ID NO 14
<211> LENGTH: 300
<212> TYPE: PRT
<213> ORGANISM: Eisenia fetida

<400> SEQUENCE: 14

```
Met Ser Ser Ser Thr Val Met Ala Asp Gly Phe Glu Glu Ile Glu Val
1               5                   10                  15

Asp Val Val Ser Val Trp Lys Glu Gly Tyr Ala Tyr Glu Asn Arg Gly
                20                  25                  30

Asn Ser Ser Val Gln Gln Lys Ile Thr Met Thr Lys Gly Met Lys Asn
            35                  40                  45

Leu Asn Ser Glu Thr Lys Thr Leu Thr Ala Thr His Thr Leu Gly Arg
50                  55                  60

Thr Leu Lys Val Gly Asp Pro Phe Glu Ile Ala Ser Val Glu Val Ser
65                  70                  75                  80

Tyr Thr Phe Ser His Gln Lys Ser Gln Val Ser Met Thr Gln Thr Glu
                85                  90                  95

Val Tyr Ser Ser Gln Val Ile Glu His Thr Val Thr Ile Pro Pro Asn
            100                 105                 110

Lys Lys Phe Thr Arg Trp Lys Leu Asn Ala Asp Val Gly Gly Thr Gly
        115                 120                 125

Ile Glu Tyr Met Tyr Leu Ile Asp Glu Val Thr Ala Ile Gly Ala Asp
    130                 135                 140

Leu Thr Ile Pro Glu Val Asn Lys Ser Arg Ala Lys Ile Leu Val Gly
145                 150                 155                 160

Arg Gln Ile His Leu Gly Glu Thr Glu Ile Arg Ile Lys His Ala Glu
                165                 170                 175

Arg Lys Glu Tyr Met Thr Val Ile Ser Arg Lys Ser Trp Pro Ala Ala
            180                 185                 190

Thr Leu Gly Asn Ser Asn Leu Phe Lys Phe Val Leu Phe Glu Asp Ser
        195                 200                 205

Ser Gly Ile Arg Ile Lys Thr Leu Asn Thr Met Tyr Pro Gly Tyr Glu
    210                 215                 220

Trp Ala Tyr Ser Ser Asp Gln Gly Gly Ile Tyr Phe Asp Glu Ser Ser
225                 230                 235                 240

Asp Asn Pro Lys Gln Arg Trp Ala Leu Ser Lys Ala Met Pro Leu Arg
                245                 250                 255

His Gly Asp Val Val Thr Phe Arg Asn Asn Phe Phe Thr Asn Ser Gly
            260                 265                 270

Met Cys Tyr Asp Asp Gly Pro Ala Thr Asn Val Tyr Cys Leu Glu Lys
        275                 280                 285

Arg Glu Asp Lys Trp Ile Leu Glu Val Val Asn Thr
    290                 295                 300
```

```
<210> SEQ ID NO 15
<211> LENGTH: 300
<212> TYPE: PRT
<213> ORGANISM: Eisenia fetida

<400> SEQUENCE: 15
```

Met Ser Ser Arg Ala Gly Ile Ala Glu Gly Tyr Glu Gln Ile Glu Val
1               5                   10                  15

Asp Val Val Ala Val Trp Lys Glu Gly Tyr Val Tyr Glu Asn Arg Gly
            20                  25                  30

Ser Thr Ser Val Glu Gln Lys Ile Lys Ile Thr Lys Gly Met Arg Asn
        35                  40                  45

Leu Asn Ser Glu Thr Lys Thr Leu Thr Ala Ser His Ser Ile Gly Ser
50                  55                  60

Thr Ile Ser Thr Gly Asp Leu Phe Glu Ile Ala Thr Val Asp Val Ser
65                  70                  75                  80

Tyr Ser Tyr Ser His Glu Glu Ser Gln Val Ser Met Thr Glu Thr Glu
                85                  90                  95

Val Tyr Glu Ser Lys Glu Ile Glu His Thr Ile Thr Ile Pro Pro Thr
            100                 105                 110

Ser Lys Phe Thr Arg Trp Gln Leu Asn Ala Asp Val Gly Gly Ala Asp
        115                 120                 125

Ile Glu Tyr Met Tyr Leu Ile Asp Glu Val Thr Pro Ile Gly Gly Thr
130                 135                 140

Leu Ser Ile Pro Gln Val Ile Lys Ser Arg Ala Lys Ile Leu Val Gly
145                 150                 155                 160

Arg Glu Ile Tyr Leu Gly Glu Thr Glu Ile Arg Ile Lys His Ala Asp
                165                 170                 175

Arg Lys Glu Tyr Met Thr Val Val Ser Arg Lys Ser Trp Pro Ala Ala
            180                 185                 190

Thr Leu Gly His Ser Lys Leu Tyr Lys Phe Val Leu Tyr Glu Asp Met
        195                 200                 205

Tyr Gly Phe Arg Ile Lys Thr Leu Asn Thr Met Tyr Ser Gly Tyr Glu
210                 215                 220

Tyr Ala Tyr Ser Ser Asp Gln Gly Gly Ile Tyr Phe Asp Gln Gly Ser
225                 230                 235                 240

Asp Asn Pro Lys Gln Arg Trp Ala Ile Asn Lys Ser Leu Pro Leu Arg
                245                 250                 255

His Gly Asp Val Val Thr Phe Met Asn Lys Tyr Phe Thr Arg Ser Gly
            260                 265                 270

Leu Cys Tyr Tyr Asp Gly Pro Ala Thr Asp Val Tyr Cys Leu Asp Lys
        275                 280                 285

Arg Glu Asp Lys Trp Ile Leu Glu Val Val Lys Pro
290                 295                 300

```
<210> SEQ ID NO 16
<211> LENGTH: 300
<212> TYPE: PRT
<213> ORGANISM: Eisenia fetida

<400> SEQUENCE: 16
```

Met Ser Ala Thr Ala Val Thr Ala Asp Gly Leu Glu Glu Ile Glu Val
1               5                   10                  15

Asp Val Val Ala Val Trp Lys Glu Gly Tyr Val Tyr Glu Asn Arg Gly
            20                  25                  30

Asp Thr Ser Val Glu Gln Lys Ile Thr Met Thr Lys Gly Met Lys Asn

```
            35                  40                  45
Leu Asn Ser Glu Thr Lys Thr Leu Thr Ala Thr His Thr Val Gly Arg
 50                  55                  60

Thr Leu Lys Val Gly Asp Pro Phe Glu Ile Gly Ser Val Glu Val Ser
 65                  70                  75                  80

Tyr Ser Phe Ser His Gln Glu Ser Gln Val Ser Met Thr Gln Thr Glu
                 85                  90                  95

Val Tyr Ser Ser Gln Val Ile Glu His Thr Val Thr Ile Pro Pro Thr
                100                 105                 110

Ser Lys Phe Thr Arg Trp Lys Leu Asn Ala Asp Val Gly Gly Thr Asp
            115                 120                 125

Ile Glu Tyr Met Tyr Leu Ile Asp Glu Val Thr Pro Ile Ser Val Thr
        130                 135                 140

Gln Thr Ile Pro Gln Val Ile Arg Ser Arg Ala Lys Ile Leu Val Gly
145                 150                 155                 160

Arg Gln Ile His Leu Gly Thr Thr Ala Val Arg Ile Lys His Ala Glu
                165                 170                 175

Arg Gln Glu Tyr Met Thr Val Ile Glu Arg Lys Lys Trp Pro Ala Ala
                180                 185                 190

Thr Leu Gly Lys Ser Asn Leu Phe Lys Phe Val Leu Phe Glu Asp Ser
            195                 200                 205

Ser Gly Thr Arg Ile Lys Thr Leu Asn Thr Met Tyr Pro Gly Tyr Glu
        210                 215                 220

Trp Ala Tyr Ser Ser Asp Gln Gly Gly Val Tyr Phe Asp Glu Ser Ser
225                 230                 235                 240

Asp Asn Pro Lys Gln Arg Trp Ala Leu Ser Lys Ala Leu Pro Leu Arg
                245                 250                 255

His Gly Asp Val Val Thr Phe Met Asn Lys Tyr Phe Thr Asn Ser Gly
                260                 265                 270

Leu Cys Tyr Asp Asp Gly Pro Ala Thr Asn Val Tyr Cys Leu Asp Lys
            275                 280                 285

Arg Glu Asp Lys Trp Ile Leu Glu Val Val Asn Pro
        290                 295                 300

<210> SEQ ID NO 17
<211> LENGTH: 252
<212> TYPE: PRT
<213> ORGANISM: Bacillus thuringiensis

<400> SEQUENCE: 17

Met Asp Val Ile Arg Glu Tyr Leu Met Phe Asn Glu Leu Ser Ala Leu
 1               5                  10                  15

Ser Ser Ser Pro Glu Ser Val Arg Ser Arg Phe Ser Ser Ile Tyr Gly
                20                  25                  30

Thr Asn Pro Asp Gly Ile Ala Leu Asn Asn Glu Thr Tyr Phe Asn Ala
            35                  40                  45

Val Lys Pro Pro Ile Thr Ala Gln Tyr Gly Tyr Cys Tyr Lys Asn
 50                  55                  60

Val Gly Thr Val Gln Tyr Val Asn Arg Pro Thr Asp Ile Asn Pro Asn
 65                  70                  75                  80

Val Ile Leu Ala Gln Asp Thr Leu Thr Asn Asn Thr Asn Glu Pro Phe
                85                  90                  95

Thr Thr Thr Ile Thr Ile Thr Gly Ser Phe Asn Ser Thr Val
                100                 105                 110
```

```
Thr Ser Ser Thr Thr Thr Gly Phe Lys Phe Thr Ser Lys Leu Ser Ile
            115                 120                 125

Lys Lys Val Phe Glu Ile Gly Glu Val Ser Phe Ser Thr Thr Ile
130                 135                 140

Gly Thr Ser Glu Thr Thr Thr Glu Thr Ile Thr Val Ser Lys Ser Val
145                 150                 155                 160

Thr Val Thr Val Pro Ala Gln Ser Arg Arg Thr Ile Gln Leu Thr Ala
                165                 170                 175

Lys Ile Ala Lys Glu Ser Ala Asp Phe Ser Ala Pro Ile Thr Val Asp
            180                 185                 190

Gly Tyr Phe Gly Ala Asn Phe Pro Lys Arg Val Gly Pro Gly Gly His
            195                 200                 205

Tyr Phe Trp Phe Asn Pro Ala Arg Asp Val Leu Asn Thr Thr Ser Gly
210                 215                 220

Thr Leu Arg Gly Thr Val Thr Asn Val Ser Ser Phe Asp Phe Gln Thr
225                 230                 235                 240

Ile Val Gln Pro Ala Arg Ser Leu Leu Asp Glu Gln
                245                 250

<210> SEQ ID NO 18
<211> LENGTH: 439
<212> TYPE: PRT
<213> ORGANISM: Enterobacteria phage T4

<400> SEQUENCE: 18

Met Thr Phe Asp Asp Leu Thr Glu Gly Gln Lys Asn Ala Phe Asn Ile
1               5                   10                  15

Val Met Lys Ala Ile Lys Glu Lys Lys His Val Thr Ile Asn Gly
            20                  25                  30

Pro Ala Gly Thr Gly Lys Thr Thr Leu Thr Lys Phe Ile Ile Glu Ala
            35                  40                  45

Leu Ile Ser Thr Gly Glu Thr Gly Ile Ile Leu Ala Ala Pro Thr His
50                  55                  60

Ala Ala Lys Lys Ile Leu Ser Lys Leu Ser Gly Lys Glu Ala Ser Thr
65                  70                  75                  80

Ile His Ser Ile Leu Lys Ile Asn Pro Val Thr Tyr Glu Glu Asn Val
                85                  90                  95

Leu Phe Glu Gln Lys Glu Val Pro Asp Leu Ala Lys Cys Arg Val Leu
            100                 105                 110

Ile Cys Asp Glu Val Ser Met Tyr Asp Arg Lys Leu Phe Lys Ile Leu
            115                 120                 125

Leu Ser Thr Ile Pro Pro Trp Cys Thr Ile Ile Gly Ile Gly Asp Asn
130                 135                 140

Lys Gln Ile Arg Pro Val Asp Pro Gly Glu Asn Thr Ala Tyr Ile Ser
145                 150                 155                 160

Pro Phe Phe Thr His Lys Asp Phe Tyr Gln Cys Glu Leu Thr Glu Val
                165                 170                 175

Lys Arg Ser Asn Ala Pro Ile Ile Asp Val Ala Thr Asp Val Arg Asn
            180                 185                 190

Gly Lys Trp Ile Tyr Asp Lys Val Val Asp Gly His Gly Val Arg Gly
            195                 200                 205

Phe Thr Gly Asp Thr Ala Leu Arg Asp Phe Met Val Asn Tyr Phe Ser
210                 215                 220

Ile Val Lys Ser Leu Asp Asp Leu Phe Glu Asn Arg Val Met Ala Phe
225                 230                 235                 240
```

-continued

Thr Asn Lys Ser Val Asp Lys Leu Asn Ser Ile Ile Arg Lys Lys Ile
                245                 250                 255

Phe Glu Thr Asp Lys Asp Phe Ile Val Gly Glu Ile Ile Val Met Gln
            260                 265                 270

Glu Pro Leu Phe Lys Thr Tyr Lys Ile Asp Gly Lys Pro Val Ser Glu
        275                 280                 285

Ile Ile Phe Asn Asn Gly Gln Leu Val Arg Ile Glu Ala Glu Tyr
    290                 295                 300

Thr Ser Thr Phe Val Lys Ala Arg Gly Val Pro Gly Glu Tyr Leu Ile
305                 310                 315                 320

Arg His Trp Asp Leu Thr Val Glu Thr Tyr Gly Asp Asp Glu Tyr Tyr
                325                 330                 335

Arg Glu Lys Ile Lys Ile Ile Ser Ser Asp Glu Glu Leu Tyr Lys Phe
            340                 345                 350

Asn Leu Phe Leu Gly Lys Thr Ala Glu Thr Tyr Lys Asn Trp Asn Lys
        355                 360                 365

Gly Gly Lys Ala Pro Trp Ser Asp Phe Trp Asp Ala Lys Ser Gln Phe
    370                 375                 380

Ser Lys Val Lys Ala Leu Pro Ala Ser Thr Phe His Lys Ala Gln Gly
385                 390                 395                 400

Met Ser Val Asp Arg Ala Phe Ile Tyr Thr Pro Cys Ile His Tyr Ala
                405                 410                 415

Asp Val Glu Leu Ala Gln Gln Leu Leu Tyr Val Gly Val Thr Arg Gly
            420                 425                 430

Arg Tyr Asp Val Phe Tyr Val
        435

<210> SEQ ID NO 19
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 19
ggcgtctgct tgggtgttta accttttttt ttttt                              35

<210> SEQ ID NO 20
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 20
ggttgtttct gttggtgctg atattgct                                      28

<210> SEQ ID NO 21
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 21
aacacccaag cagacgcctt                                               20

<210> SEQ ID NO 22
<211> LENGTH: 45

```
<212> TYPE: DNA
<213> ORGANISM: Artificial Sequence
<220> FEATURE:
<223> OTHER INFORMATION: Synthetic polynucleotide

<400> SEQUENCE: 22
gcaatatcag caccaacaga aacaaccttt gaggcgagcg gtcaa                    45

<210> SEQ ID NO 23
<211> LENGTH: 10178
<212> TYPE: DNA
<213> ORGANISM: Artificial Sequence
<220> FEATURE:
<223> OTHER INFORMATION: Synthetic polynucleotide

<400> SEQUENCE: 23
caaagtccat gccatcaaac tgctggtttt cattgatgat gcgggaccag ccatcaacgc    60
ccaccaccgg aacgatgcca ttctgcttat caggaaaggc gtaaatttct ttcgtccacg   120
gattaaggcc gtactggttg caacgatca gtaatgcgat gaactgcgca tcgctggcat    180
cacctttaaa tgccgtctgg cgaagagtgg tgatcagttc ctgtgggtcg acagaatcca   240
tgccgacacg ttcagccagc ttcccagcca gcgttgcgag tgcagtactc attcgtttta   300
tacctctgaa tcaatatcaa cctggtggtg agcaatggtt tcaaccatgt accggatgtg   360
ttctgccatg cgctcctgaa actcaacatc gtcatcaaac gcacgggtaa tggattttt    420 gctggccccg tggcgttgca atgatcgat gcatagcgat tcaaacaggt gctggggcag    480 gccttttcc atgtcgtctg ccagttctgc ctctttctct tcacgggcga gctgctggta    540
gtgacgcgcc cagctctgag cctcaagacg atcctgaatg taataagcgt tcatggctga   600
actcctgaaa tagctgtgaa aatatcgccc gcgaaatgcc gggctgatta ggaaaacagg   660 aaaggggggtt agtgaatgct tttgcttgat ctcagtttca gtattaatat ccatttttta   720
taagcgtcga cggcttcacg aaacatcttt tcatcgccaa taaaagtggc gatagtgaat   780
ttagtctgga tagccataag tgtttgatcc attctttggg actcctggct gattaagtat   840
gtcgataagg cgtttccatc cgtcacgtaa tttacgggtg attcgttcaa gtaaagattc   900
ggaagggcag ccagcaacag gccaccctgc aatggcatat gcatggtgt gctccttatt   960 tatacataac gaaaaacgcc tcgagtgaag cgttattggt atgcggtaaa accgcactca  1020
ggcggccttg atagtcatat catctgaatc aaatattcct gatgtatcga tatcggtaat  1080
tcttattcct tcgctaccat ccattggagg ccatccttcc tgaccatttc catcattcca  1140
gtcgaactca cacacaacac catatgcatt taagtcgctt gaaattgcta taagcagagc  1200
atgttgcgcc agcatgatta atacagcatt taatacagag ccgtgtttat tgagtcggta  1260
ttcagagtct gaccagaaat tattaatctg gtgaagtttt tcctctgtca ttacgtcatg  1320
gtcgatttca atttctattg atgctttcca gtcgtaatca atgatgtatt ttttgatgtt  1380
tgacatctgt tcatatcctc acagataaaa aatcgccctc acactggagg caaagaaga   1440 tttccaataa tcagaacaag tcggctcctg tttagttacg agcgacattg ctccgtgtat  1500
tcactcgttg gaatgaatac acagtgcagt gtttattctg ttatttatgc caaaaataaa  1560
ggccactatc aggcagcttt gttgttctgt ttaccaagtt ctctggcaat cattgccgtc  1620
gttcgtattg cccatttatc gacatatttc ccatcttcca ttacaggaaa catttcttca  1680
ggcttaacca tgcattccga ttgcagcttg catccattgc atcgcttgaa ttgtccacac  1740
cattgatttt tatcaatagt cgtagtcata cggatagtcc tggtattgtt ccatcacatc  1800
```

```
ctgaggatgc tcttcgaact cttcaaattc ttcttccata tatcacctta aatagtggat   1860
tgcggtagta aagattgtgc ctgtctttta accacatcag gctcggtggt tctcgtgtac   1920
ccctacagcg agaaatcgga taaactatta caaccoctac agtttgatga gtatagaaat   1980
ggatccactc gttattctcg gacgagtgtt cagtaatgaa cctctggaga gaaccatgta   2040
tatgatcgtt atctgggttg gacttctgct tttaagccca gataactggc ctgaatatgt   2100
taatgagaga atcggtattc ctcatgtgtg gcatgttttc gtctttgctc ttgcattttc   2160
gctagcaatt aatgtgcatc gattatcagc tattgccagc gccagatata agcgatttaa   2220
gctaagaaaa cgcattaaga tgcaaaacga taaagtgcga tcagtaattc aaaaccttac   2280
agaagagcaa tctatggttt tgtgcgcagc ccttaatgaa ggcaggaagt atgtggttac   2340
atcaaaacaa ttcccataca ttagtgagtt gattgagctt ggtgtgttga acaaaacttt   2400
ttcccgatgg aatggaaagc atatattatt ccctattgag gatatttact ggactgaatt   2460
agttgccagc tatgatccat ataatattga gataaagcca aggccaatat ctaagtaact   2520
agataagagg aatcgatttt cccttaattt tctggcgtcc actgcatgtt atgccgcgtt   2580
cgccaggctt gctgtaccat gtgcgctgat tcttgcgctc aatacgttgc aggttgcttt   2640
caatctgttt gtggtattca gccagcactg taaggtctat cggatttagt gcgctttcta   2700
ctcgtgattt cggtttgcga ttcagcgaga gaatagggcg gttaactggt tttgcgctta   2760
ccccaaccaa caggggattt gctgcttcc attgagcctg tttctctgcg cgacgttcgc   2820
ggcggcgtgt tgtgcatcc atctggattc tcctgtcagt tagctttggt ggtgtgtggc   2880
agttgtagtc ctgaacgaaa acccccgcg attggcacat tggcagctaa tccggaatcg   2940
cacttacggc caatgcttcg tttcgtatca cacaccccaa agccttctgc tttgaatgct   3000
gcccttcttc agggcttaat ttttaagagc gtcaccttca tggtggtcag tgcgtcctgc   3060
tgatgtgctc agtatcaccg ccagtggtat ttatgtcaac accgccagag ataatttatc   3120
accgcagatg gttatctgta tgttttttat atgaatttat tttttgcagg ggggcattgt   3180
ttggtaggtg agagatctga attgctatgt ttagtgagtt gtatctattt attttttcaat   3240
aaatacaatt ggttatgtgt tttgggggcg atcgtgaggc aaagaaaacc cggcgctgag   3300
gccgggttat tcttgttctc tggtcaaatt atatagttgg aaaacaagga tgcatatatg   3360
aatgaacgat gcagaggcaa tgccgatggc gatagtgggt atcatgtagc cgcttatgct   3420
ggaaagaagc aataacccgc agaaaaacaa agctccaagc tcaacaaaac taagggcata   3480
gacaataact accgatgtca tacccata ctctctaatc ttggccagtc ggcgcgttct   3540
gcttccgatt agaaacgtca aggcagcaat caggattgca atcatggttc ctgcatatga   3600
tgacaatgtc gccccaagac catctctatg agctgaaaaa gaaacaccag gaatgtagtg   3660
gcggaaaagg agatagcaaa tgcttacgat aacgtaagga attattacta tgtaaacacc   3720
aggcatgatt ctgttccgca taattactcc tgataattaa tccttaactt tgcccacctg   3780
ccttttaaaa cattccagta tatcactttt cattcttgcg tagcaatatg ccatctcttc   3840
agctatctca gcattggtga ccttgttcag aggcgctgag agatggcctt tttctgatag   3900
ataatgttct gttaaaatat ctccggcctc atcttttgcc cgcaggctaa tgtctgaaaa   3960
ttgaggtgac gggttaaaaa taatatcctt ggcaacctt tttatatccc ttttaaattt   4020
tggcttaatg actatatcca atgagtcaaa aagctcccct tcaatatctg ttgcccctaa   4080
gacctttaat atatcgccaa atacaggtag cttggcttct accttcaccg ttgttcggcc   4140
gatgaaatgc atatgcataa catcgtcttt ggtggttccc ctcatcagtg gctctatctg   4200
```

```
aacgcgctct ccactgctta atgacattcc tttcccgatt aaaaaatctg tcagatcgga    4260
tgtggtcggc ccgaaaacag ttctggcaaa accaatggtg tcgccttcaa caaacaaaaa    4320
agatgggaat cccaatgatt cgtcatctgc gaggctgttc ttaatatctt caactgaagc    4380
tttagagcga tttatcttct gaaccagact cttgtcattt gttttggtaa agagaaaagt    4440
ttttccatcg attttatgaa tatacaaata attggagcca acctgcaggt gatgattatc    4500
agccagcaga gaattaagga aaacagacag gtttattgag cgcttatctt tcccttttatt    4560 tttgctgcgg taagtcgcat aaaaaccatt cttcataatt caatccattt actatgttat    4620
gttctgaggg gagtgaaaat tcccctaatt cgatgaagat tcttgctcaa ttgttatcag    4680
ctatgcgccg accagaacac cttgccgatc agccaaacgt ctcttcaggc cactgactag    4740
cgataacttt ccccacaacg gaacaactct cattgcatgg gatcattggg tactgtgggt    4800
ttagtggttg taaaaacacc tgaccgctat ccctgatcag tttcttgaag gtaaactcat    4860
cacccccaag tctggctatg cagaaatcac ctggctcaac agcctgctca gggtcaacga    4920
gaattaacat tccgtcagga aagcttggct tggagcctgt tggtgcggtc atggaattac    4980
cttcaacctc aagccagaat gcagaatcac tggctttttt ggttgtgctt acccatctct    5040
ccgcatcacc tttggtaaag gttctaagct taggtgagaa catccctgcc tgaacatgag    5100
aaaaaacagg gtactcatac tcacttctaa gtgacggctg catactaacc gcttcataca    5160
tctcgtagat ttctctggcg attgaagggc taaattcttc aacgctaact ttgagaatttt    5220 ttgtaagcaa tgcggcgtta taagcattta atgcattgat gccattaaat aaagcaccaa    5280
cgcctgactg ccccatcccc atcttgtctg cgacagattc ctgggataag ccaagttcat    5340
ttttcttttt ttcataaatt gctttaaggc gacgtgcgtc ctcaagctgc tcttgtgtta    5400
atggtttctt ttttgtgctc atacgttaaa tctatcaccg caagggataa atatctaaca    5460
ccgtgcgtgt tgactatttt acctctggcg gtgataatgg ttgcatgtac taaggaggtt    5520
gtatggaaca acgcataacc ctgaaagatt atgcaatgcg ctttgggcaa accaagacag    5580
ctaaagatct cggcgtatat caaagcgcga tcaacaaggc cattcatgca ggccgaaaga    5640 ttttttttaac tataaacgct gatggaagcg tttatgcgga agaggtaaag cccttcccga    5700
gtaacaaaaa aacaacagca taaataaccc cgctcttaca cattccagcc ctgaaaaagg    5760
gcatcaaatt aaaccacacc tatggtgtat gcatttattt gcatacattc aatcaattgt    5820
tatctaagga aatacttaca tatggttcgt gcaaacaaac gcaacgaggc tctacgaatc    5880
gagagtgcgt tgcttaacaa aatcgcaatg cttggaactg agaagacagc ggaagctgtg    5940
ggcgttgata agtcgcagat cagcaggtgg aagagggact ggattccaaa gttctcaatg    6000
ctgcttgctg ttcttgaatg gggggtcgtt gacgacgaca tggctcgatt ggcgcgacaa    6060
gttgctgcga ttctcaccaa taaaaaacgc ccggcggcaa ccgagcgttc tgaacaaatc    6120
cagatggagt tctgaggtca ttactggatc tatcaacagg agtcattatg acaaatacag    6180
caaaaatact caacttcggc agaggtaact ttgccggaca ggagcgtaat gtggcagatc    6240
tcgatgatgg ttacgccaga ctatcaaata tgctgcttga ggcttattcg ggcgcagatc    6300
tgaccaagcg acagtttaaa gtgctgcttg ccattctgcg taaaacctat gggtggaata    6360
aaccaatgga cagaatcacc gattctcaac ttagcgagat tacaaagtta cctgtcaaac    6420
ggtgcaatga agccaagtta gaactcgtca gaatgaatat tatcaagcag caaggcggca    6480
tgtttggacc aaataaaaac atctcagaat ggtgcatccc tcaaaacgag ggaaaatccc    6540
```

```
ctaaaacgag ggataaaaca tccctcaaat tgggggattg ctatccctca aaacagggg    6600 acacaaaaga cactattaca aaagaaaaaa gaaaagatta ttcgtcagag aattctggcg    6660
aatcctctga ccagccagaa aacgaccttt ctgtggtgaa accggatgct gcaattcaga    6720
gcggcagcaa gtgggggaca gcagaagacc tgaccgccgc agagtggatg tttgacatgg    6780
tgaagactat cgcaccatca gccagaaaac cgaattttgc tgggtgggct aacgatatcc    6840
gcctgatgcg tgaacgtgac ggacgtaacc accgcgacat gtgtgtgctg ttccgctggg    6900
catgccagga caacttctgg tccggtaacg tgctgagccc ggccaaactc cgcgataagt    6960
ggacccaact cgaaatcaac cgtaacaagc aacaggcagg cgtgacagcc agcaaaccaa    7020
aactcgacct gacaaacaca gactggattt acggggtgga tctatgaaaa acatcgccgc    7080
acagatggtt aactttgacc gtgagcagat gcgtcggatc gccaacaaca tgccggaaca    7140
gtacgacgaa aagccgcagg tacagcaggt agcgcagatc atcaacggtg tgttcagcca    7200
gttactggca actttcccgg cgagcctggc taaccgtgac cagaacgaag tgaacgaaat    7260
ccgtcgccag tgggttctgg cttttcggga aaacgggatc accacgatgg aacaggttaa    7320
cgcaggaatg cgcgtagccc gtcggcagaa tcgaccattt ctgccatcac ccgggcagtt    7380
tgttgcatgg tgccgggaag aagcatccgt taccgccgga ctgccaaacg tcagcgagct    7440
ggttgatatg gtttacgagt attgccggaa gcgaggcctg tatccggatg cggagtctta    7500
tccgtggaaa tcaaacgcgc actactggct ggttaccaac ctgtatcaga acatgcgggc    7560
caatgcgctt actgatgcgg aattacgccg taaggccgca gatgagcttg tccatatgac    7620
tgcgagaatt aaccgtggtg aggcgatccc tgaaccagta aaacaacttc ctgtcatggg    7680
cggtagacct ctaaatcgtg cacaggctct ggcgaagatc gcagaaatca agctaagtt    7740 cggactgaaa ggagcaagtg tatgacgggc aaagaggcaa ttattcatta cctggggacg    7800
cataatagct tctgtgcgcc ggacgttgcc gcgctaacag gcgcaacagt aaccagcata    7860
aatcaggccg cggctaaaat ggcacgggca ggtcttctgg ttatcgaagg taaggtctgg    7920
cgaacggtgt attaccggtt tgctaccagg gaagaacggg aaggaaagat gagcacgaac    7980
ctggttttta aggagtgtcg ccagagtgcc gcgatgaaac gggtattggc ggtatatgga    8040
gttaaaagat gaccatctac attactgagc taataacagg cctgctggta atcgcaggcc    8100 ttttatttg gggagagggg aagtcatgaa aaaactaacc tttgaaattc gatctccagc    8160
acatcagcaa aacgctattc acgcagtaca gcaaatcctt ccagacccaa ccaaaccaat    8220
cgtagtaacc attcaggaac gcaaccgcag cttagaccaa acaggaagc tatgggcctg    8280 cttaggtgac gtctctcgtc aggttgaatg gcatggtcgc tggctggatg cagaaagctg    8340
gaagtgtgtg tttaccgcag cattaaagca gcaggatgtt gttcctaacc ttgccgggaa    8400
tggctttgtg gtaataggcc agtcaaccag caggatgcgt gtaggcgaat tgcggagct    8460 attagagctt atacaggcat tcggtacaga gcgtggcgtt aagtggtcag acgaagcgag    8520
actggctctg gagtggaaag cgagatgggg agacagggct gcatgataaa tgtcgttagt    8580
ttctccggtg gcaggacgtc agcatatttg ctctggctaa tggagcaaaa gcgacgggca    8640
ggtaaagacg tgcattacgt tttcatggat acaggttgtg aacatccaat gacatatcgg    8700
tttgtcaggg aagttgtgaa gttctgggat ataccgctca ccgtattgca ggttgatatc    8760
aacccggagc ttggacagcc aaatggttat acggtatggg aaccaaagga tattcagacg    8820
cgaatgcctt ttctgaagcc atttatcgat atggtaaaga aatatggcac tccatacgtc    8880
ggcggcgcgt tctgcactga cagattaaaa ctcgttccct tcaccaaata ctgtgatgac    8940
```

```
catttcgggc gagggaatta caccacgtgg attggcatca gagctgatga accgaagcgg    9000
ctaaagccaa agcctggaat cagatatctt gctgaactgt cagactttga gaaggaagat    9060
atcctcgcat ggtggaagca acaaccattc gatttgcaaa taccggaaca tctcggtaac    9120
tgcatattct gcattaaaaa atcaacgcaa aaaatcggac ttgcctgcaa agatgaggag    9180
ggattgcagc gtgtttttaa tgaggtcatc acgggatccc atgtgcgtga cggacatcgg    9240
gaaacgccaa aggagattat gtaccgagga agaatgtcgc tggacggtat cgcgaaaatg    9300
tattcagaaa atgattatca agccctgtat caggacatgg tacgagctaa aagattcgat    9360
accggctctt gttctgagtc atgcgaaata tttggagggc agcttgattt cgacttcggg    9420
agggaagctg catgatgcga tgttatcggt gcggtgaatg caaagaagat aaccgcttcc    9480
gaccaaatca accttactgg aatcgatggt gtctccggtg tgaaagaaca ccaacagggg    9540
tgttaccact accgcaggaa aaggaggacg tgtggcgaga cagcgacgaa gtatcaccga    9600
cataatctgc gaaaactgca aataccttcc aacgaaacgc accagaaata aacccaagcc    9660
aatcccaaaa gaatctgacg taaaaacctt caactacacg gctcacctgt gggatatccg    9720
gtggctaaga cgtcgtgcga ggaaaacaag gtgattgacc aaaatcgaag ttacgaacaa    9780
gaaagcgtcg agcgagcttt aacgtgcgct aactgcggtc agaagctgca tgtgctggaa    9840
gttcacgtgt gtgagcactg ctgcgcagaa ctgatgagcg atccgaatag ctcgatgcac    9900
gaggaagaag atgatggcta aaccagcgcg aagacgatgt aaaaacgatg aatgccggga    9960
atggtttcac cctgcattcg ctaatcagtg gtggtgctct ccagagtgtg gaaccaagat   10020
agcactcgaa cgacgaagta aagaacgcga aaaagcggaa aaagcagcag agaagaaacg   10080
acgacgagag gagcagaaac agaaagataa acttaagatt cgaaaactcg ccttaaagcc   10140
ccgcagttac tggattaaac aagcccaaca agccagga                           10178
```

<210> SEQ ID NO 24
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 24

```
ttgaccgctc gcctc                                                         15
```